US012589092B2

(12) United States Patent
Zhang et al.

(10) Patent No.: US 12,589,092 B2
(45) Date of Patent: Mar. 31, 2026

(54) POLYCYCLIC COMPOUND ACTING AS KINASE INHIBITOR

(71) Applicant: HANGZHOU INNOGATE PHARMA CO., LTD., Hangzhou (CN)

(72) Inventors: Hancheng Zhang, Hangzhou (CN); Xin Cheng, Hangzhou (CN); Wei Jia, Hangzhou (CN); Congcong Cai, Hangzhou (CN)

(73) Assignee: Hangzhou Innogate Pharma Co., Ltd., Hangzhou (CN)

( * ) Notice: Subject to any disclaimer, the term of this patent is extended or adjusted under 35 U.S.C. 154(b) by 759 days.

(21) Appl. No.: 17/757,944

(22) PCT Filed: Jan. 11, 2021

(86) PCT No.: PCT/CN2021/071144

§ 371 (c)(1),
(2) Date: Jun. 24, 2022

(87) PCT Pub. No.: WO2021/139817

PCT Pub. Date: Jul. 15, 2021

(65) Prior Publication Data

US 2023/0095043 A1 Mar. 30, 2023

(30) Foreign Application Priority Data

Jan. 10, 2020 (CN) ......................... 202010027913.8

(51) Int. Cl.

| | |
|---|---|
| ***A61K 31/4375*** | (2006.01) |
| ***A61K 31/4985*** | (2006.01) |
| ***A61K 31/519*** | (2006.01) |
| ***A61P 35/00*** | (2006.01) |

(52) U.S. Cl.

CPC ...... *A61K 31/4375* (2013.01); *A61K 31/4985* (2013.01); *A61K 31/519* (2013.01); *A61P 35/00* (2018.01)

(58) Field of Classification Search

CPC ............ A61K 31/4375; A61K 31/4985; A61K 31/519; A61P 35/00

See application file for complete search history.

(56) References Cited

FOREIGN PATENT DOCUMENTS

| | | | | |
|---|---|---|---|---|
| WO | 2016030439 A1 | 3/2016 | | |
| WO | WO-2017101763 A1 * | 6/2017 | ........... | C07D 471/04 |
| WO | 2018108084 A1 | 6/2018 | | |

OTHER PUBLICATIONS

International Search Report issued Apr. 12, 2021 in PCT/CN2021/071144.

* cited by examiner

*Primary Examiner* — Adam C Milligan
*Assistant Examiner* — Ernesto Valle
(74) *Attorney, Agent, or Firm* — Ice Miller LLP

(57) ABSTRACT

The present invention provides a class of compounds containing tricyclic heteroaryl groups. Specifically, the present invention provides compounds of the structure represented by the following formula (I) (the definition of each group is described in the specification), pharmaceutical compositions containing the compounds of formula (I), as well as optical isomers, pharmaceutical acceptable salts, prodrugs, deuterated derivatives, hydrates, solvates, etc. The compounds of formula (I) can effectively inhibit protein kinases including CDK and/or TRK, thereby playing a role in the treatment of various tumors and related disease.

(I)

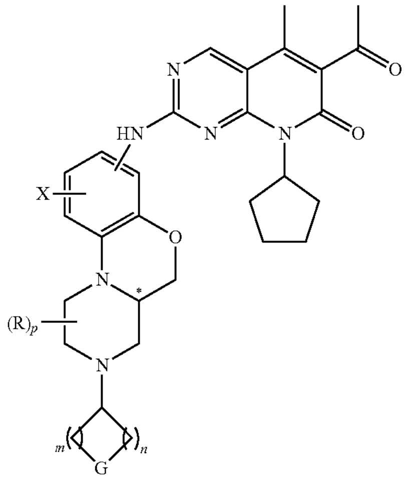

20 Claims, No Drawings

POLYCYCLIC COMPOUND ACTING AS KINASE INHIBITOR

CROSS-REFERENCE TO RELATED APPLICATION

This application is a Section 371 of International Application No. PCT/CN2021/071144 filed Jan. 11, 2021, which was published in the Chinese language Jul. 15, 2021, under International Publication No. WO 2021/139817 A1, which claims priority to Chinese Patent Application No. 202010027913.8 filed Jan. 10, 2020, the disclosures of which are incorporated herein by reference in their entireties.

TECHNICAL FIELD

The present invention relates to the field of medicinal chemistry; specifically, the present invention relates to a new type of derivatives containing tricyclic heteroaryl, its synthetic method and its use as the inhibitor of various kinases, including CDK and/or TRK, in the preparation of drugs for the treatment of tumors and other related diseases.

BACKGROUND OF THE INVENTION

Cancer, also known as malignant tumor, is one of the diseases with the highest morbidity and mortality in the world. It is characterized by abnormal cell proliferation and metastasis, which spreads and metastasizes in a short or relatively short time after the onset of disease. Traditional treatment options include surgery (if the conditions for resection are met), radiotherapy and chemotherapy. The targeted therapies developed in recent years have the advantages of reducing toxicity and side effects, and improving survival rate. However, after using targeted drugs for a period of time, drug resistance will develop, and then the growth and spread of cancer cells will be extremely rapid. Common cancers are: hematological cancer, lung cancer, breast cancer, liver cancer, bladder cancer, rectal cancer, stomach cancer, etc.

The regulation of the cell cycle is mainly affected by a series of serine/threonine kinases. This class of serine/threonine kinases is also called cyclin-dependent kinase (CDK). They promote the progress of cell cycle, the transcription of genetic information and the normal division as well as proliferation of cells by working together with their corresponding regulatory subunit cyclins. The human CDK family has more than 20 subtypes, which are divided into two major categories according to different functions: one type of CDK regulates the cell cycle, such as CDK2/4/6, etc; the other type of CDK participates in transcription regulation/RNA processing, such as CDK7/9 and so on. CDK kinase binds to the cyclin protein to form a specific complex, thereby being activated. In many human cancers, CDK is over activated or the protein that inhibits CDK does not work, leading to abnormal proliferation and division of cancer cells. Therefore, CDK has become an important target of anti-tumor drugs.

CDK2 and CDK4/6 are key regulators of the cell cycle. In the cell resting state (G0 phase), the transcriptional activity of the transcription factor E2F is inhibited by retinoblastoma protein (Rb). When the cell is stimulated by the division signal, the cell enters the G1 phase. In the G1 phase, Cyclin D (CyclinD) binds to and activates CDK4/6, and the activated CDK4/6 phosphorylates Rb, leading to the activation of E2F. At this time, E2F remains bound to the Rb protein, but can transcribe proteins such as CCNE1, CCNA2, CCNB1 and CDK2. In the late G1 phase (after the restriction point), CyclinE binds to and activates CDK2, and CDK2 further phosphorylates Rb, leading to the complete release of Rb and activation of E2F. E2F then induces the transcription of S-phase proteins such as CyclinA and CyclinE. CDK2/CyclinA and CDK1 maintain the phosphorylation of Rb protein to ensure the process of cell division. CDK2/CyclinA assists the conversion process of S/G2 phase. Therefore, inhibiting the kinase activity of CDK2 and CDK4/6 can block the progress of the cell cycle and achieve the purpose of inhibiting tumor proliferation. CDK4/6 inhibitors Palbociclib, Ribociclib and Abemaciclib have been approved for marketing, and there is currently no effective CDK2 inhibitor. CDK9 mainly regulates the RNA transcription process. CDK9 and the corresponding Cyclin form the positive transcription elongation factor complex-b (P-TEFb). Most of CDK9 binds to CyclinT1, only a small amount of CDK9 binds to CyclinT2a, CyclinT2b and CyclinK. CDK9 is the catalytic subunit of the P-TEF complex, which can phosphorylate the C-terminal domain of RNA polymerase II and promote the RNA transcription elongation process of a variety of oncogenes, such as MYC and MCL-1. MYC and MCL-1 are abnormally overexpressed in a variety of cancer types, but there are no effective targeted inhibitors yet. In addition, under the pressure of cell replication, the CDK9/CyclinK complex also plays an important role in maintaining genome stability.

CDK16 is expressed in a variety of human cells and tissue types. The tissues with the highest expression are the brain and testis. The activation of CDK16 depends on CyclinY. Knockout of CDK16 will not affect the normal growth of mice, but will cause infertility in male mice, indicating that CDK16 plays an important role in sperm production. Overexpression of CDK16 can promote the growth and invasion of a variety of cancer cells, such as lung cancer and hepatocarcinoma. This effect may be related to the down-regulation of tumor suppressor p27 by CDK16.

CDK5 is a special protein in the CDK family. Although the protein sequence has many similarities with other CDK members, the main function of CDK5 depends on non-Cyclin proteins, such as p35 and p39. CDK5 is expressed in many human tissues, but its activating factors p35 and p39 are mostly expressed in neurons, so its function is mainly concentrated in the nervous system. By phosphorylating a variety of neuronal proteins, such as Tau, Axin, CRMP2 and Neurofilament, CDK5 can regulate the physiological functions of a variety of neurons, such as neuron migration, axon growth, synapse formation, memory formation, and pain perception, etc. In the neurons of neurodegenerative patients, CDK5 more stably binds to the splice body p25 of p35, and abnormal activation occurs, leading to the degeneration and death of nerve cells. In addition, CDK5 also plays a role in immune response, angiogenesis, cell cycle regulation, DNA damage response, cell senescence and apoptosis. Therefore, CDK5 has gradually become an important target against neurodegenerative diseases and cancer.

The NeuroTrophin Receptor Kinase (NTRK) family includes TRKA, TRKB and TRKC, which are encoded by NTRK1, NTRK2 and NTRK3 genes, respectively, and are usually expressed in nerve tissues. TRK receptors can be activated by a variety of neurotrophic factors. Among them, NGF mainly activates TRKA, BDNF and NT-4/5 mainly activate TRKB, and BT-3 mainly activates TRKC. After binding to the corresponding ligand, TRK dimerization and phosphorylation will occur, further activate downstream signaling pathways such as PI3K/AKT, RAS/RAF/MEK and PLC-gamma to promote cell proliferation and survival.

NTRK gene fusion mutations have been shown to be related to a variety of cancers. Gene fusion allows NTRK genes (mainly NTRK1 and NTRK3) to be fused with other genes, and then transcribed and translated into constitutively activated TRK protein, driving tumor cells with TRK fusion mutations to grow and proliferate. The probability of NTRK fusion mutation accounts for about 0.31% of the total number of adult cancers and 0.34% of the total number of juvenile cancers. NTRK3 fusion mutations are more common in some rare tumors, such as secretory breast cancer, fibrosarcoma and salivary gland cancer. NTRK1 mutations mainly exist in some common cancer types such as lung adenocarcinoma and colon cancer, the incidence of mutations is relatively low. In addition, the excessive activation of the NGF-TRKA signaling pathway also plays an important role in the pathogenesis of inflammatory pain and cancer pain.

In summary, the development of new types of kinase inhibitors targeting CDK and TRK subtypes is of great significance.

SUMMARY OF THE INVENTION

The present invention provides a novel kinase inhibitor which is capable for the inhibition of several kinases such as CDK and TRK.

In the first aspect of the present invention, a compound of the following formula (I), or the optical isomers, pharmaceutically acceptable salts, prodrugs, deuterated forms, hydrates, or solvates thereof is provided:

(I)

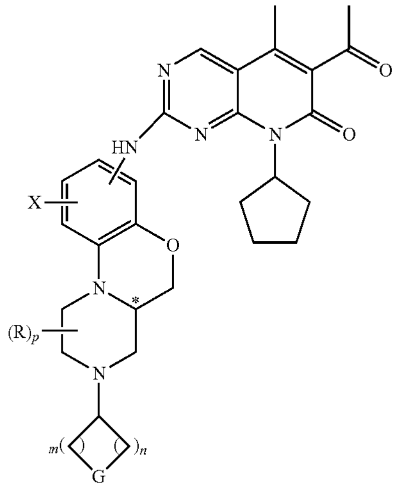

"*" indicates a chiral center;

X is hydrogen, deuterium, halogen, $C_{1-4}$ alkyl, $OR^1$, $NR^1R^2$, or $N(R^1)C(O)R^3$;

each of the R is independently hydrogen or $C_{1-4}$ alkyl; or when two R are simultaneously attached to one carbon atom, the two R and the carbon atom to which they are attached may optionally form a carbonyl group (C=O);

G is $NR^f$, O, S, S(O), $S(O)_2$ or $CR^gR^g$;

p is 0, 1, 2 or 3;

m and n are each independently 0, 1, 2 or 3; with the proviso that m and n cannot simultaneously be 0;

$R^1$ and $R^2$ are each independently hydrogen or $C_{1-4}$ alkyl;

$R^3$ is $C_{1-4}$ alkyl, $C_{2-4}$ alkenyl or $C_{2-4}$ alkynyl;

$R^f$ is hydrogen, $C_{1-4}$ alkyl, $C_{1-4}$ haloalkyl, cyano substituted $C_{1-4}$ alkyl, $C_{2-4}$ alkenyl, $C_{2-4}$ alkynyl, $C_{3-8}$ cycloalkyl, 4- to 8-membered heterocyclyl, aryl, heteroaryl, $C(O)R^4$, $C(O)OR^1$, $C(O)NR^1R^2$, $S(O)_2R^4$, or $S(O)_2NR^1R^2$;

each $R^g$ is independently selected from the group consisting of hydrogen, halogen, or $C_{1-4}$ alkyl; or two $R^g$ together with the carbon atom to which they are attached form a carbonyl group (C=O); or two $R^g$ together with the carbon atom to which they attached form 3- to 8-membered cyclic structure which optionally comprise 0, 1 or 2 heteroatoms selected from N, O or S;

$R^4$ is $C_{1-4}$ alkyl, $C_{2-4}$ alkenyl, $C_{2-4}$ alkynyl, $C_{3-8}$ cycloalkyl, 4- to 8-membered heterocyclic group, aryl, or heteroaryl;

wherein each of the above alkyl, alkenyl, alkynyl, cycloalkyl, heterocyclyl, aryl and heteroaryl is optionally and independently substituted by 1 to 3 substituents which independently selected from the group consisting of halogen, $C_{1-4}$ alkyl, $C_{1-4}$ haloalkyl, $C_{2-4}$ alkenyl, $C_{2-4}$ alkynyl, $C_{3-8}$ cycloalkyl, 3- to 8-membered heterocyclic group, aryl, heteroaryl, CN, $NO_2$, $OR^1$, $SR^1$, $NR^1R^2$, $C(O)R^4$, $C(O)OR^1$, $C(O)NR^1R^2$, $NR^1C(O)R^4$, or $S(O)_2R^4$, provided that the chemical structure formed is stable and meaningful; the $R^1$, $R^2$ and $R^4$ are defined as above;

Unless otherwise specified, the aryl is an aromatic group having 6 to 12 carbon atoms; the heteroaryl is a 5- to 15-membered heteroaromatic group; and the cyclic structure is saturated or unsaturated cyclic group with or without heteroatoms.

In another preferred embodiment, [g1] "*" indicates a chiral center;

X is hydrogen, deuterium, halogen, $C_{1-4}$ alkyl, $OR^1$, $NR^1R^2$, or $NR^1C(O)R^3$;

each of the R is independently hydrogen or $C_{1-4}$ alkyl; or when two R are simultaneously attached to one carbon atom, the two R and the carbon atom to which they are attached may optionally form a carbonyl group (C=O);

G is $NR^f$, O, S, S(O), $S(O)_2$ or $CR^gR^g$;

p is 0, 1, 2 or 3;

m and n are each independently 1, 2 or 3;

$R^1$ and $R^2$ are each independently hydrogen or $C_{1-4}$ alkyl;

$R^3$ is $C_{1-4}$ alkyl, $C_{2-4}$ alkenyl or $C_{2-4}$ alkynyl;

$R^f$ is hydrogen, $C_{1-4}$ alkyl, $C_{1-4}$ haloalkyl, $C_{2-4}$ alkenyl, $C_{2-4}$ alkynyl, $C_{3-8}$ cycloalkyl, 4- to 8-heterocyclyl, aryl, heteroaryl, $C(O)R^4$, $C(O)OR^1$, $C(O)NR^1R^2$, or $S(O)_2R^4$;

each $R^g$ is independently selected from the group consisting of hydrogen, halogen, or $C_{1-4}$ alkyl; or two $R^g$ together with the carbon atom to which they are attached form a carbonyl group (C=O); or two $R^g$ together with the carbon atom to which they attached form a 3- to 8-membered cyclic structure which optionally comprise 0, 1 or 2 heteroatoms selected from N, O or S;

$R^4$ is $C_{1-4}$ alkyl, $C_{2-4}$ alkenyl, $C_{2-4}$ alkynyl, $C_{3-8}$ cycloalkyl, 4- to 8-membered heterocyclic group, aryl, or heteroaryl;

wherein each of the above alkyl, alkenyl, alkynyl, cycloalkyl, heterocyclyl, aryl and heteroaryl is optionally and independently substituted by 1 to 3 substituents which each independently selected from the group consisting of halogen, $C_{1-4}$ alkyl, $C_{1-4}$ haloalkyl, $C_{2-4}$ alkenyl, $C_{2-4}$ alkynyl, $C_{3-8}$ cycloalkyl, 3- to 8-membered heterocyclic group, aryl, heteroaryl, CN, $NO_2$, $OR^1$, $SR^1$, $NR^1R^2$, $C(O)R^4$, $C(O)OR^1$, $C(O)NR^1R^2$, $NR^1C(O)R^4$, or $S(O)_2R^4$, provided that the chemical structure formed is stable and meaningful; the $R^1$, $R^2$ and $R^4$ are defined as above;

Unless otherwise specified, the aryl is aromatic groups having 6 to 12 carbon atoms; the heteroaryl is 5- to 15-membered heteroaromatic groups; and the cyclic structure is saturated or unsaturated cyclic groups with or without heteroatoms.

In another preferred embodiment, the 4- to 8-membered hetero cyclic group is a 4- to 6-membered hetero cyclic group.

In another preferred embodiment, the formula (I) is:

(II)

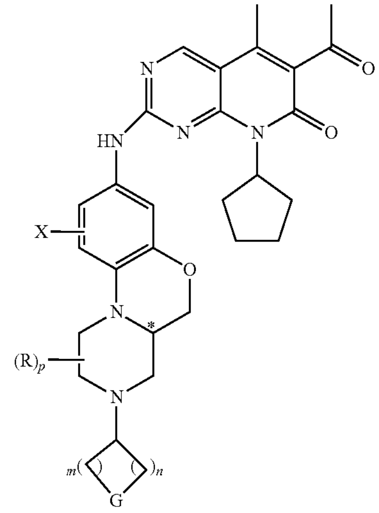

or (III)

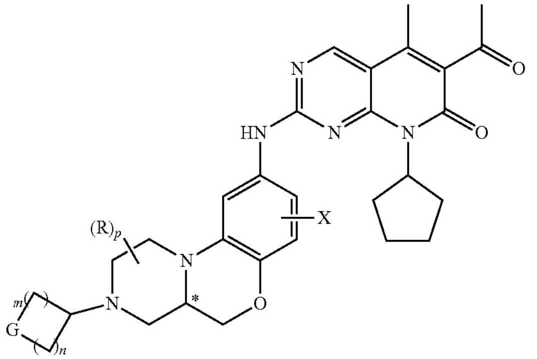

"*" indicates a chiral center;

X, R, G, p, m and n are defined as in the first aspect of the present invention.

In another preferred embodiment, X is hydrogen, halogen, or $C_{1-4}$ alkyl; R is hydrogen, or two R and the carbon atom to which they are attached form a carbonyl group (C═O).

In another preferred embodiment, G is $NR^f$, O or $CR^gR^g$; m and n are each independently 1 or 2; wherein $R^f$ is hydrogen, $C_{1-4}$ alkyl, $C_{1-4}$ haloalkyl, $C_{3-8}$ cycloalkyl, 4- to 8-membered heterocyclic group, aryl, heteroaryl, $C(O)R^4$, or $S(O)_2R^4$; wherein $R^4$ is $C_{1-4}$ alkyl, $C_{2-4}$ alkenyl, $C_{2-4}$ alkynyl, $C_{3-8}$ cycloalkyl, 4- to 8-membered heterocyclic group.

In another preferred embodiment, the

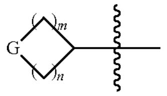

is a 4 to 6 membered ring.

In another preferred embodiment, the formula (I) compound is:

(IV)

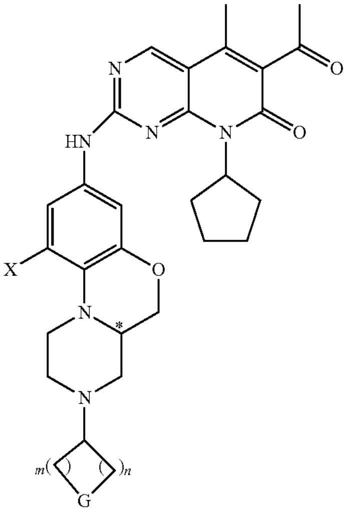

"*" indicates a chiral center;

X is hydrogen, halogen, or $C_{1-4}$ alkyl;

G is $NR^f$, O or $CR^gR^g$; m and n are each independently 1 or 2; wherein $R^f$ is hydrogen, $C_{1-4}$ alkyl, $C_{1-4}$ haloalkyl, $C_{3-8}$ cycloalkyl, 4- to 8-membered heterocyclic group, aryl, heteroaryl, $C(O)R^4$, or $S(O)_2R^4$; wherein $R^4$ is $C_{1-4}$ alkyl, $C_{2-4}$ alkenyl, $C_{2-4}$ alkynyl, $C_{3-8}$ cycloalkyl, 4- to 8-membered heterocyclic group.

In another preferred embodiment, the formula (I) compound is:

(V)

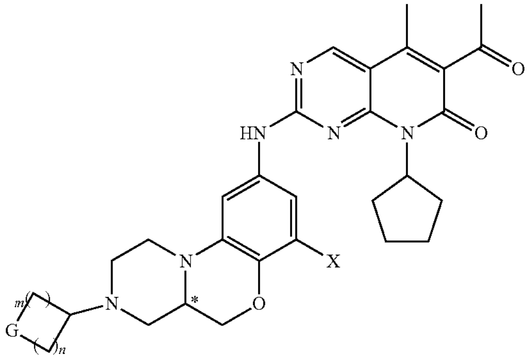

"*" indicates a chiral center;

X is hydrogen, halogen, or $C_{1-4}$ alkyl;

G is $NR^f$, O or $CR^gR^g$; m and n are each independently 1 or 2; wherein $R^C$ is hydrogen, $C_{1-4}$ alkyl, $C_{1-4}$ haloalkyl, $C_{3-8}$ cycloalkyl, 4- to 8-membered heterocyclic group, aryl, heteroaryl, $C(O)R^4$, or $S(O)_2R^4$; wherein $R^4$ is $C_{1-4}$ alkyl, $C_{2-4}$ alkenyl, $C_{2-4}$ alkynyl, $C_{3-8}$ cycloalkyl, 4- to 8-membered heterocyclic group.

In another preferred embodiment, $R^f$ is hydrogen, $C_{1-4}$ alkyl, $C_{1-4}$ haloalkyl, cyano substituted $C_{1-4}$ alkyl, $C_{3-8}$ cycloalkyl, $C(O)R^4$, or $S(O)_2R^4$; wherein $R^4$ is $C_{1-4}$ alkyl.

In another preferred embodiment, each $R^g$ is independently hydrogen or halogen.

In another preferred embodiment, in the formula (IV) or formula (V):

"*" indicates a chiral center;

X is hydrogen, fluorine or methyl;

G is $NR^f$, O or $CR^gR^g$; m and n are each independently 1 or 2; wherein $R^C$ is hydrogen, methyl, ethyl, $CH_2CF_3$, $CH_2CN$, cyclopropyl, $C(O)CH_3$, or $S(O)_2CH_3$; each $R^g$ is independently hydrogen or fluorine.

In another preferred embodiment, the formula (I) is a compound selected from the following compounds, or the mixture with the corresponding enantiomer thereof:

1S

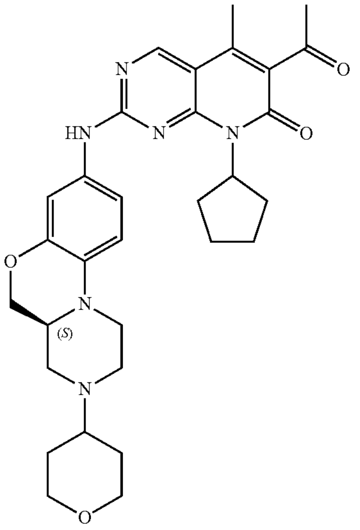

1R

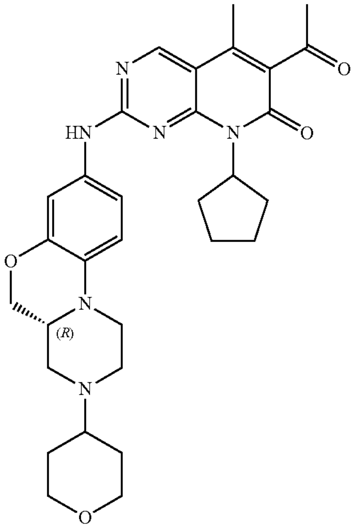

-continued

2S

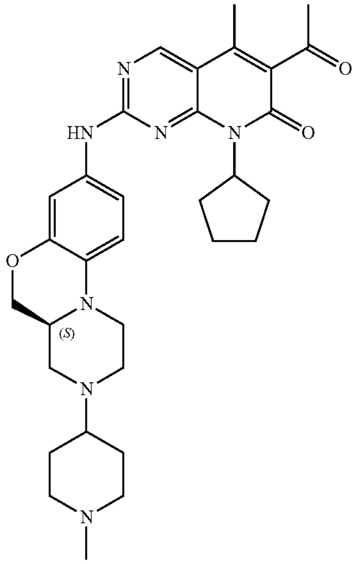

2R

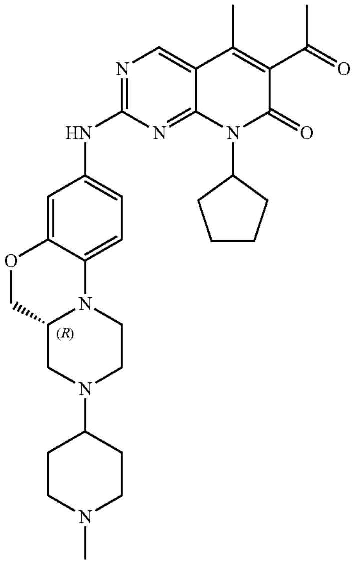

-continued
3S
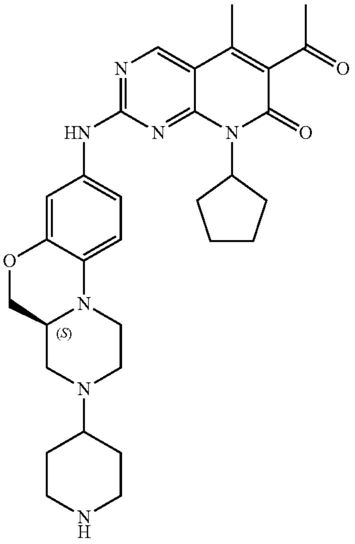
3R
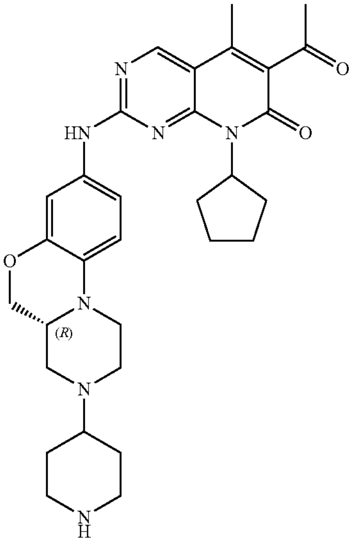
-continued
4S
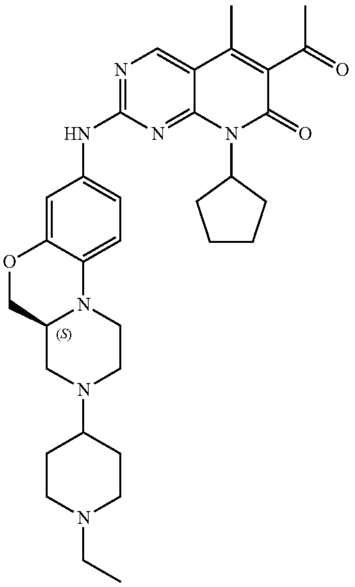
4R
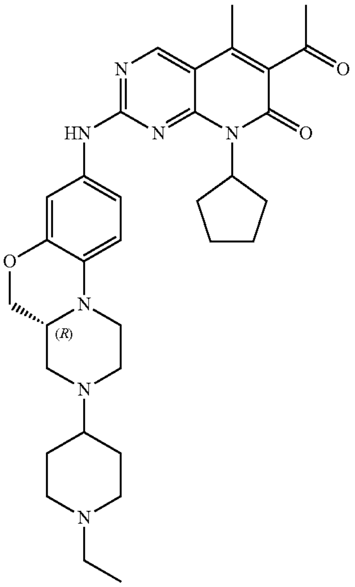

-continued
5S
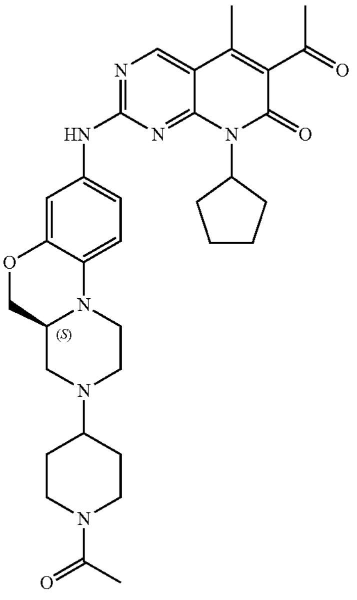
5R
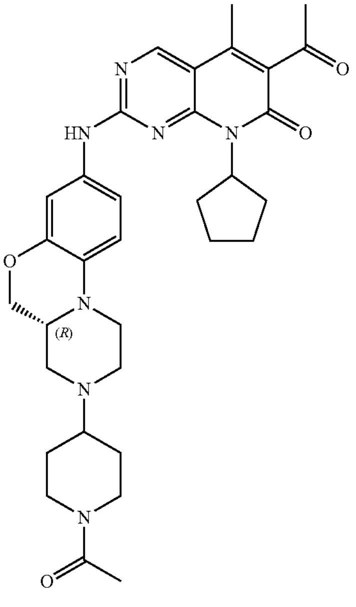
-continued
6S
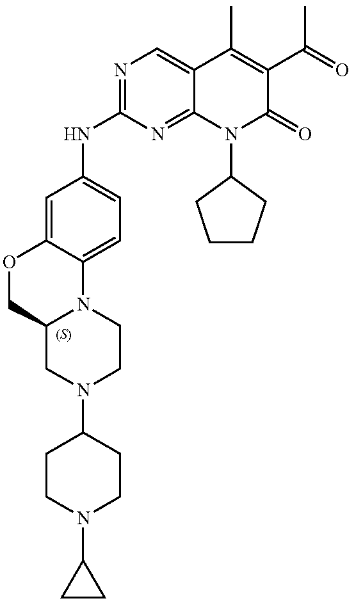
6R
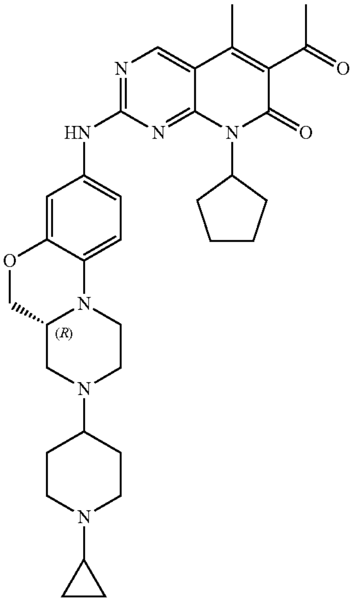

7S
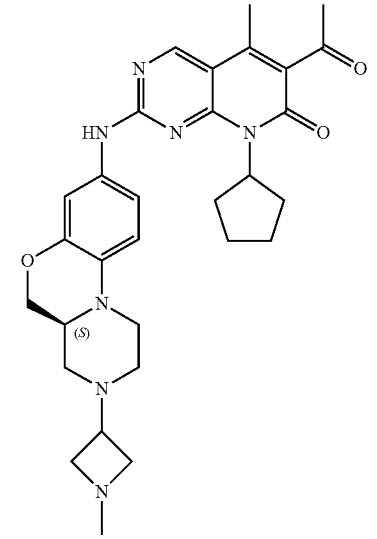
7R
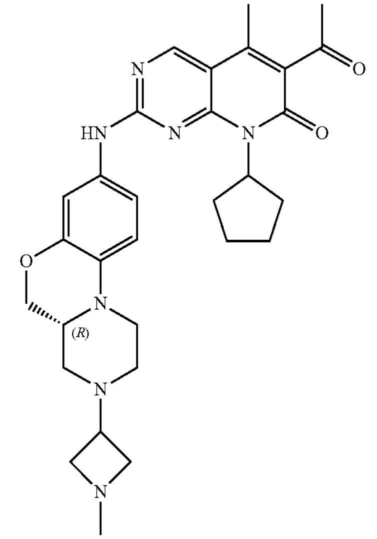
8S
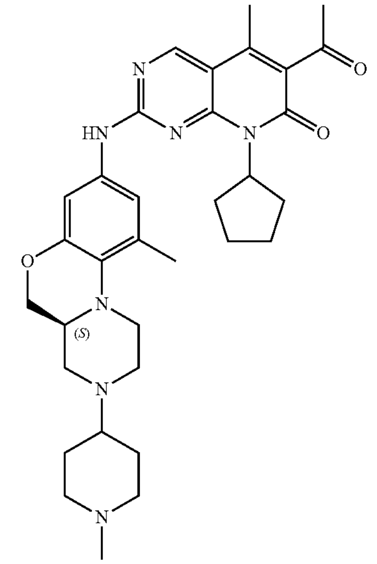
8R
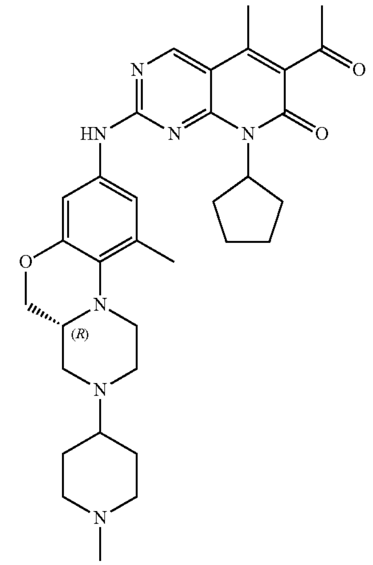
9S
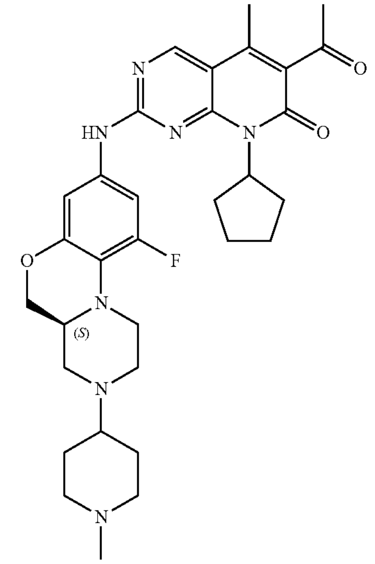

-continued
9R
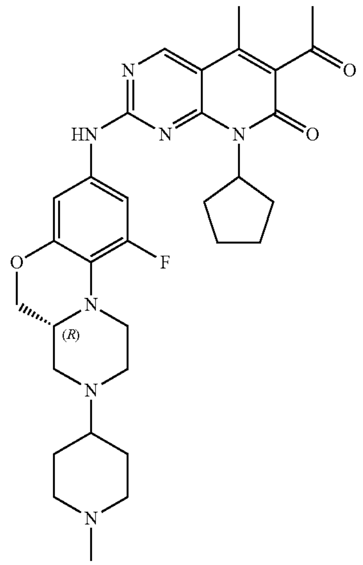
10S
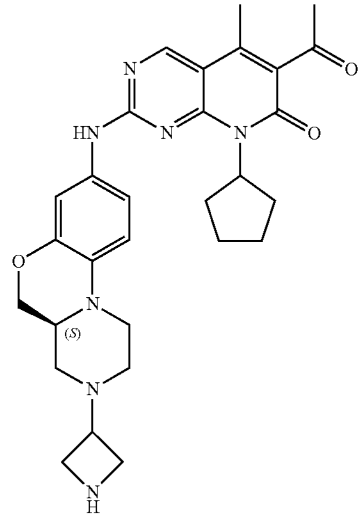
10R
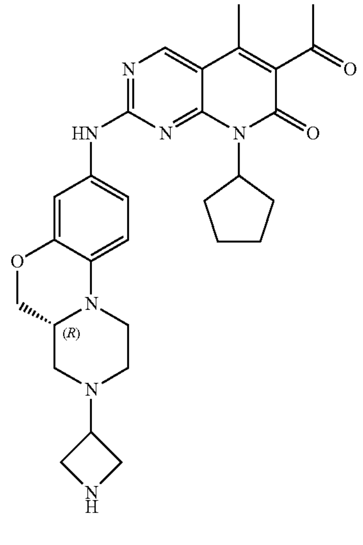
-continued
11S
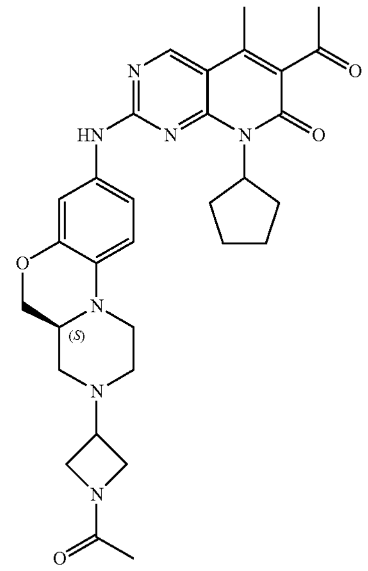
11R
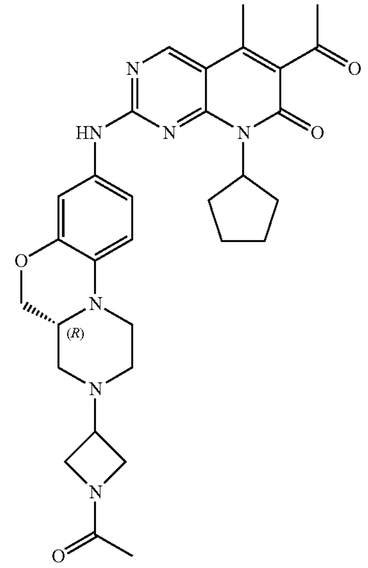

-continued
12S
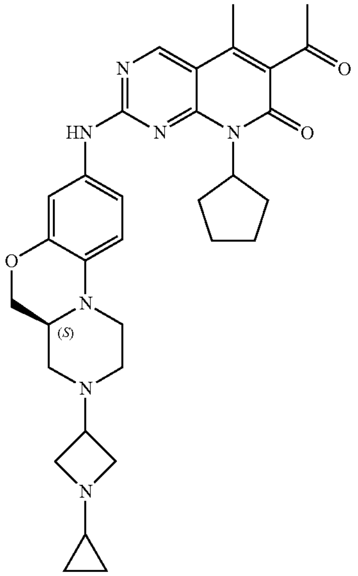
12R
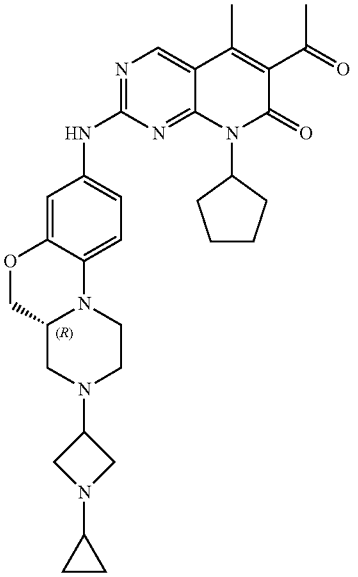
13S
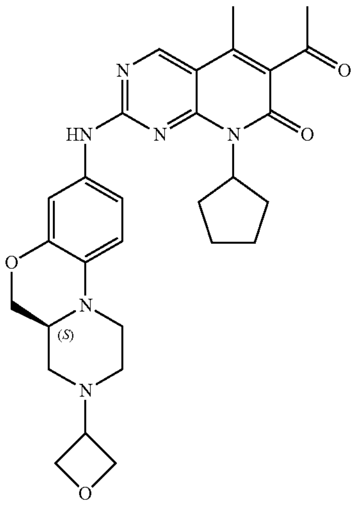
-continued
13R
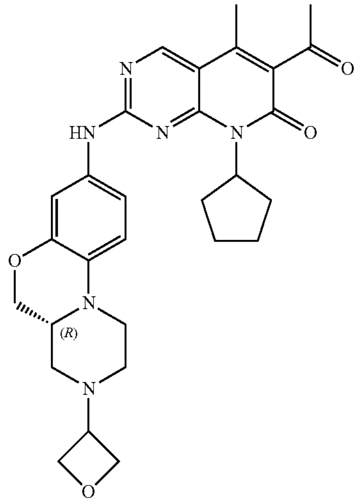
14S
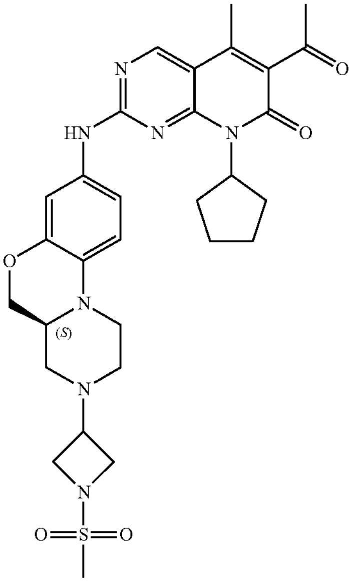
14R
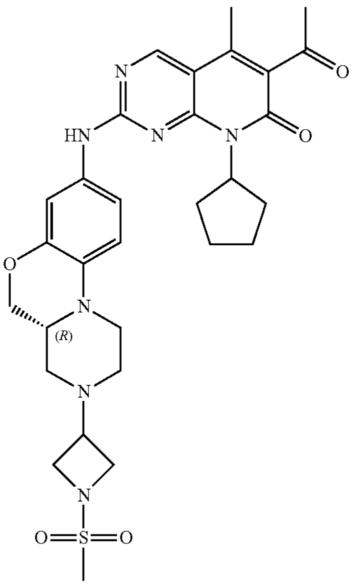

15S
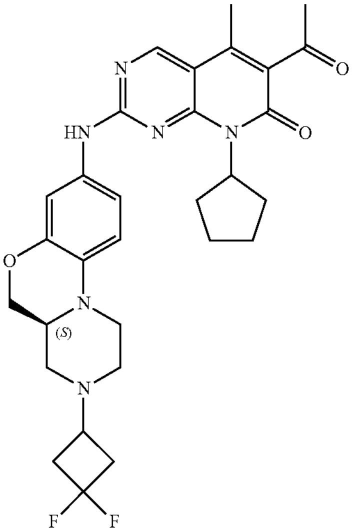
15R
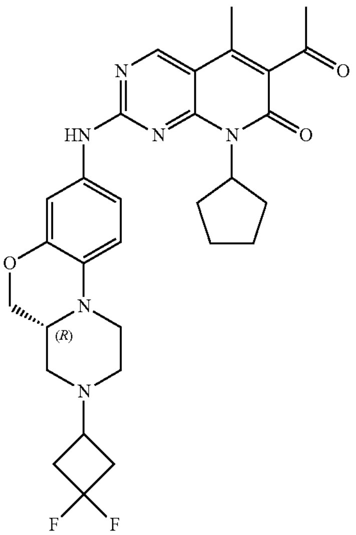
16S
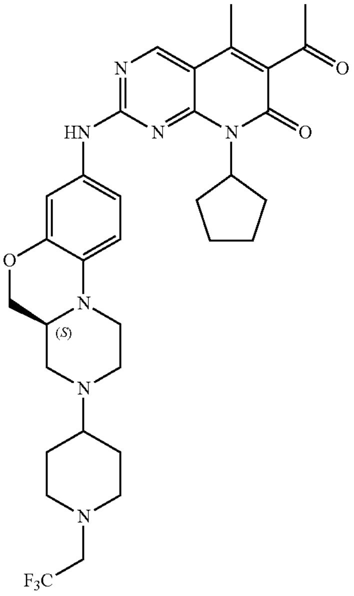
16R
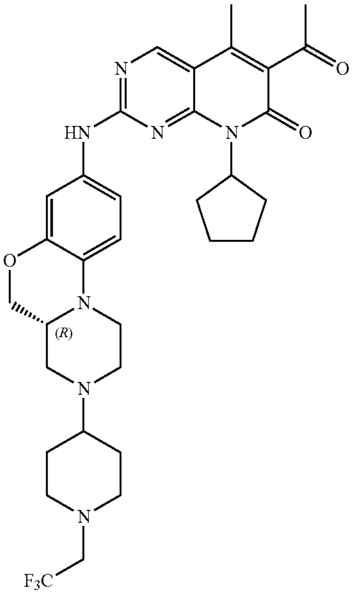
17S
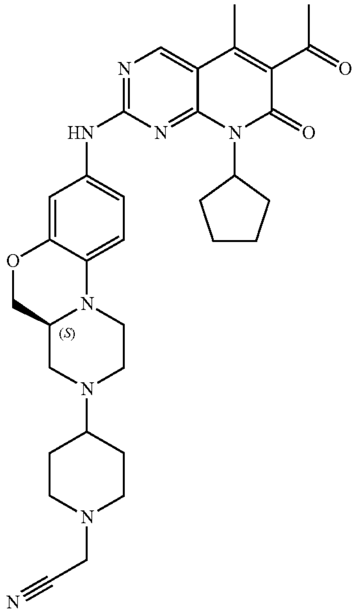

-continued
17R
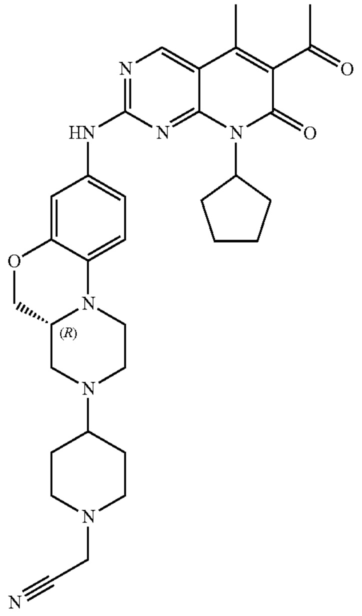
18S
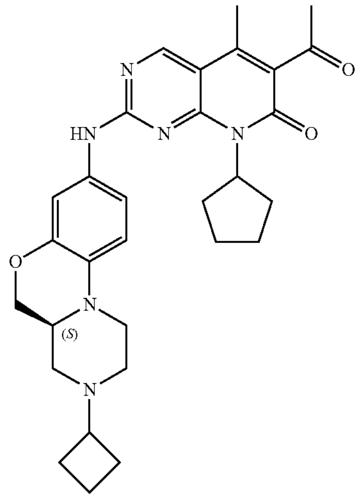
18R
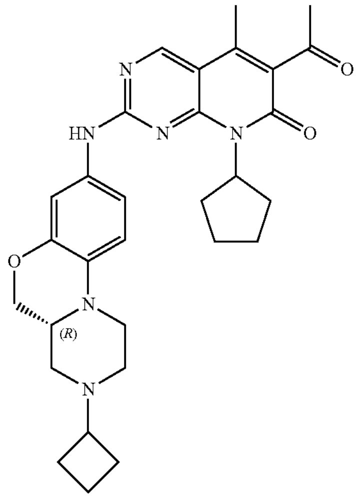
-continued
19S
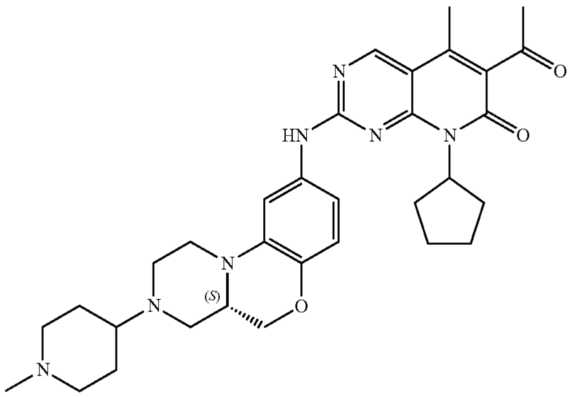
19R
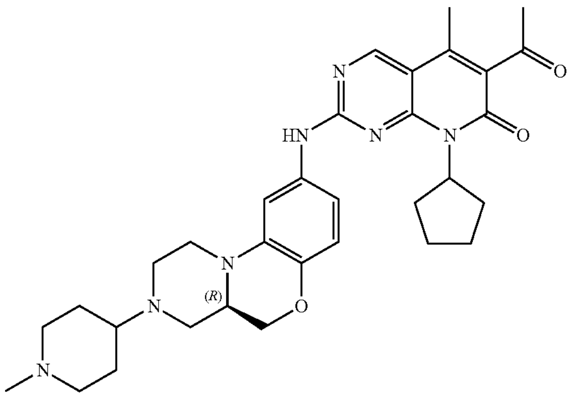
20S
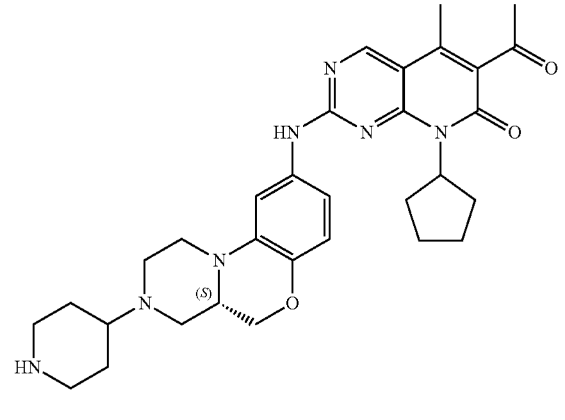

-continued
20R
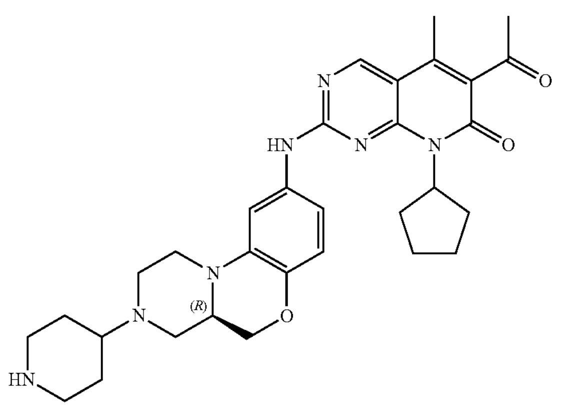
21S
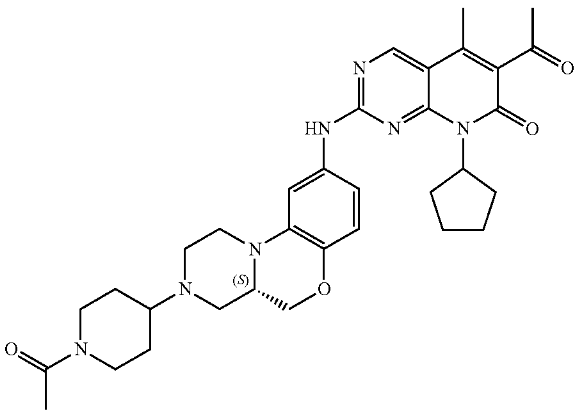
21R
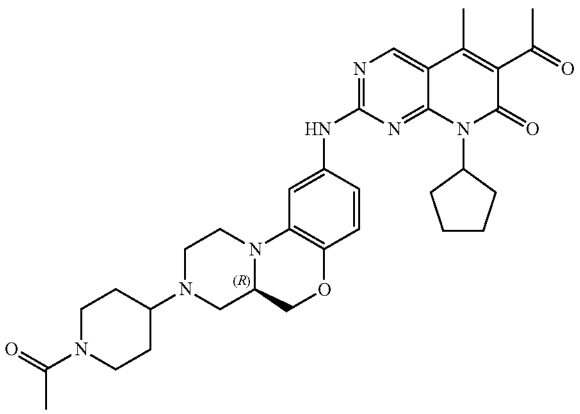
-continued
22S
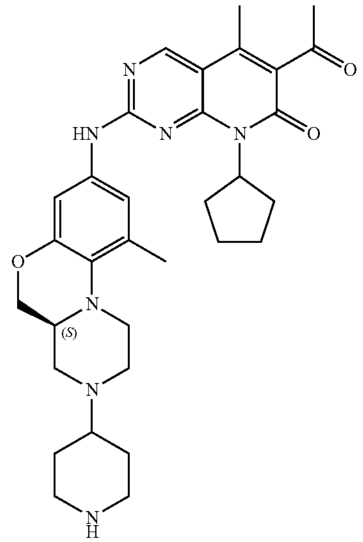
22R
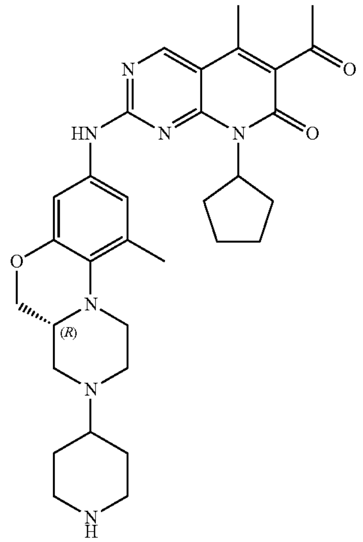

-continued
23S
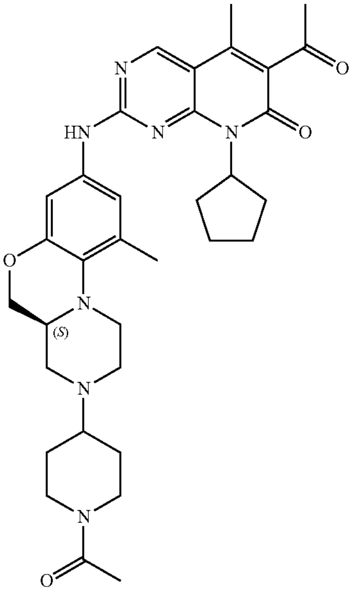
23R
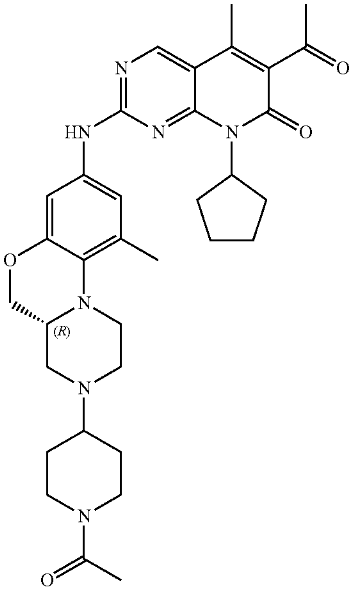
-continued
24S
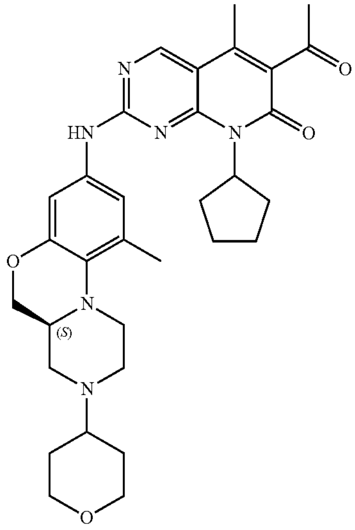
24R
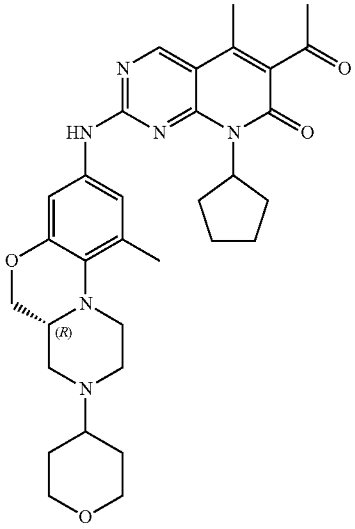
25S
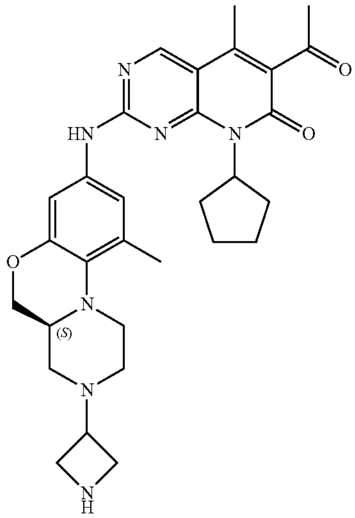

-continued
25R
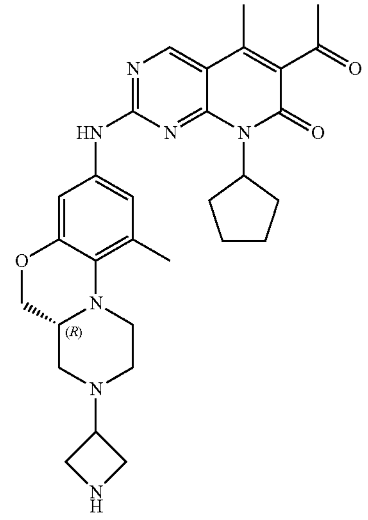
26S
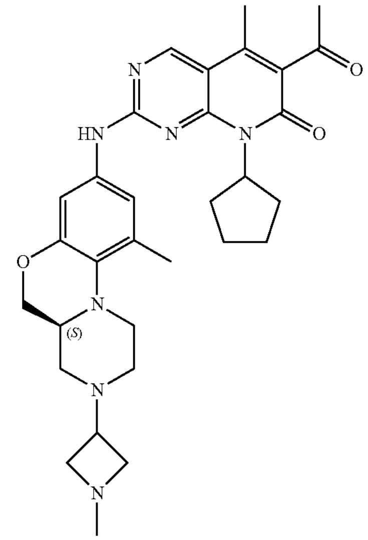
26R
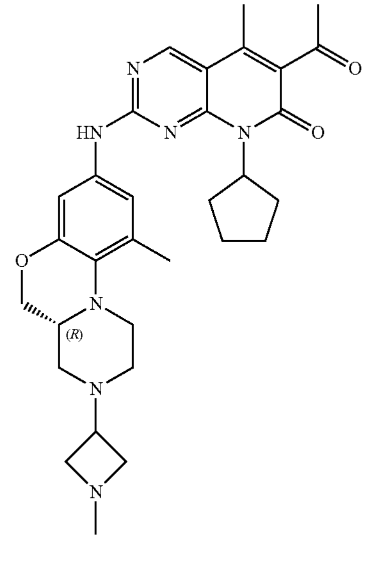
-continued
27S
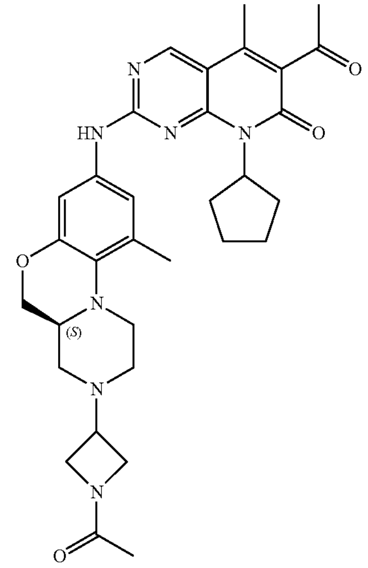
27R
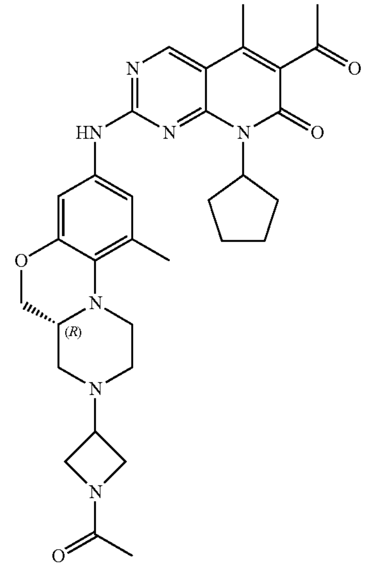
28S
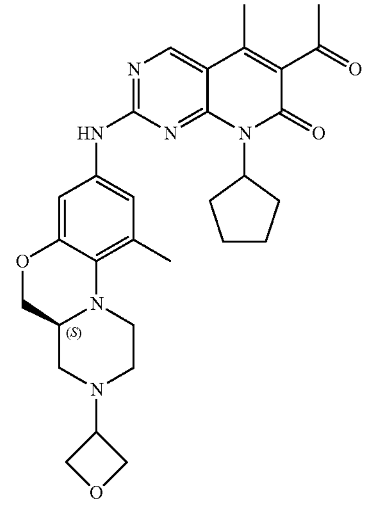

28R
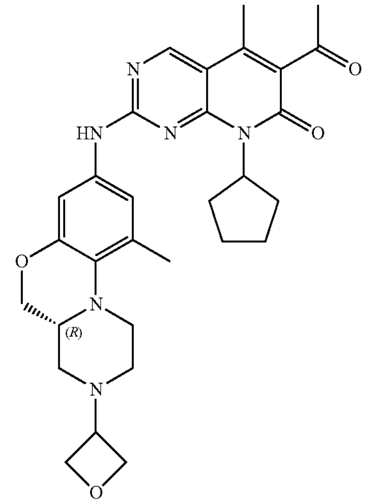
29S
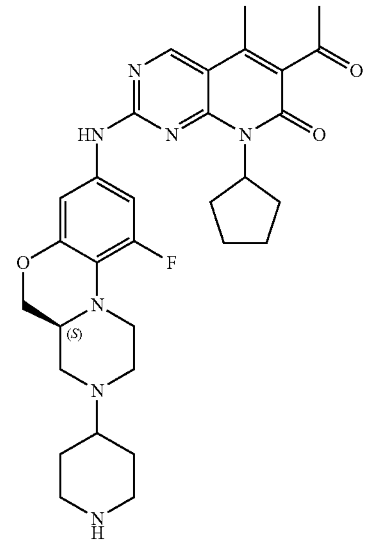
29R
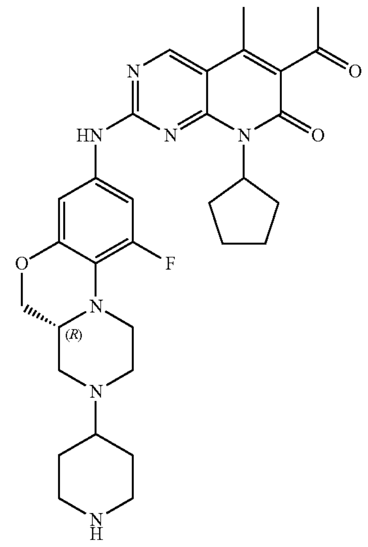
30S
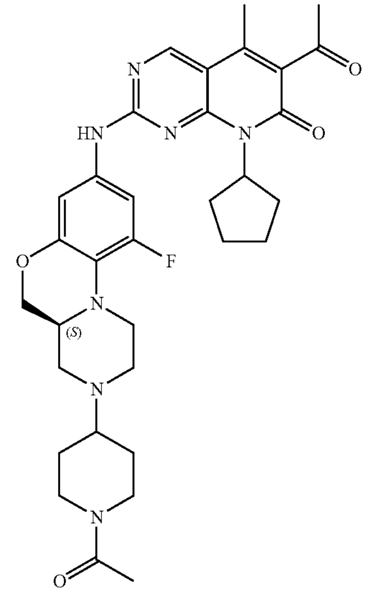
30R
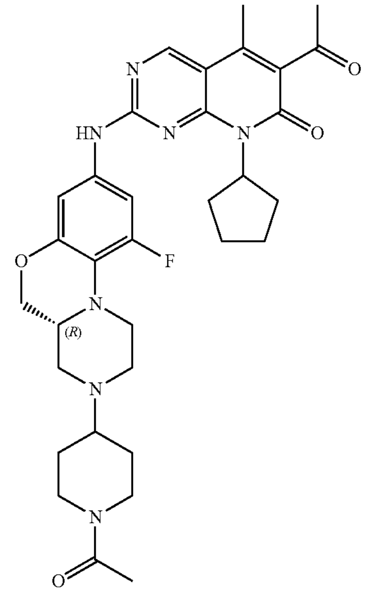

-continued
31S
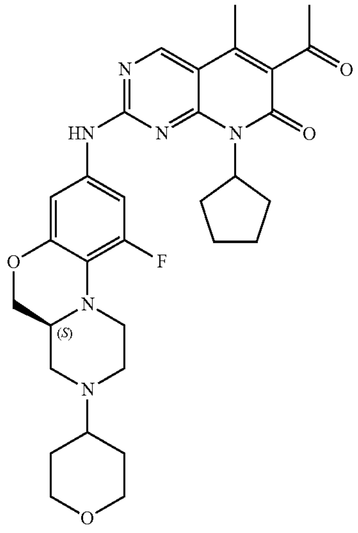
31R
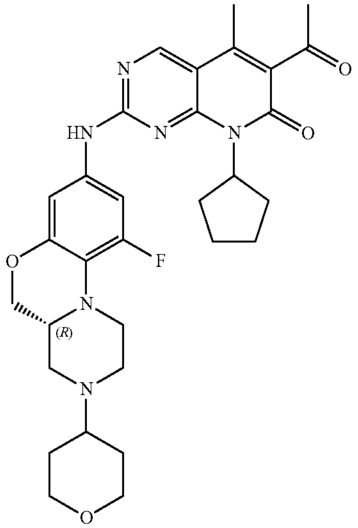
32S
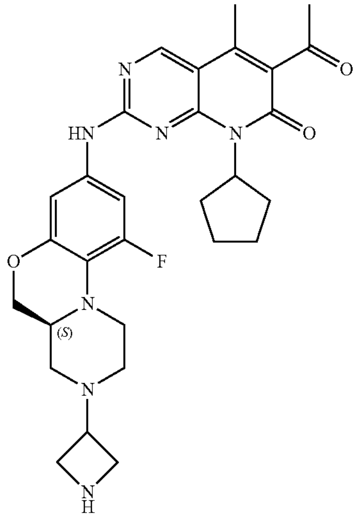
-continued
32R
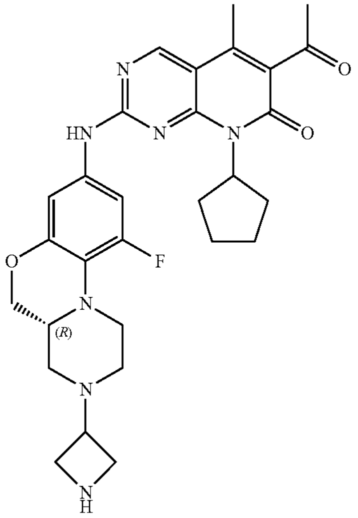
33S
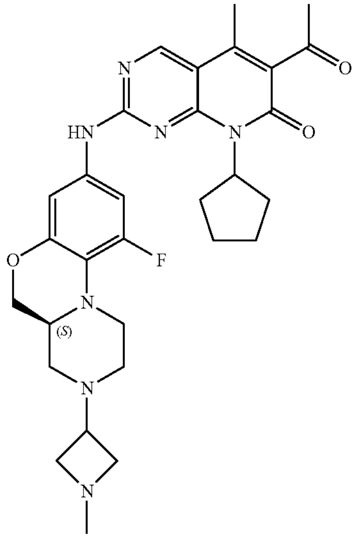
33R
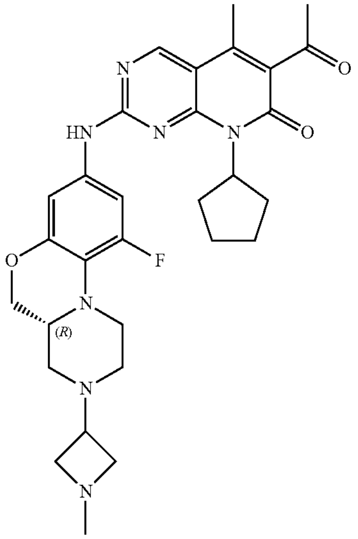

-continued
34S
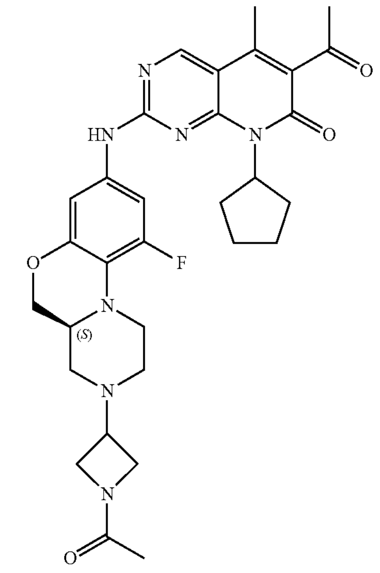
34R
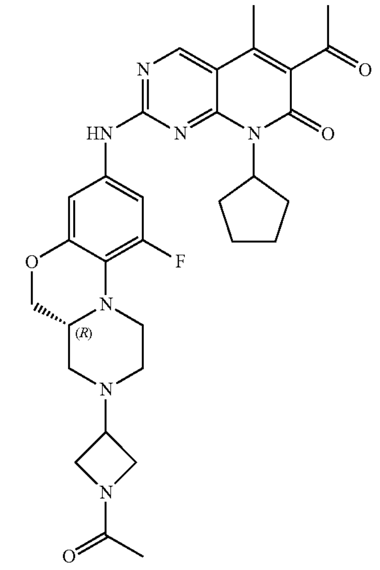
35S
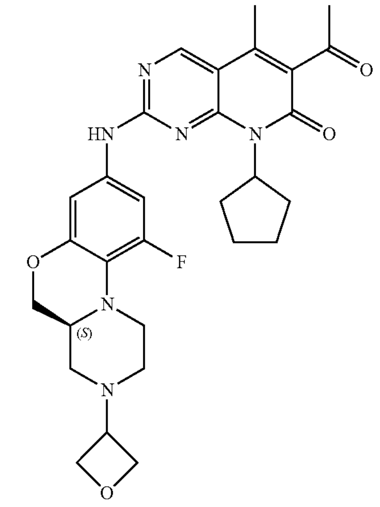
-continued
35R
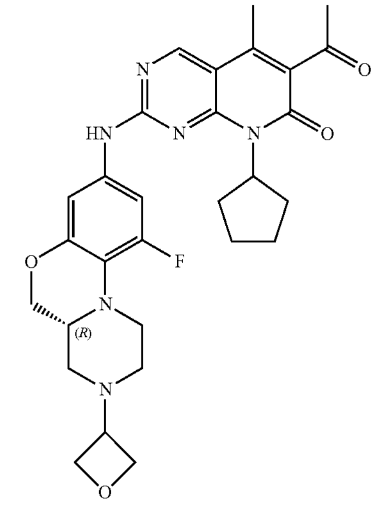
36S
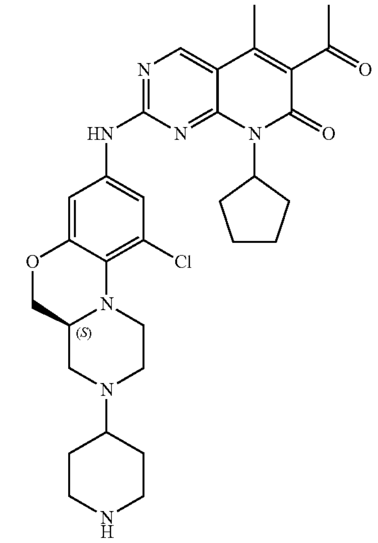
36R
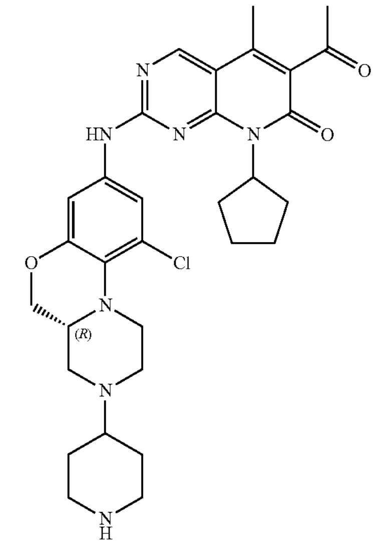

-continued
37S
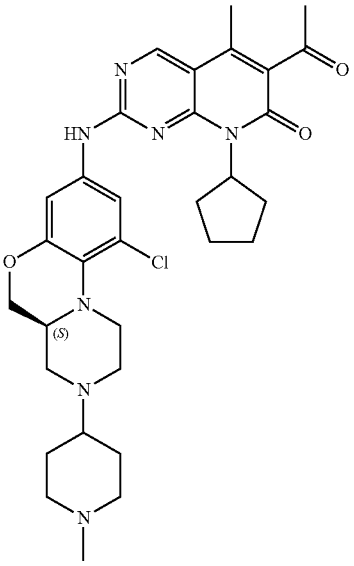
-continued
38S
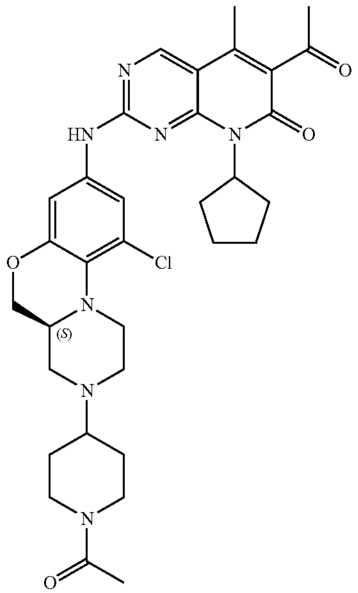
37R
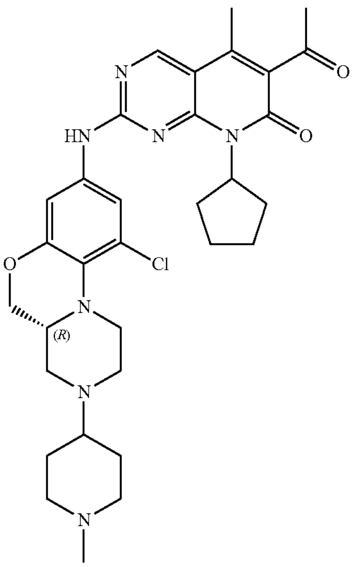
38R
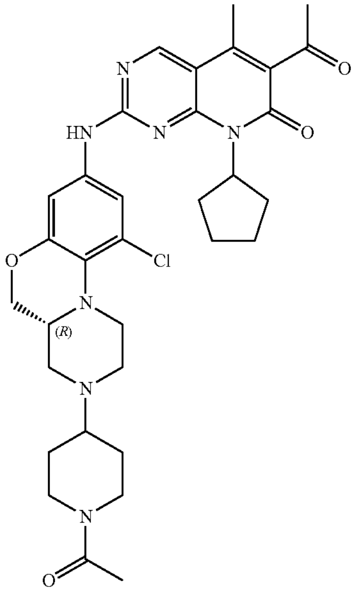

-continued
39S
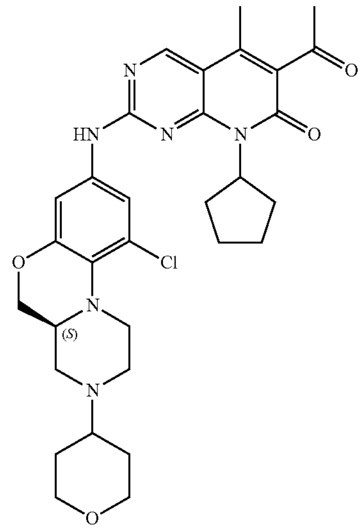
39R
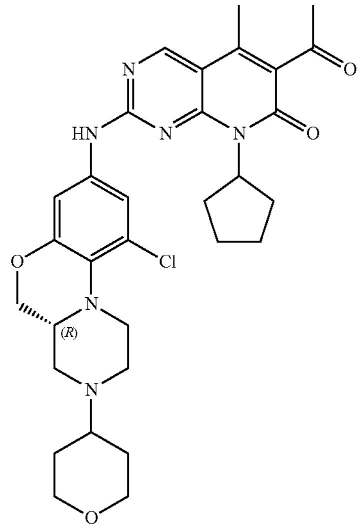
40S
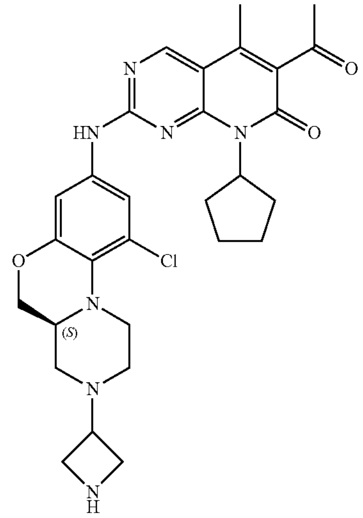
-continued
40R
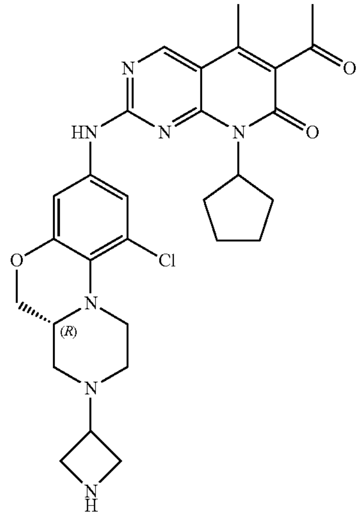
41S
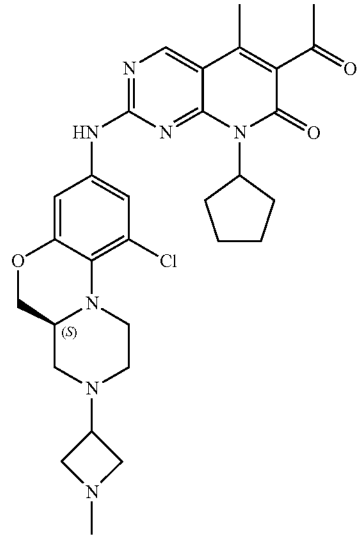
41R
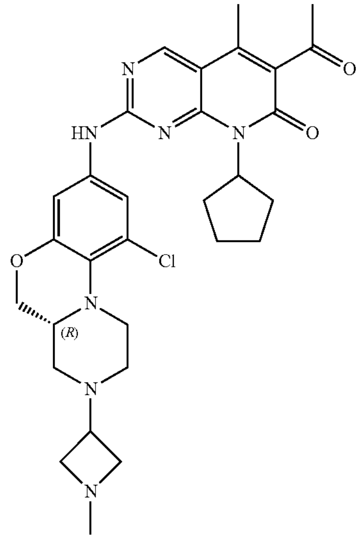

-continued

42S

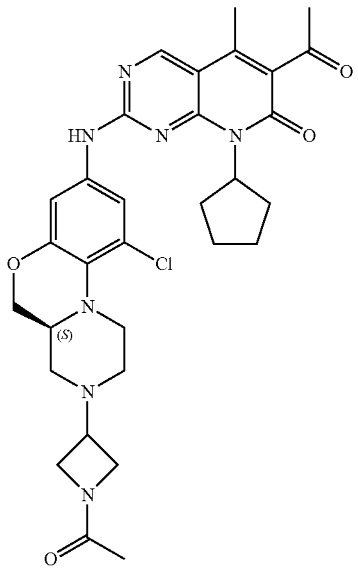

42R

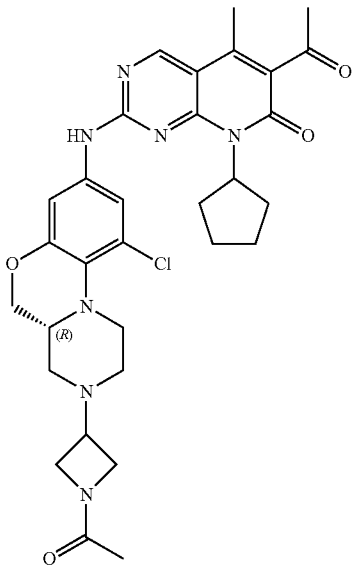

43S

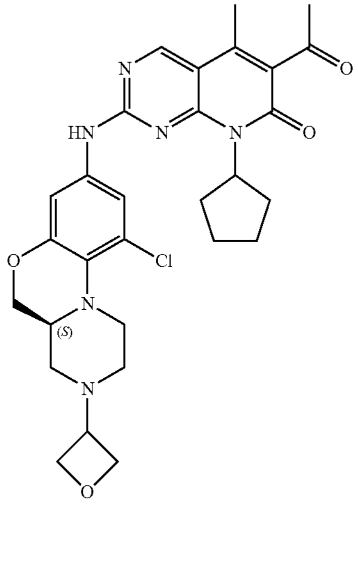

-continued

43R

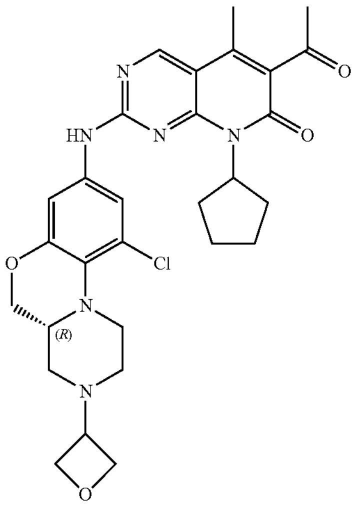

44S

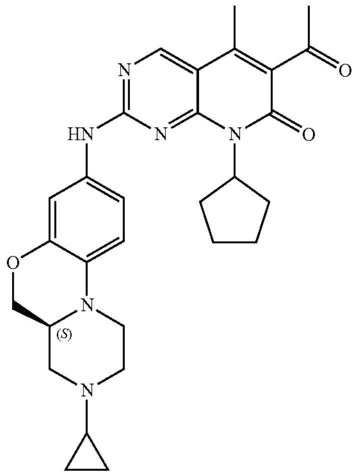

44R

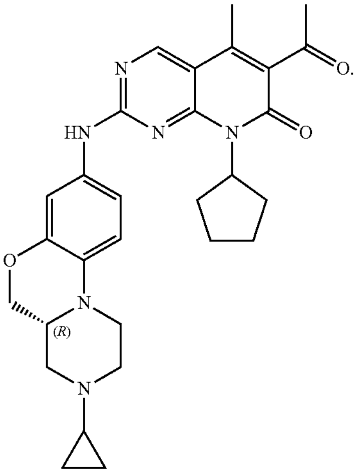

In another preferred embodiment, the salt is hydrochloride.

In the second aspect of the present invention, a pharmaceutical composition is provided, which comprising an effective amount of a compound described in the first aspect of the present invention, or the optical isomers, pharmaceutically acceptable salts, prodrugs, deuterated forms, hydrates or solvates thereof.

In another preferred embodiment, the pharmaceutical composition comprises: (i) therapeutically effective amount of formula (I) compound of the first aspect of the invention, or optical isomers, pharmaceutically acceptable salts, prodrugs, deuterated derivatives, hydrates, or solvates thereof, and (ii) pharmaceutically acceptable carrier.

In the third aspect of the present invention, a use of compound of formula (I) according to the first aspect of the invention, or optical isomers, pharmaceutically acceptable salts, prodrugs, deuterated derivatives, hydrates, or solvates thereof, or the pharmaceutical composition according to the second aspect of the invention is provided, wherein in:

(a) preparation of medicine for treating diseases associated with kinase activity or expression amount;

(b) preparation of kinase targeting inhibitor; and/or (c) in vitro non-therapeutic inhibiting of kinase activity;

wherein the kinase is selected from CDK and/or TRK.

In the fourth aspect of the invention, a use of the compounds of the first aspect of the invention, or their optical isomers, pharmaceutically acceptable salts, prodrugs, deuterated forms, hydrates or solvates thereof, or the pharmaceutical composition of the second aspect of the invention as kinase inhibitors, or for treating diseases which relates to high expression of the kinase is provided; wherein the kinase is selected from the group consisting of CDK and/or TRK.

In the fifth aspect of the present invention, a method for inhibiting kinase activity is provided, which comprises the step: administering an inhibitory effective amount of formula I compound of the first aspect of the invention, or the optical isomers, pharmaceutically acceptable salts, prodrugs, deuterated forms, hydrates or solvates thereof, or the pharmaceutical composition of the second aspect of the invention to a subject in need thereof; wherein the kinase is selected from the group consisting of CDK and/or TRK.

In another preferred embodiment, the disease is selected from the group consisting of DNA and RNA viral infections, B-cell lymphoma, monocytic leukemia, polycythemia megalosplenica, eosinophilic leukocytosis syndrome, idiopathic thrombocytopenic purpura, systemic giant cell disease, hematological tumors, solid tumors, neurodegenerative disease.

In another preferred embodiment, the disease is selected from the group consisting of allergic asthma, myelofibrosis, rheumatoid arthritis, inflammatory pain, cancer pain, AIDS, herpes virus and influenza virus, secretory breast cancer, fibrosarcoma, salivary gland cancer, liver cancer, rectal cancer, bladder cancer, pharyngolaryngeal cancer, non-small cell lung cancer, small cell lung cancer, lung adenocarcinoma, lung squamous cell carcinoma, breast cancer, prostate cancer, neurogliocytoma, ovarian cancer, head and neck squamous cell carcinoma, cervical cancer, esophageal cancer, kidney cancer, pancreas cancer, colon cancer, skin cancer, lymphoma, stomach cancer, multiple myeloma, brain tumor, lung cancer, Alzheimer's disease, Parkinson's disease.

In the sixth aspect of the present invention, the preparation method of compound of the first aspect of the present invention is provided, which comprises the following steps:

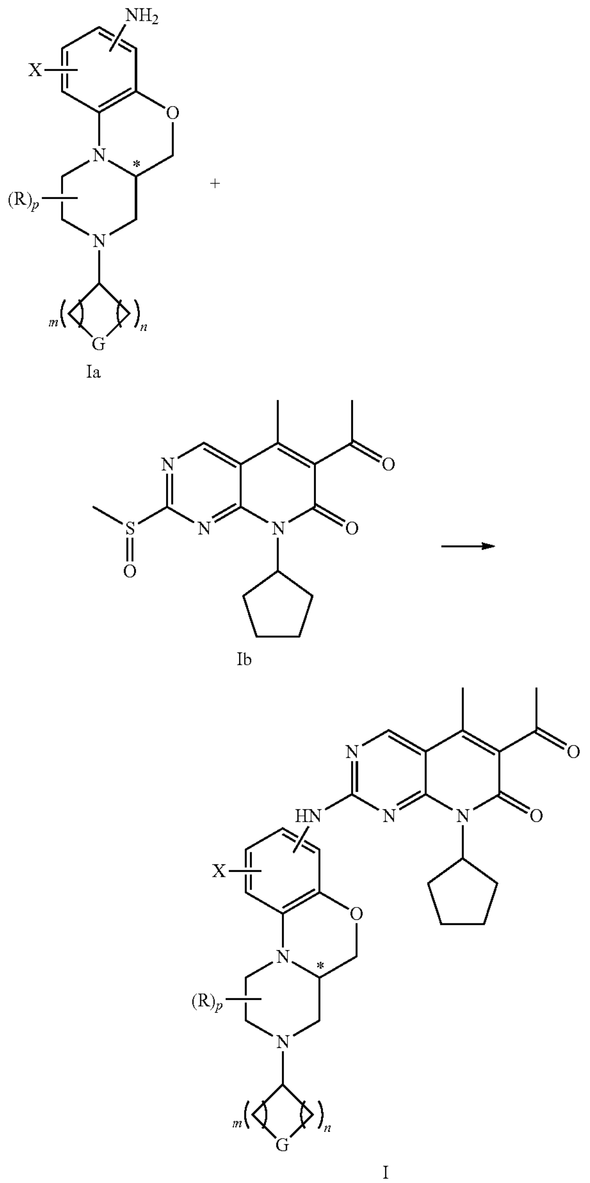

Ia

Ib

I in an inert solvent, the reaction of formula Ia compound and formula Ib compound yields formula I compound.

In another preferred embodiment, the method further comprises the steps:

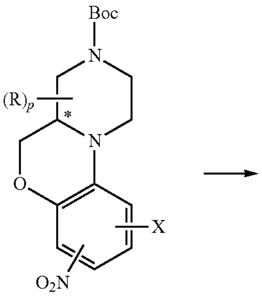

1-A3

-continued

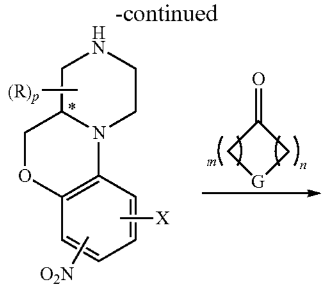

1-A3-a

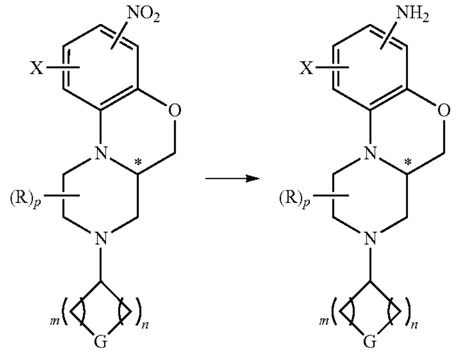

1-A4 Ia (1) in an inert solvent, deprotecting the compound of formula 1-A3 to give a compound of formula 1-A3-a;

(2) in an inert solvent, subjecting compound of formula 1-A3-a to reductive amination reaction with compound of formula 1-A3-b to obtain compound of formula 1-A4;

(i) in an inert solvent, reducing formula 1-A4 compound so as to provide formula Ia compound.

It is to be understood that within the scope of the present invention, the various technical features of the present invention and the various technical features specifically described hereinafter (as in the embodiments) may be combined with each other to form a new or preferred technical solution. Due to space limitations, we will not repeat them here.

Detail Implementation

After long-term and intensive research, the present inventors have unexpectedly discovered a novel class of polycyclic compounds as protein kinase inhibitors, as well as their preparation methods and applications. The compounds of the invention may be applied to the treatment of various diseases associated with the activity of kinases, including CDK and TRK. Based on the above findings, the inventors completed the present invention.

Terminology

Unless otherwise stated, "or" as used herein has the same meaning as "and/or" (refers to "or" and "and").

Unless otherwise specified, among all compounds of the present invention, each chiral carbon atom (chiral center) may optionally be in the R configuration or the S configuration, or a mixture of the R configuration and the S configuration.

As used herein, the term "alkyl", alone or as part of another substituent, refers to a straight (ie, unbranched) or branched saturated hydrocarbon group containing only carbon atoms, or a combination of straight and branched chains. When the alkyl group has a carbon number limitation (e.g., $C_{1-10}$), it means that the alkyl group has 1 to 10 carbon atoms. For example, $C_{1-8}$ alkyl refers to an alkyl group containing from 1 to 8 carbon atoms, including methyl, ethyl, propyl, isopropyl, butyl, isobutyl, sec-butyl, tert-butyl, or the like.

As used herein, the term "alkenyl", when used alone or as part of another substituent, refers to a straight or branched, carbon chain group having at least one carbon-carbon double bond. Alkenyl groups can be substituted or unsubstituted. When the alkenyl group has a carbon number limit (e.g., $C_{2-8}$), it means that the alkenyl group has 2-8 carbon atoms. For example, $C_{2-8}$ alkenyl refers to alkenyl groups having 2-8 carbon atoms, including ethenyl, propenyl, 1,2-butenyl, 2,3-butenyl, butadienyl, or the like.

As used herein, the term "alkynyl", when used alone or as part of another substituent, refers to an aliphatic hydrocarbon group having at least one carbon-carbon triple bond. The alkynyl group can be straight or branched, or a combination thereof. When the alkynyl group has a carbon number limitation (e.g., $C_{2-8}$ alkynyl group), it means that the alkynyl group has 2 to 8 carbon atoms. For example, the term "$C_{2-8}$ alkynyl" refers to a straight or branched alkynyl group having 2-8 carbon atoms, including ethynyl, propynyl, isopropynyl, butynyl, isobutynyl, secondary Butynyl, tert-butynyl, or the like.

As used herein, when used alone or as part of another substituent, the term "cycloalkyl" refers to a group having a saturated or partially saturated ring, a bicyclic or polycyclic (fused ring, bridged or spiro) ring system. When a certain cycloalkyl group has a carbon number limitation (e.g., $C_{3-10}$), it means that the cycloalkyl group has 3 to 10 carbon atoms. In some preferred embodiments, the term "C3-8 cycloalkyl" refers to a saturated or partially saturated monocyclic or bicyclic alkyl group having from 3 to 8 carbon atoms, including cyclopropyl, cyclobutyl, cyclopentyl, cycloheptyl, or the like. "Spirocycloalkyl" refers to a bicyclic or polycyclic group that shares a carbon atom (called a spiro atom) between the monocyclic rings. These may contain one or more double bonds, but none of the rings have fully conjugated π electrons system. "Fused cycloalkyl" refers to an all-carbon bi-cyclic or polycyclic group in which each ring share two neighboring carbon atoms with other ring(s), which may contain one or more double bonds, but none of the rings have a fully conjugated π-electron system. "Bridge cycloalkyl" refers to an all-carbon polycyclic group in which two rings share two carbon atoms that are not directly bonded, which may contain one or more double bonds, but none of the rings have a fully conjugated π-electron system. The atoms contained in the cycloalkyl group are all carbon atoms. Some examples of cycloalkyl groups are as follows, and the present invention is not limited to the following cycloalkyl groups.

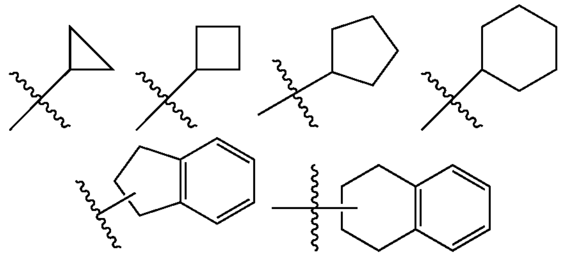

-continued

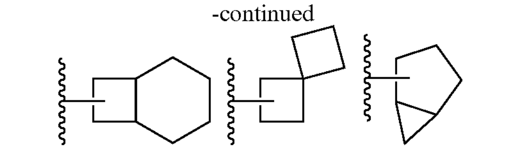

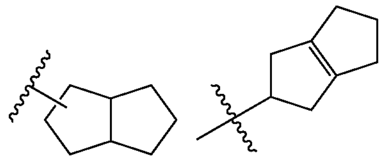

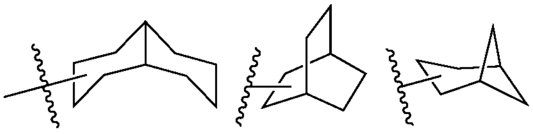

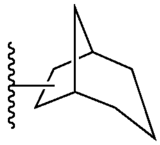

Unless otherwise stated, the following terms used in the specification and claims have the following meanings. "Aryl" means an all-carbon monocyclic or fused polycyclic (ie, a ring that shares a pair of adjacent carbon atoms) groups having a conjugated π-electron system, such as phenyl and naphthyl. The aryl ring may be fused to other cyclic groups (including saturated and unsaturated rings), hut may not contain heteroatoms such as nitrogen, oxygen, or sulfur, while the point of attachment to the parent must be on the carbon atoms of the ring in a conjugated π-electron system. The aryl group can be substituted or unsubstituted. The following are some examples of aryl groups, and the present invention is not limited to the aryl groups described below.

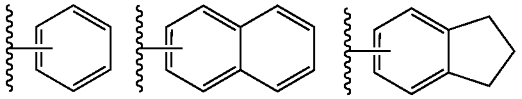

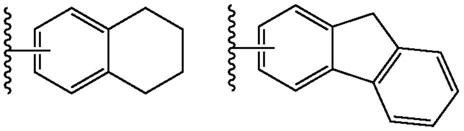

"Heteroaryl" refers to an aromatic monocyclic or polycyclic group containing one to more heteroatoms (optionally from nitrogen, oxygen, and sulfur), or a polycyclic group formed by condensing a heterocyclic group (containing one to more heteroatoms, optionally selected from nitrogen, oxygen, and sulfur) with an aryl group, and the attachment site is located on the aryl group. The heteroaryl group can be optionally substituted or unsubstituted. The following are some examples of heteroaryl groups, and the present invention is not limited to the following heteroaryl groups.

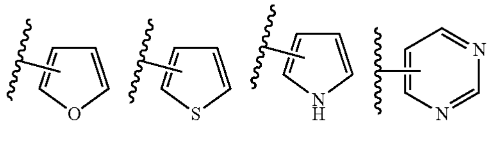

-continued

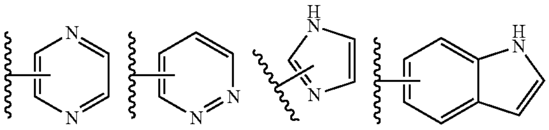

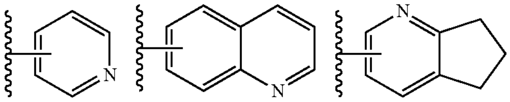

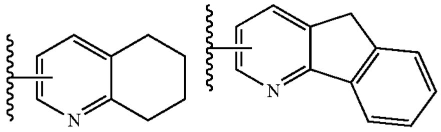

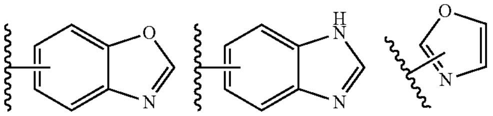

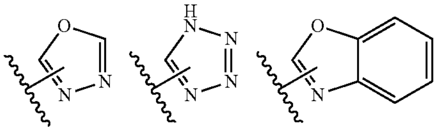

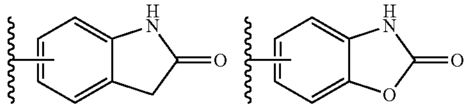

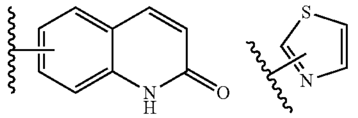

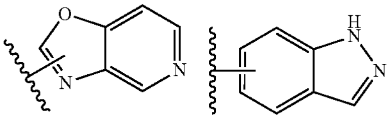

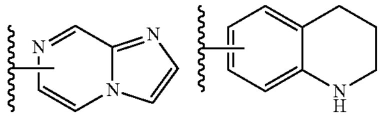

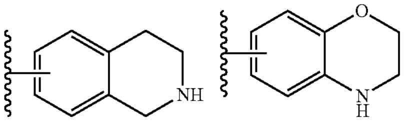

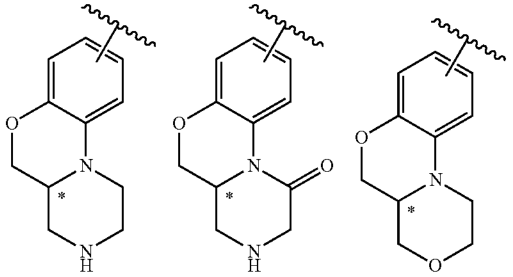

"Heterocyclyl" means a saturated or partially unsaturated monocyclic or polycyclic cyclic hydrocarbon substituent wherein one or more of the ring atoms are selected from nitrogen, oxygen or sulfur and the remaining ring atoms are carbon. Non-limiting examples of monocyclic heterocyclic groups include pyrrolidinyl, piperidinyl, piperazinyl, morpholinyl, thiomorpholinyl, homopiperazinyl. Polycyclic heterocyclic group refers to a heterocyclic group including a spiro ring, a fused ring, and a bridged ring. "Spirocyclic heterocyclyl" refers to a polycyclic heterocyclic group in which each ring of the system shares an atom (referred to as a spiro atom) with other rings in the system, wherein one or more of the ring atoms is selected from the group consisting of nitrogen and oxygen. Or sulfur, the remaining ring atoms are carbon, "Fused ring heterocyclyl" refers to a polycyclic heterocyclic group in which each ring of the system shares an adjacent pair of atoms with other rings in the system, and one or more rings may contain one or more double bonds, but none One ring has a fully conjugated pi-electron system, and wherein one or more ring atoms are selected from nitrogen, oxygen or sulfur, and the remaining ring atoms are carbon. "Bridged heterocyclyl" refers to a polycyclic heterocyclic group in which any two rings share two atoms which are not directly bonded, these may contain one or more double bonds, but none of the rings have a fully conjugated pi-electron system, and wherein one or more of the ring atoms are selected from nitrogen, oxygen or sulfur, and the remaining ring atoms are carbon. If a heterocyclic group has both a saturated ring and an aromatic ring (for example, the saturated ring and the aromatic ring are fused together), the point attached to the parent must be on the saturated ring. Note: When the point attached to the parent is on the aromatic ring, it is called a heteroaryl group and is not called a heterocyclic group. Some examples of the heterocyclic group are as follows, and the present invention is not limited to the following heterocyclic group.

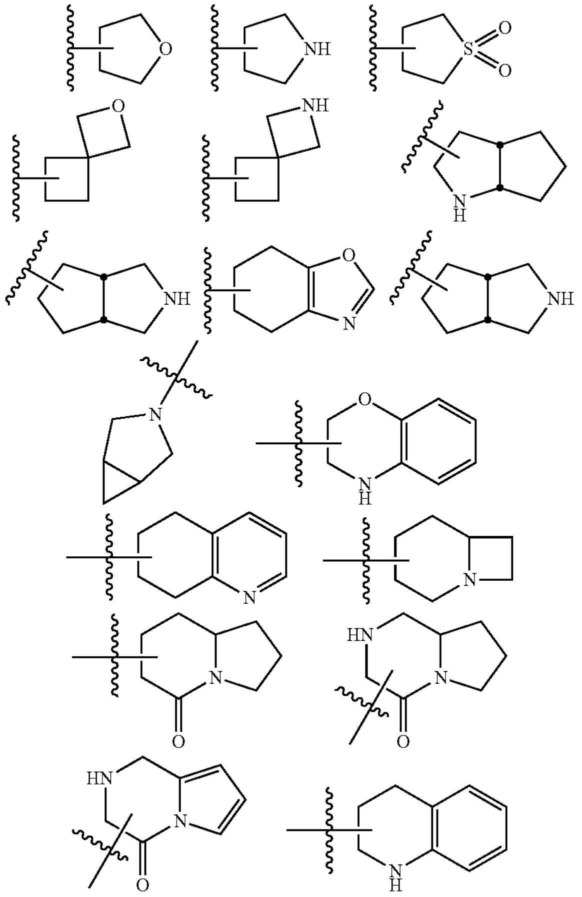

As used herein, the term "halogen" when used alone or as part of another substituent, refers to F, Cl, Br, and I.

As used herein, the term "substituted" (when with or without "optionally") means that one or more hydrogen atoms on a particular group are replaced by a particular substituent. Particular substituents are the substituents described above in the corresponding paragraphs, or the substituents which appear in the examples. Unless otherwise stated, an optionally substituted group may have a substituent selected from a particular group at any substitutable position of the group, and the substituents may be the same or different at each position. A cyclic substituent, such as a heterocyclic group, may be attached to another ring, such as a cycloalkyl group, to form a spirobicyclic ring system, i.e., the two rings have a common carbon atom. Those skilled in the art will appreciate that the combinations of substituents contemplated by the present invention are those that are stable or chemically achievable. The substituents are, for example but not limited to, $C_{1-8}$ alkyl, $C_{2-8}$ alkenyl, $C_{2-8}$ alkynyl, $C_{3-8}$ cycloalkyl, 3- to 12-membered heterocyclyl, aryl, heteroaryl, halogen, hydroxy, carboxy (—COOH), $C_{1-8}$ aldehyde, $C_{2-10}$ acyl, $C_{2-10}$ ester, amino group.

For convenience and in accordance with conventional understanding, the term "optionally substituted" or "optionally substituted" applies only to sites which are capable of being substituted by a substituent, and does not include those which are not chemically achievable.

As used herein, unless otherwise specified, the term "pharmaceutically acceptable salt" refers to a salt that is suitable for contact with the tissue of a subject (eg, a human) without causing unpleasant side effects. In some embodiments, a pharmaceutically acceptable salt of a compound of the invention includes a salt (eg, a potassium salt, a sodium salt, a magnesium salt, a calcium salt) of a compound of the invention having an acidic group or is basic A salt of a compound of the invention (e.g., a sulfate, a hydrochloride, a phosphate, a nitrate, a carbonate).

Application:

The present invention provides a class of compounds of formula (I), or their deuterated derivatives, their pharmaceutically acceptable salts, optical isomers (enantiomers or diastereomers, if any case), hydrates, solvates, or pharmaceutical combinations comprising the compound represented by formula (I), its optical isomers, pharmaceutically acceptable salts, prodrugs, deuterated forms, hydrates, and solvates for inhibiting kinase activity, wherein the kinase includes but not limited to CDK and/or TRK.

The compound of the present invention can be used as a kinase inhibitor. Preferably, the kinase is CDK and/or TRK.

In cancer patients, the expression or activity of various protein kinases mentioned above are significantly increased. These overexpressed and/or abnormal levels of protein kinase activity are directly related to the occurrence and development of tumors. The compounds of the present invention are single and/or dual inhibitors of these protein kinases. Diseases can be prevented, alleviated or cured by modulating the activity of these protein kinases. The diseases referred to include allergic asthma, myelofibrosis, rheumatoid arthritis, inflammatory pain, cancer pain, AIDS, DNA and RNA virus infections such as herpes virus and influenza virus, B-cell lymphoma, monocytic leukemia, Polycythemia splenomegaly, eosinophilic leukocytosis syndrome, essential thrombocytopenia, systemic giant cell disease, secretory breast cancer, fibrosarcoma, salivary gland cancer, liver cancer, rectal cancer, bladder cancer, throat cancer, non-small cell carcinoma Cell lung cancer, small cell lung cancer, lung adenocarcinoma, lung squamous cell carcinoma, breast cancer, prostate cancer, glioblastoma, ovarian cancer, head and neck squamous cell carcinoma, cervical cancer, esophageal cancer, kidney cancer, pancreatic cancer, colon cancer, skin cancer, lymphoma, gastric cancer, brain tumor, lung cancer, multiple myeloma and other hematological tumors and solid tumors, as well as neurodegenerative diseases such as Alzheimer's disease and Parkinson's disease.

From a certain point of view, multi-targeted kinase inhibitors interfere with several different kinases at the same time, and the anti-tumor effects produced are often additive [g2], so they have the potential to more effectively treat various cancers.

The compounds of the present invention can be used as combination drugs with other small molecule drugs or biological agents such as PD-1 inhibitors (eg Opdivo® and Keytruda®) to treat various cancers and related diseases.

The compounds of the present invention and their deuterated forms, as well as pharmaceutically acceptable salts or isomers (if present) or hydrates and/or compositions thereof can be combined with pharmaceutically acceptable excipients or carriers formulated together, the resulting composition can be administered to humans or animals for the treatment of disorders, symptoms and diseases. The composition can be: tablets, pills, suspensions, solutions, emulsions, capsules, aerosols, sterile injections, sterile powders and the like. In a preferred embodiment, the pharmaceutical composition is a dosage form suitable for oral administration, including but not limited to tablets, solutions, suspensions, capsules, granules, and powders. The amount of the compound or pharmaceutical composition administered to the patient is not fixed, and is usually administered in a pharmaceutically effective amount. At the same time, the amount of the compound actually administered can be determined by the physician according to the actual situation, including the disease to be treated, the route of administration selected, the actual compound administered, the individual condition of the patient, and so on. The dosage of the compound of the present invention depends on the specific use of the treatment, the mode of administration, the state of the patient, and the judgment of the physician. The ratio or concentration of the compound of the present invention in the pharmaceutical composition depends on a variety of factors, including dosage, physical and chemical properties, route of administration, and the like.

It is to be understood that within the scope of the present invention, the various technical features of the present invention and the various technical features specifically described hereinafter (as in the embodiments) may be combined with each other to form a new or preferred technical solution.

General Synthetic Schemes

The compound of formula I of the present invention can be prepared by the following method:

Scheme 1

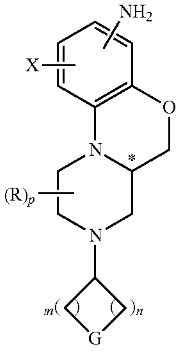

Ia

+

-continued

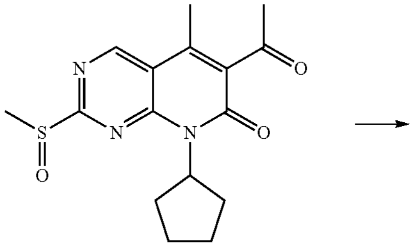

Ib

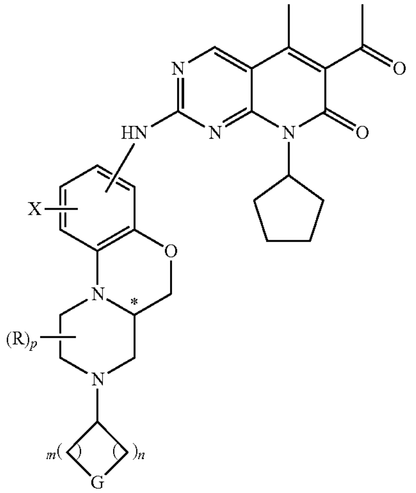

I

In an inert solvent, the compound (Ia) is reacted with the compound (Ib) to obtain the compound (I);

In the above formulas, the definition of each group is as described above. The reagents and conditions of each step can be selected from the conventional reagents or conditions of this type of preparation method in the art. After the structure of the compound of the present invention is disclosed, the above selection can be made by those skilled in the art according to the knowledge in the field.

More specifically, the compound represented by the general formula I of the present invention can be prepared by the following method, but the conditions of the method, such as reactants, solvent, base, amount of compound used, reaction temperature, reaction time required, etc. are not limited to the following explanation of. The compound s of the present invention can also be conveniently prepared by combining various synthetic methods described in this specification or known in the art, and such combinations can be easily performed by those skilled in the art to which the present invention belongs.

In the preparation method of the present invention, each reaction is usually carried out in an inert solvent, and the reaction temperature is usually −20 to 150° C. (preferably 0 to 120° C.). The reaction time of each step is usually 0.5 to 48 h, preferably 2~12 h.

Compound IIa and IIIa are part of compound I. Scheme 2 illustrates a general synthesis of compound IIa and IIIa:
Scheme 2
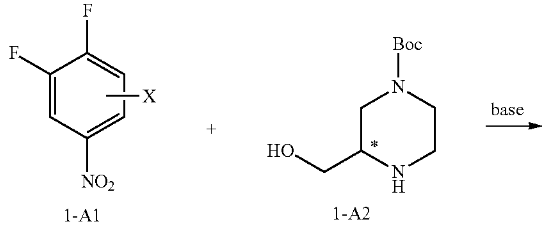
1-A1 1-A2
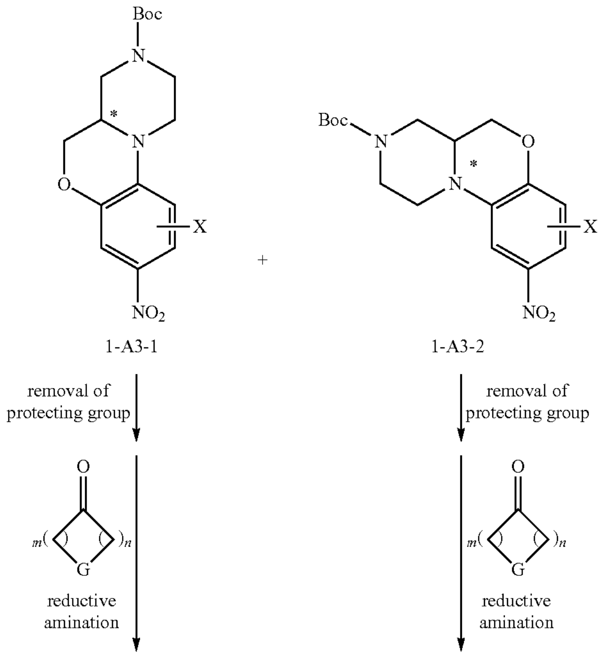
1-A3-1 1-A3-2

-continued

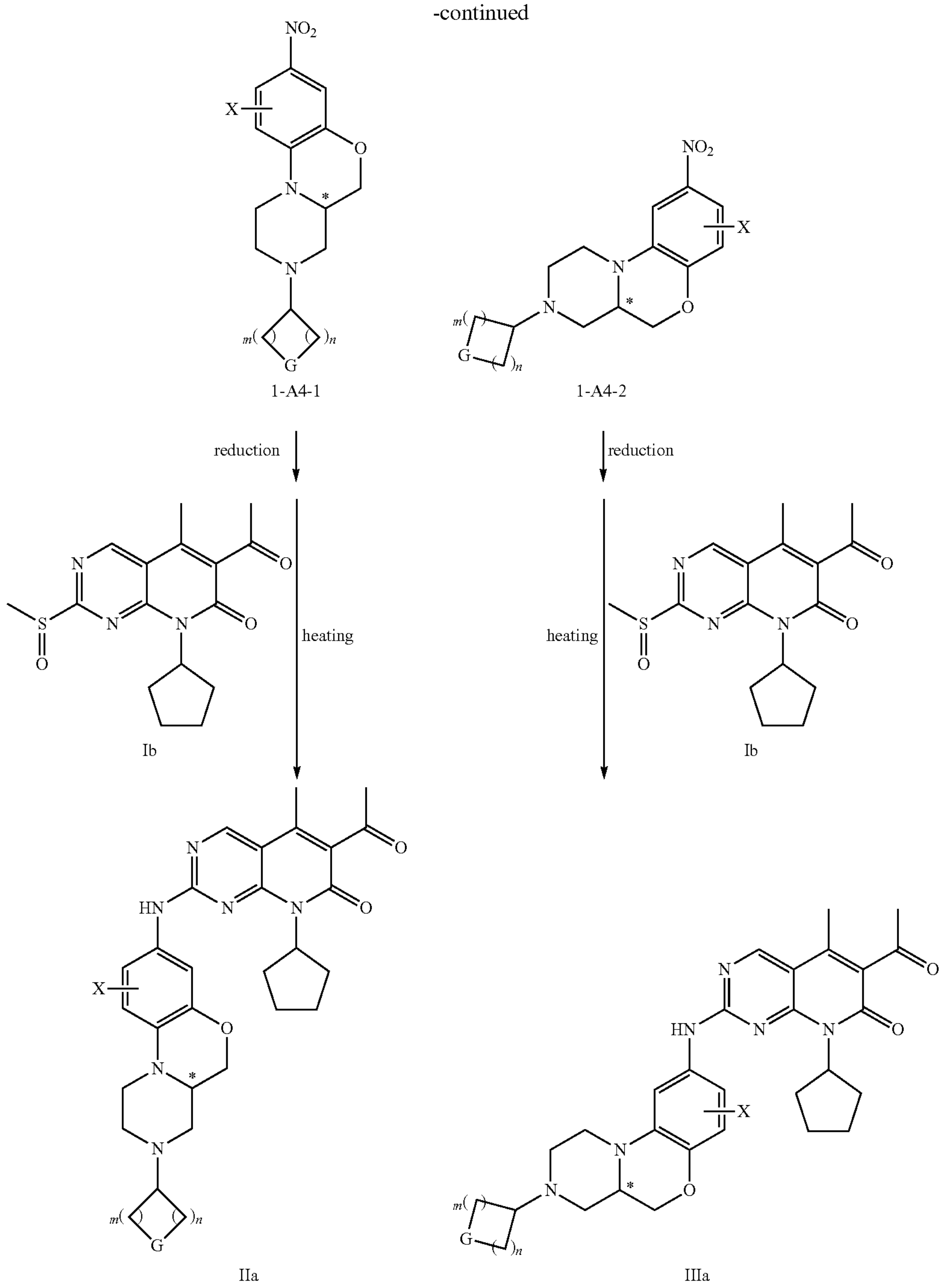

The definitions of X, R, G, m, n and p in the above schemes 1-2 are the same as those in Claim 1.

Intermediate Ib is prepared according to Journal of Medicinal Chemistry, 2005, 2371-2387 and the cited references.

Pharmaceutical Composition and Method of Administration

Since the compound of the present invention has excellent inhibitory activity against a series of protein kinases, the compound of the present invention and its various crystal forms, optical isomers, pharmaceutically acceptable inorganic or organic salts, prodrugs, deuterated forms, hydrates or solvates, and pharmaceutical compositions containing the compounds of the present invention as the main active ingredients can be used to treat, prevent and alleviate diseases associate with the activity or expression of CDK, TRK and other kinases.

The pharmaceutical compositions of the present invention comprise a safe or effective amount of a compound of the present invention, or a pharmaceutically acceptable salt thereof, and a pharmaceutically acceptable excipient or carrier. By "safe and effective amount" it is meant that the amount of the compound is sufficient to significantly improve the condition without causing serious side effects. In general, the pharmaceutical compositions contain from 1 to 2000 mg of the compound of the invention per agent, more preferably from 5 to 200 mg of the compound of the invention per agent. Preferably, the "one dose" is a capsule or tablet.

"Pharmaceutically acceptable carrier" means: one or more compatible solid or liquid fillers or get materials which are suitable for human use and which must be of sufficient purity and of sufficiently low toxicity. By "compatibility" it is meant herein that the components of the composition are capable of intermingling with the compounds of the invention and with each other without significantly reducing the efficacy of the compound. Examples of pharmaceutically acceptable carriers include, but are not limited to, filler (or diluent), disintegrant, lubricant, binder, matrix, emulsifiers, run wet agents, colorants, flavoring agents, stabilizers, antioxidants, preservatives, pyrogen-free water, and the like.

The mode of administration of the compound or pharmaceutical composition of the present invention is not particularly limited, and representative modes of administration include, but are not limited to, oral, intratumoral, rectal, parenteral (intravenous, intramuscular or subcutaneous), and topical administration.

Solid dosage forms for oral administration include capsules, tablets, pills, powders, and granules. In these solid dosage forms, the active compound is mixed with at least one conventional inert excipient (or carrier). In capsules, tablets and pills, the dosage form may also contain a buffer.

Solid dosage forms such as tablets, dragees, capsules, pills, and granules can be prepared with coatings and shells such as enteric coatings and other materials known in the art. They may contain opacifying agents and the release of the active compound or compound in such compositions may be released in a portion of the digestive tract in a delayed manner. Examples of embedding components that can be employed are polymeric and waxy materials. If necessary, the active compound may also be in microencapsulated form with one or more of the above-mentioned excipients.

In addition to these inert diluents, the compositions may contain adjuvants such as wetting agents, emulsifying and suspending agents, sweetening agents, flavoring agents and perfumes.

In addition to the active compound, the suspension may contain suspending agents.

Compositions for parenteral injection may comprise a physiologically acceptable sterile aqueous or nonaqueous solution, dispersion, suspension or emulsion, and a sterile powder for reconstitution into a sterile injectable solution or dispersion. Suitable aqueous and nonaqueous vehicles, diluents, solvents or vehicles include water, ethanol, polyols, and suitable mixtures thereof.

Dosage forms for the compounds of the invention for topical administration include ointments, powders, patches, propellants and inhalants. The active ingredient is admixed under sterile conditions with a physiologically acceptable carrier and any preservatives, buffers, or, if necessary, propellants. The compounds of the invention may be administered alone or in combination with other pharmaceutically acceptable compounds.

When a pharmaceutical composition is used, a safe and effective amount of a compound of the invention is administered to a mammal (e.g., a human) in need of treatment wherein the dosage is a pharmaceutically effective dosage, for a 60 kg body weight, The dose to be administered is usually from 1 to 2000 mg, preferably from 5 to 500 mg. Of course, specific doses should also consider factors such as the route of administration, the health of the patient, etc., which are within the skill of the skilled physician.

The main advantages of the invention include:

1. Provided a compound of formula I.

2. A novel structure of CDK, TRK (including CDK2, CDK4, CDK5, CDK6, CDK9, CDK16, TRKA, TRKB, and TRKC, etc.) inhibitors, and their preparation and use are provided. These inhibitors inhibit the activity of above protein kinases at very low concentrations, 3. A class of pharmaceutical compositions for treating diseases associated with CDK, TRK, etc. kinases activity is provided.

4. A kind of kinase inhibitors such as CDK and TRK with good oral absorbability is provided.

The invention is further illustrated below in conjunction with specific embodiments. It is to be understood that the examples are not intended to limit the scope of the invention. The experimental methods in the following examples which do not specify the specific conditions are usually in accordance with conventional conditions or according to the conditions recommended by the manufacturer. Percentages and parts are by weight unless otherwise stated.

EXAMPLE 1: PREPARATION OF COMPOUND 1S

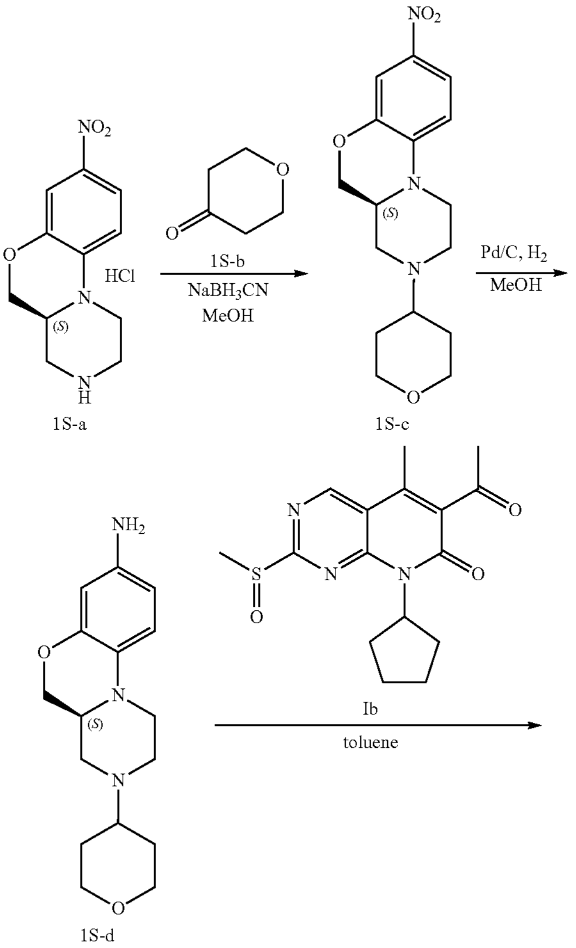

1S-a 1S-c 1S-d

-continued

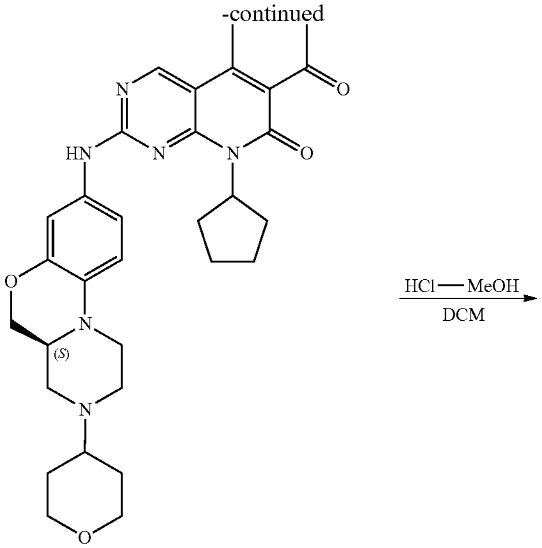

1S

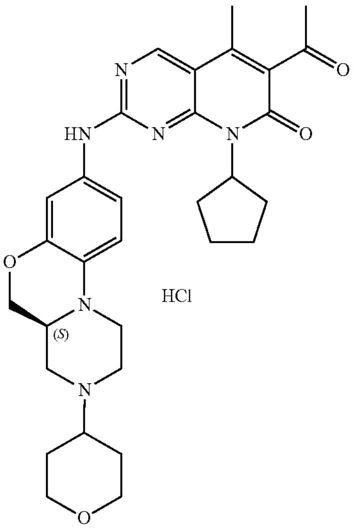

1S-HCl

Compound 1S-a (600 mg, 2.21 mmol) was dissolved in methanol (20 mL). Tetrahydropyranone (1S-b, 265 mg, 2.65 mmol) and triethylamine (224 mg, 2.21 mmol) were added. The reaction mixture was stirred at 50° C. for 2 hours. Sodium cyanoborohydride (208 mg, 3.31 mmol) was added at room temperature, and the reaction mixture was stirred for 3 hours. The reaction was monitored by TLC for completion. It was concentrated under reduced pressure to remove methanol. Water (10 mL) was added, and the resulted mixture was extracted with dichloromethane (3×20 mL). The combined organic layers were washed with brine, dried over anhydrous sodium sulfate, filtered, and concentrated under reduced pressure. The residue was purified in $SiO_2$ chromatography ($CH_2Cl_2$:EtOAc=1:1) to afford compound 1S-c (580 mg, yield 82%) as a yellow solid. MS m/z 320.4 $[M+H]^+$.

To a solution of compound 1S-c (580 mg, 1.82 mmol) in methanol (15 mL) was added Pd on carbon (10%, 70 mg). The reaction mixture was stirred at room temperature under 1 atmospheric pressure of $H_2$ for 3 hours. The reaction was monitored by TLC for completion. It was filtered through celite. The filtrate was concentrated under reduced pressure, and the residue was purified in $SiO_2$ chromatography ($CH_2Cl_2$:$CH_3OH$=50:1) to afford compound 1S-d (460 mg, yield 88%) as a brown solid. MS m/z 290.4 $[M+H]^+$.

Compound 1S-d (200 mg, 0.69 mmol) and compound Ib (230 mg, 0.69 mmol) were dissolved in toluene (6 mL). The reaction mixture was stirred at 90° C. for 3 hours. The reaction was monitored by TLC for completion. It was cooled to room temperature, and concentrated under reduced pressure. The residue was purified in $SiO_2$ chromatography ($CH_2Cl_2$:$CH_3OH$=80:1) to afford compound 1S (290 mg, yield 75%) as a yellow solid. MS m/z 559.8 $[M+H]^+$.

Compound 15 (290 mg, 0.52 mmol) was dissolved in dichloromethane (10 mL). A solution of HCl in methanol (4.0 M, 0.13 mL, 0.52 mmol) was added under ice bath. The reaction mixture was stirred at room temperature for 1 hour. It was concentrated under reduced pressure. Water (5 mL) was added, and the resulted mixture was dried by lyophilization to afford compound 1S HCl salt (290 mg) as a yellow solid. $^1H$ NMR (500 MHz, $CD_3OD$) δ 8.77 (s, 1H), 7.16 (s, 1H), 6.99 (s, 2H), 5.90-5.75 (m, 1H), 4.37 (dd, J=10.9, 2.4 Hz, 1H), 4.17 (d, J=13.2 Hz, 1H), 4.11-4.04 (m, 3H), 3.82-3.70 (m, 2H), 3.63-3.49 (m, 2H), 3.45 (t, J=11.5 Hz, 2H), 3.29-3.22 (m, 1H), 3.20-3.06 (m, 1H), 2.96 (t, J=11.8 Hz, 1H), 2.47 (s, 3H), 2.33 (s, 3H), 2.30-2.19 (m, 2H), 2.18-2.10 (m, 2H), 2.01-1.76 (m, 6H), 1.67-1.53 (m, 2H) ppm. MS m/z 559.8 $[M+H]^+$.

EXAMPLE 2: PREPARATION OF COMPOUND 2S

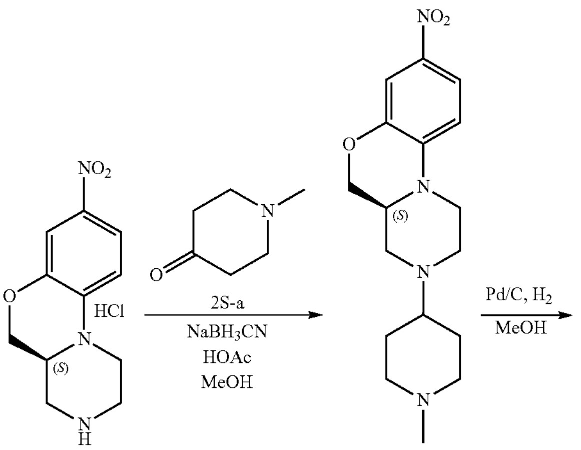

1S-a 2S-b

-continued

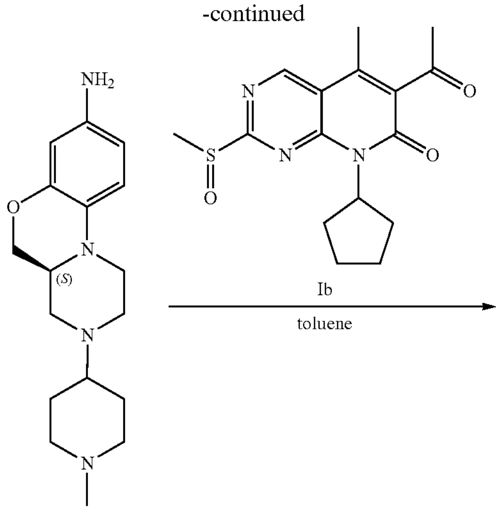

2S-c

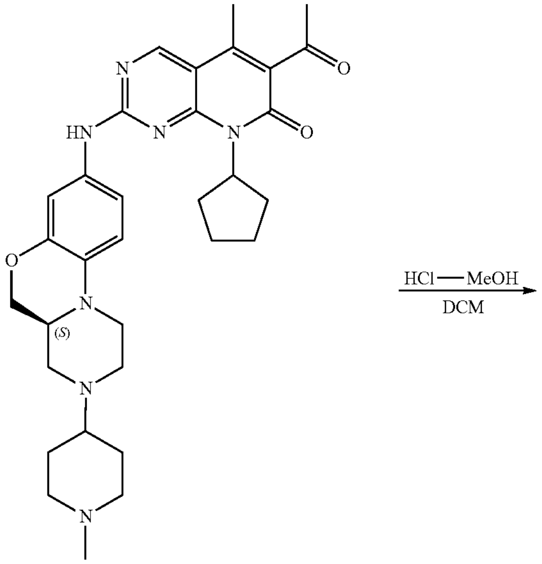

2S

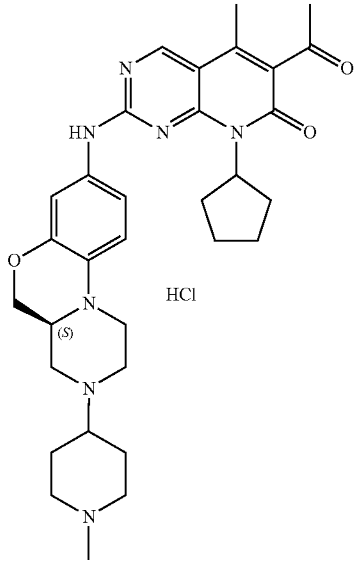

2S•HCl

To methanol (15 mL) was added compound 1S-a (500 mg, 1.84 mmol), N-methylpiperidone (2S-a, 416 mg, 3.68 mmol), and AcOH (2 drops). The reaction mixture was stirred at room temperature for 1 hour. Sodium cyanoborohydride (231 mg, 3.68 mmol) was added, and the reaction mixture was stirred at room temperature overnight. The reaction was monitored by TLC for completion. It was concentrated under reduced pressure to remove methanol. Water (10 mL) was added, and the mixture was extracted with dichloromethane (3×20 mL). The combined organic layers were washed with brine, dried over anhydrous sodium sulfate, filtered, and concentrated under reduced pressure. The residue was purified in $SiO_2$ chromatography ($CH_2Cl_2$:$CH_3OH$=30:1) to afford compound 2S-b (500 mg) as a yellow solid, which was used in next step.

To methanol (15 mL) was added compound 2S-b (500 mg, 1.50 mmol) and Pd on carbon (10%, 70 mg). The reaction mixture was stirred at room temperature under 1 atmospheric pressure of $H_2$ for 3 hours. The reaction was monitored by TLC for completion. It was filtered through celite, and the filtrate was concentrated under reduced pressure. The residue was purified in $SiO_2$ chromatography ($CH_2Cl_2$:$CH_3OH$=20:1) to afford compound 2S-c (280 mg, yield 62%) as a brown solid.

Compound 2S-c (280 mg, 0.93 mmol) and compound Ib (310 mg, 0.93 mmol) were dissolved in toluene (8 mL). The reaction mixture was stirred at 90° C. for 3 hours. The reaction was monitored by TLC for completion. It was cooled to room temperature, and concentrated under reduced pressure. The residue was purified in $SiO_2$ chromatography ($CH_2Cl_2$:$CH_3OH$=20:1) to afford compound 2S (180 mg, yield 34%) as a yellow solid. $^1$H NMR (500 MHz, DMSO-$d_6$) δ 9.86 (bs, 1H), 8.90 (s, 1H), 7.16 (d, J=2.1 Hz, 1H), 7.06 (d, J=8.9 Hz, 1H), 6.81 (d, J=8.9 Hz, 1H), 5.91-5.70 (m, 1H), 4.23 (dd, J=10.5, 2.4 Hz, 1H), 3.89 (dd, J=10.5, 9.0 Hz, 1H), 3.69 (d, J=11.3 Hz, 1H), 3.00-2.88 (m, 3H), 2.79 (d, J=11.2 Hz, 2H), 2.59-2.53 (m, 1H), 2.41 (s, 3H), 2.34-2.16 (m, 7H), 2.14 (s, 3H), 1.94-1.73 (m, 9H), 1.62-1.51 (m, 2H), 1.48-1.36 (m, 2H) ppm. MS m/z 572.8 $[M+H]^+$.

Compound 2S (180 mg, 0.31 mmol) was dissolved in dichloromethane (10 mL). A solution of HCl in methanol (4.0 M, 0.08 mL, 0.32 mmol) was added under ice bath. The reaction mixture was stirred at room temperature for 1 hour. It was concentrated under reduced pressure. Water (5 mL) was added, and the resulted mixture was dried by lyophilization to afford compound 2S HCl salt (185 mg) as a yellow solid. $^1$H NMR (500 MHz, $CD_3OD$) δ 8.79 (s, 1H), 7.21 (s, 1H), 7.05-6.97 (m, 2H), 5.92-5.80 (m, 1H), 4.42-4.35 (m, 1H), 4.19 (d, J=13.0 Hz, 1H), 4.11-4.07 (m, 1H), 3.81-3.71 (m, 4H), 3.68-3.54 (m, 2H), 3.21-3.11 (m, 4H), 3.06-3.00 (m, 1H), 2.92 (s, 3H), 2.58-2.50 (m, 2H), 2.47 (s, 3H), 2.34 (s, 3H), 2.32-2.23 (m, 2H), 2.22-2.11 (m, 2H), 1.98-1.77 (m, 4H), 1.67-1.56 (m, 2H) ppm. MS m/z 572.8 $[M+H]^+$.

EXAMPLE 3: PREPARATION OF COMPOUND 2R

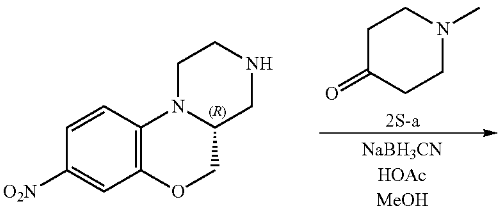

2R-a

-continued

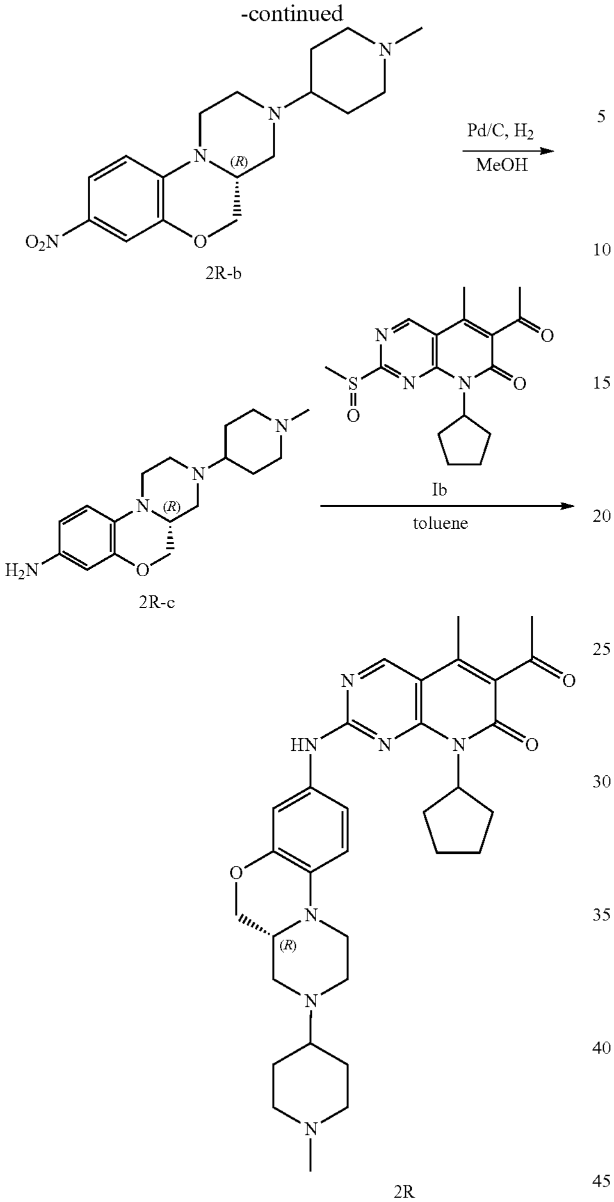

2R-b 2R-c

2R

A mixture of compound 2R-a (100 mg, 0.43 mmol), N-methyl-4-piperidone (2S-a, 144 mg, 1.28 mmol), and AcOH (2 drops) in methanol (6 mL) was stirred at room temperature for 1 hour. Sodium cyanoborohydride (80 mg, 1.28 mmol) was added, and the reaction mixture was stirred at room temperature overnight. The reaction was monitored by TLC for completion. It was concentrated under reduced pressure, and the residue was purified in $SiO_2$ chromatography ($CH_2Cl_2$:$CH_3OH$=20:1, 2% aqueous ammonium hydroxide solution) to afford compound 2R-b (200 mg) as a yellow solid, which was used in next step. MS m/z 333.5 $[M+H]^+$.

To methanol (6 mL) at room temperature was added compound 2R-b (200 mg, 0.60 mmol) and Pd on carbon (10%, 80 mg). The reaction mixture was stirred at room temperature under 1 atmospheric pressure of $H_2$ for 1 hour. The reaction was monitored by TLC for completion. It was filtered through celite, and the filtrate was concentrated under reduced pressure. The residue was purified in $SiO_2$ chromatography ($CH_2Cl_2$:$CH_3OH$=20:1, 2% aqueous ammonium hydroxide solution) to afford compound 2R-c (93 mg, yield of two steps 72%) as a yellow oil. MS m/z 303.5 $[M+H]^+$.

A mixture of compound 2R-c (50 mg, 0.17 mmol) and compound Ib (55 mg, 0.17 mmol) in toluene (1 mL) in a sealed tube was heated to 100° C., and stirred overnight. The reaction was monitored by TLC for completion. It was cooled to room temperature, and concentrated under reduced pressure. The residue was purified in $SiO_2$ chromatography ($CH_2Cl_2$:$CH_3OH$=20:1) to afford compound 2R (43 mg, yield 45%) as a yellow solid. $^1H$ NMR (500 MHz, DMSO-$d_6$) δ 9.87 (bs, 1H), 8.90 (s, 1H), 7.16 (d, J=2.0 Hz, 1H), 7.06 (d, J=8.0 Hz, 1H), 6.81 (d, J=8.9 Hz, 1H), 5.91-5.70 (m, 1H), 4.23 (dd, J=10.5, 2.4 Hz, 1H), 3.89 (dd, J=10.4, 9.1 Hz, 1H), 3.69 (d, J=11.3 Hz, 1H), 3.02-2.89 (m, 3H), 2.80 (d, J=11.0 Hz, 2H), 2.58-2.51 (m, 1H), 2.41 (s, 3H), 2.34-2.15 (m, 7H), 2.14 (s, 3H), 1.95-1.68 (m, 9H), 1.63-1.52 (m, 2H), 1.48-1.36 (m, 2H) ppm. MS m/z 572.8 $[M+H]^+$.

EXAMPLE 4: PREPARATION OF COMPOUND 3S

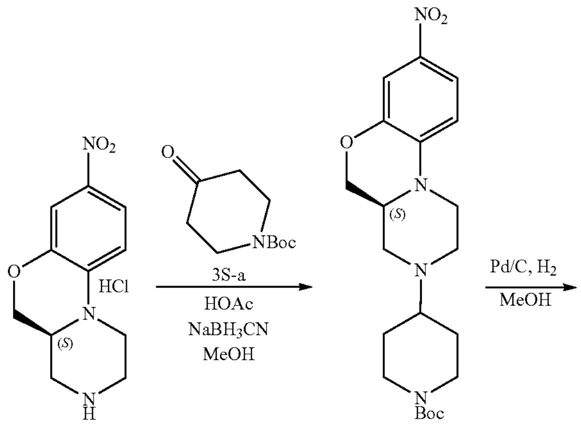

1S-a 3S-b

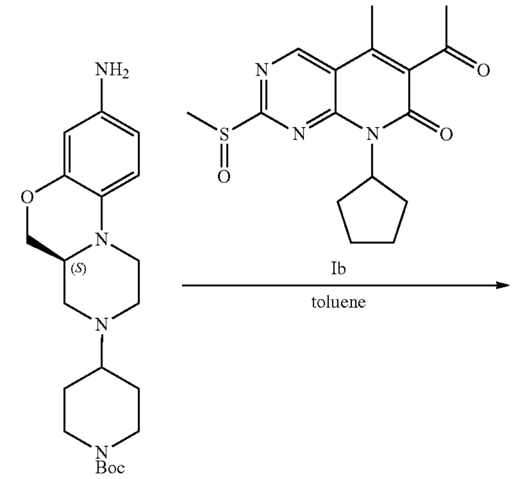

2S-c

-continued

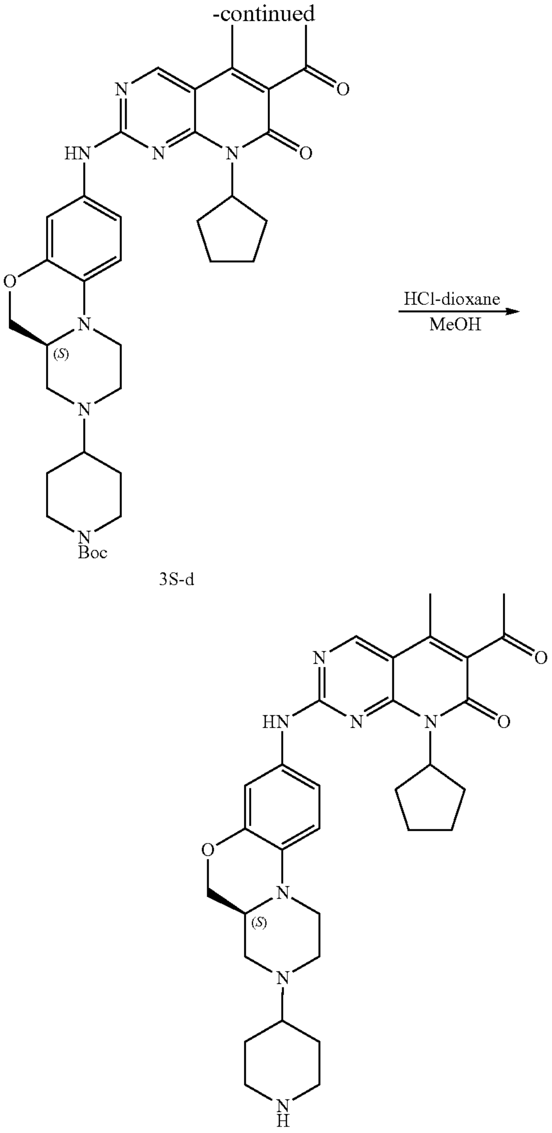

3S-d

3S

Compound 1S-a (1 g, 4.25 mmol) was dissolved in methanol (20 mL). N-Boc piperidone (3S-a, 2.54 g, 12.75 mmol) and AcOH (4 drops) were added. The reaction mixture was stirred at room temperature for 1 hour. Sodium cyanoborohydride (801 mg, 12.75 mmol) was added, and the reaction mixture was stirred at room temperature overnight. The reaction was monitored by TLC for completion. It was concentrated under reduced pressure to remove methanol. Water (10 mL) was added, and the resulted mixture was extracted with dichloromethane (3×20 mL). The combined organic layers were washed with brine, dried over anhydrous sodium sulfate, filtered, and concentrated under reduced pressure. The residue was purified in $SiO_2$ chromatography ($CH_2Cl_2$:$CH_3OH$=20:1) to afford compound 3S-b (1.39 g, yield 78%) as a yellow solid. MS m/z 419.5 $[M+H]^+$.

To methanol (5 mL) at room temperature was added compound 3S-b (190 mg, 0.45 mmol) and Pd on carbon (10%, 60 mg). The reaction mixture was stirred at room temperature under 1 atmospheric pressure of $H_2$ for 3 hours. The reaction was monitored by TLC for completion. It was filtered through celite, and the filtrate was concentrated under reduced pressure. The residue was purified in $SiO_2$ chromatography ($CH_2Cl_2$:$CH_3OH$=40:1) to afford compound 3S-c (80 mg, yield 45%) as a yellow solid. MS m/z 389.5 $[M+H]^+$.

Compound 3S-c (80 mg, 0.21 mmol) and compound Ib (69 mg, 0.21 mmol) were dissolved in toluene (1 mL). The reaction mixture was stirred at 90° C. overnight. The reaction was monitored by TLC for completion. It was cooled to room temperature, and concentrated under reduced pressure. The residue was purified in $SiO_2$ chromatography ($CH_2Cl_2$:$CH_3OH$=30:1) to afford compound 3S-d (30 mg, yield 22%) as a yellow solid. MS m/z 658.8 $[M+H]^+$.

Compound 3S-d (30 mg, 0.45 mmol) was dissolved in methanol (2 mL). A solution of HCl in 1,4-dixoane (4.0 M, 1.1 mL, 4.4 mmol) was added under ice bath. The reaction mixture was stirred at room temperature for 1 hour. The solvent was removed under reduced pressure. The residue was neutralized with sat. $NaHCO_3$ aq. to pH=7-8, and extracted with dichloromethane (3×10 mL). The combined organic layers were washed with brine, dried over anhydrous sodium sulfate, filtered, and concentrated under reduced pressure. The residue was purified by prep-TLC ($CH_2Cl_2$:$CH_3OH$=20:1) to afford compound 3S (13 mg, yield 51%) as a yellow solid. $^1H$ NMR (500 MHz, $CDCl_3$) δ 8.70 (s, 1H), 7.11 (bs, 1H), 7.11 (d, J=2.5 Hz, 1H), 6.97 (dd, J=9.0, 2.5 Hz, 1H), 6.76 (d, J=9.0 Hz, 1H), 5.88-5.80 (m, 1H), 4.20 (dd, J=10.0, 2.0 Hz, 1H), 4.03 (t, J=10.0 Hz, 1H), 3.67 (d, J=12.0 Hz, 1H), 3.22-3.10 (m, 3H), 3.03 (d, J=11.0 Hz, 1H), 2.89 (d, J=10.5 Hz, 1H), 2.82-2.75 (m, 1H), 2.61 (t, J=11.5 Hz, 2H), 2.54 (s, 3H), 2.54-2.47 (m, 1H), 2.44-2.39 (m, 1H), 2.34 (s, 3H), 2.34-2.25 (m, 2H), 2.07 (t, J=10.8 Hz, 1H), 1.99-1.89 (m, 2H), 1.86-1.79 (m, 4H), 1.67-1.56 (m, 2H), 1.49-1.38 (m, 2H) ppm. MS m/z 558.8 $[M+H]^+$.

EXAMPLE 5: PREPARATION OF COMPOUND 4S

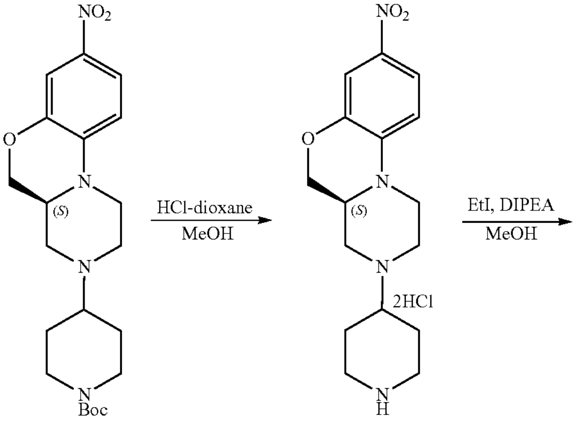

3S-b 4S-a

-continued

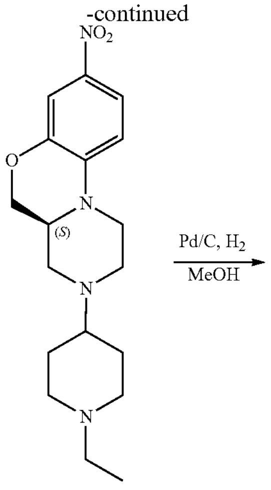

4S-b

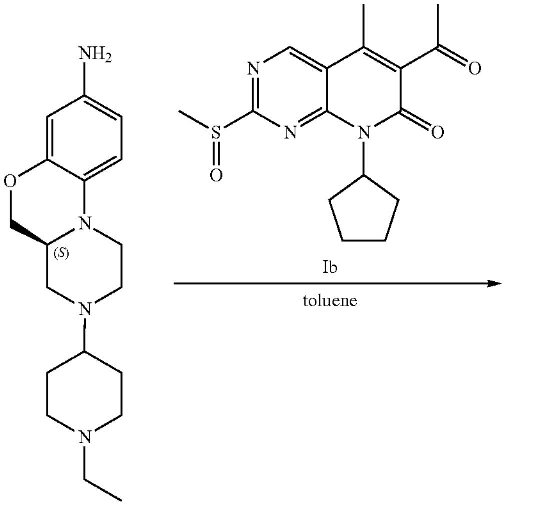

4S-c

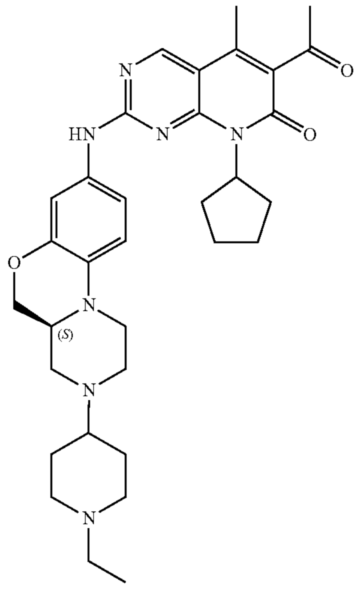

4S

Compound 3S-b (500 mg, 1.19 mmol) was dissolved in methanol (10 mL). A solution of HCl in 1,4-dioxane (4.0 M, 3 mL, 12 mmol) was added under ice bath. The reaction mixture was stirred at room temperature for 1 hour. It was concentrated under reduced pressure to afford compound 4S-a (500 mg) as a yellow solid, which was used in next step. MS m/z 319.5 $[M+H]^+$.

Compound 4S-a (140 mg, 0.36 mmol) was dissolved in methanol (5 mL) followed by the addition of DIPEA (0.2 mL, 1.32 mmol) and iodoethane (137 mg, 0.88 mmol). The reaction mixture was stirred at 50° C. overnight. The reaction was monitored by TLC for completion. It was concentrated under reduced pressure. The residue was purified in $SiO_2$ chromatography ($CH_2Cl_2$:$CH_3OH$=20:1) to afford compound 4S-b (56 mg, yield 45%) as a yellow oil. MS m/z 347.5 $[M+H]^+$.

To methanol (3 mL) was added compound 4S-b (56 mg, 0.16 mmol) and Pd on carbon (10%, 30 mg) at room temperature. The reaction mixture was stirred at room temperature under 1 atmospheric pressure of $H_2$ for 3 hours. The reaction was monitored by TLC for completion. It was filtered through celite and the filtrate was concentrated under reduced pressure. The residue was purified in $SiO_2$ chromatography ($CH_2Cl_2$:$CH_3OH$=20:1) to afford compound 4S-c (36 mg, yield 70%) as a yellow solid. MS m/z 317.5 $[M+H]^+$.

Compound 4S-c (36 mg, 0.11 mmol) and compound Ib (45 mg, 0.14 mmol) were dissolved in toluene (1 mL). The reaction mixture was stirred at 90° C. overnight. The reaction was monitored by TLC for completion. It was cooled to room temperature, and concentrated under reduced pressure. The residue was purified by prep-TLC ($CH_2Cl_2$:$CH_3OH$=30:1) to afford compound 4S (25 mg, yield 38%) as a yellow solid. $^1$H NMR (500 MHz, $CDCl_3$) δ 8.70 (s, 1H), 7.23 (bs, 1H), 7.11 (d, J=2.5 Hz, 1H), 6.95 (dd, J=9.0, 2.5 Hz, 1H), 6.76 (d, J=9.0 Hz, 1H), 5.88-5.80 (m, 1H), 4.19 (dd, J=10.5, 2.5 Hz, 1H), 4.02 (dd, J=10.5, 9.5 Hz, 1H), 3.66 (d, J=11.5 Hz, 1H), 3.17-3.10 (m, 1H), 3.07 (d, J=10.5 Hz, 2H), 3.01 (d, J=9.5 Hz, 1H), 2.86 (d, J=10.0 Hz, 1H), 2.81-2.75 (m, 1H), 2.54 (s, 3H), 2.54-2.42 (m, 3H), 2.39-2.27 (m, 3H), 2.34 (s, 3H), 2.08 (t, J=10.8 Hz, 1H), 2.05-1.75 (m, 8H), 1.70-1.56 (m, 4H), 1.13 (t, J=7.0 Hz, 3H) ppm. MS m/z 586.8 $[M+H]^+$.

EXAMPLE 6: PREPARATION OF COMPOUND 5S

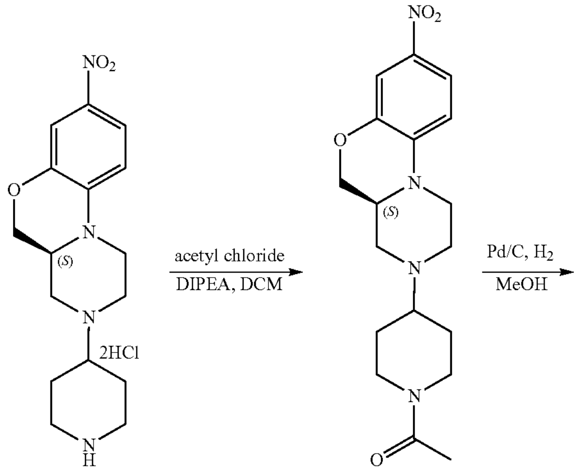

4S-a 5S-b

-continued

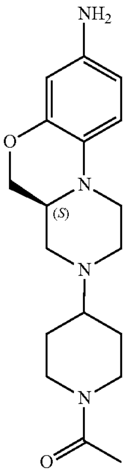

5S-b

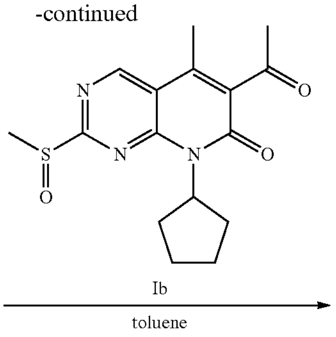

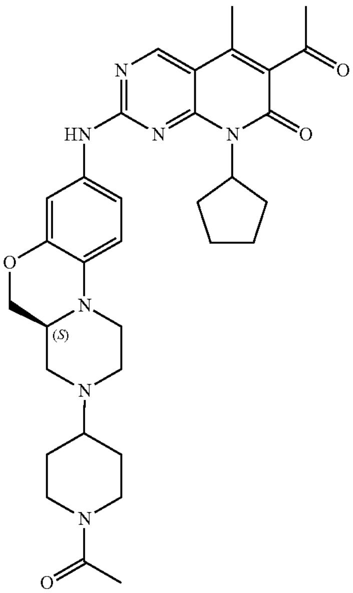

5S

To a solution of compound 4S-a (200 mg, 0.63 mmol) in dichloromethane (5 mL) was added DIPEA (0.3 mL, 1.88 mmol) at 0° C., followed by the addition of a solution of AcCl (98 mg, 1.26 mmol) in dichloromethane (1.0 mL). The reaction mixture was stirred at room temperature for 1 hour. The reaction was monitored by TLC for completion. Water (10 mL) was added, and the resulted mixture was extracted with dichloromethane (3×10 mL). The combined organic layers were washed with brine (20 mL), dried over anhydrous sodium sulfate, filtered, and concentrated under reduced pressure. The residue was purified in $SiO_2$ chromatography ($CH_2Cl_2$:$CH_3OH$=30:1) to afford compound 5S-a (170 mg, yield 92%) as a yellow solid. MS m/z 361.5 $[M+H]^+$.

To methanol (3 mL) was added compound 5S-a (170 mg, 0.47 mmol) and Pd on carbon (10%, 60 mg) at room temperature. The reaction mixture was stirred at room temperature under 1 atmospheric pressure of $H_2$ for 3 hours. The reaction was monitored by TLC for completion. It was filtered through celite and the filtrate was concentrated under reduced pressure. The residue was purified in $SiO_2$ chromatography ($CH_2Cl_2$:$CH_3OH$=20:1) to afford compound 5S-b (130 mg, yield 83%) as a yellow solid. MS m/z 331.5 $[M+H]^+$.

Compound 5S-b (65 mg, 0.20 mmol) and compound Ib (79 mg, 0.24 mmol) were dissolved in toluene (1 mL). 中 . The reaction mixture was stirred at 90° C. overnight. The reaction was monitored by TLC for completion. It was cooled to room temperature and concentrated under reduced pressure. The residue was purified by prep-TLC ($CH_2Cl_2$: $CH_3OH$=20:1) to afford compound 5S (15 mg, yield 13%) as a yellow solid. $^1$H NMR (500 MHz, $CD_3OD$) δ 8.81 (s, 1H), 7.18 (d, J=2.0 Hz, 1H), 6.97 (d, J=8.5 Hz, 1H), 6.83 (d, J=8.5 Hz, 1H), 6.02-5.83 (m, 1H), 4.57 (d, J=12.5 Hz, 1H), 4.25 (d, J=10.0 Hz, 1H), 4.04-3.92 (m, 2H), 3.78 (d, J=11.0 Hz, 1H), 3.19-2.99 (m, 4H), 2.78-2.59 (m, 3H), 2.58-2.50 (m, 1H), 2.47 (s, 3H), 2.38-2.25 (m, 2H), 2.35 (s, 3H), 2.17-2.08 (m, 1H), 2.11 (s, 3H), 2.05-1.89 (m, 4H), 1.87-1.78 (m, 2H), 1.68-1.59 (m, 2H), 1.56-1.49 (m, 1H), 1.45-1.37 (m, 1H) ppm. MS m/z 600.8 $[M+H]^+$.

EXAMPLE 7: PREPARATION OF COMPOUND 6S

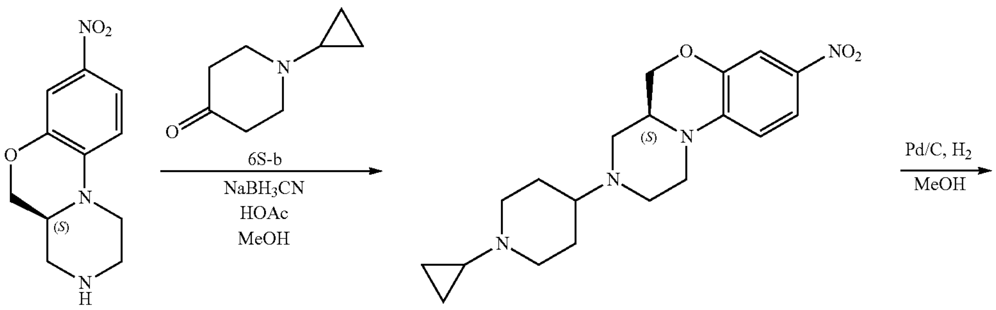

6S-a 6S-c

-continued

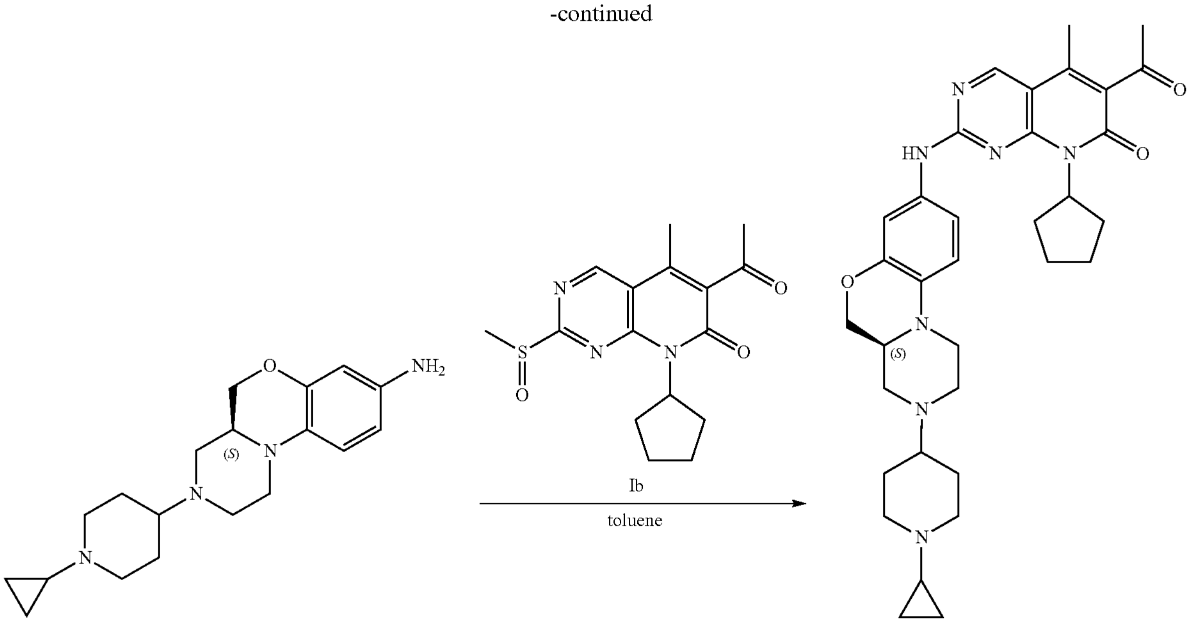

6S-d 6S

A mixture of compound 6S-a (250 mg, 1.06 mmol), 1-cyclopropyl-4-piperidone (6S-b, 444 mg, 3.19 mmol), and AcOH (2 drops) in methanol (15 mL) was stirred at room temperature for 1 hour. Sodium cyanoborohydride (200 mg, 3.19 mmol) was added. The reaction mixture was stirred at room temperature overnight. The reaction was monitored by TLC for completion. It was concentrated under reduced pressure. The residue was purified in $SiO_2$ chromatography ($CH_2Cl_2$:$CH_3OH$=20:1, 2% aqueous ammonium hydroxide solution) to afford compound 6S-c (200 mg, yield 53%) as a yellow solid. MS m/z 359.4 $[M+H]^+$.

To methanol (8 mL) was added compound 6S-c (200 mg, 0.56 mmol) and Pd on carbon (10%, 80 mg) at room temperature. The reaction mixture was stirred at room temperature under 1 atmospheric pressure of $H_2$ for 1 hour. The reaction was monitored by TLC for completion. It was filtered through celite and the filtrate was concentrated under reduced pressure. The residue was purified in $SiO_2$ chromatography (dichloromethane:methanol=20:1, 2% aqueous ammonium hydroxide solution) to afford compound 6S-d (128 mg, yield 70%) as a yellow oil. MS m/z 329.5 $[M+H]^+$.

A mixture of compound 6S-d (88 mg, 0.27 mmol) and compound Ib (89 mg, 0.27 mmol) in toluene (1.5 mL) in a seated tube was heated to 100° C., and stirred overnight. The reaction was monitored by TLC for completion. It was cooled to room temperature, and concentrated under reduced pressure. The residue was purified in $SiO_2$ chromatography ($CH_2Cl_2$:$CH_3OH$=20:1) to afford compound 6S (96 mg, yield 60%) as a yellow solid. $^1H$ NMR (500 MHz, DMSO-$d_6$) δ 9.87 (bs, 1H), 8.90 (s, 1H), 7.16 (d, J=1.9 Hz, 1H), 7.06 (d, J=8.3 Hz, 1H), 6.81 (d, J=8.9 Hz, 1H), 5.91-5.76 (m, 1H), 4.22 (dd, J=10.5, 2.2 Hz, 1H), 3.93-3.84 (m, 1H), 3.69 (d, J=11.0 Hz, 1H), 3.04-2.78 (m, 5H), 2.58-2.51 (m, 1H), 2.41 (s, 3H), 2.37-2.06 (m, 6H), 2.29 (s, 3H), 1.95-1.83 (m, 3H), 1.81-1.68 (m, 4H), 1.61-1.52 (m, 3H), 1.41-1.27 (m, 2H), 0.43-0.34 (m, 2H), 0.32-0.21 (m, 2H) ppm. MS m/z 598.8 $[M+H]^+$.

EXAMPLE 8: PREPARATION OF COMPOUND 7S

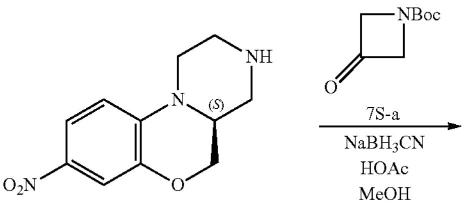

6S-a

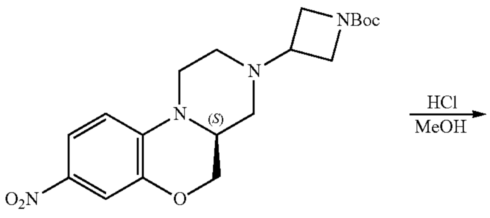

7S-b

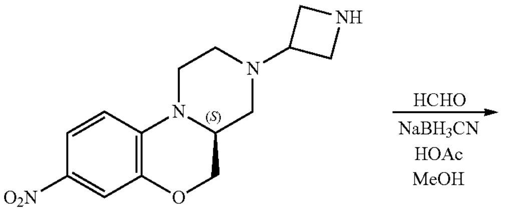

7S-c

-continued

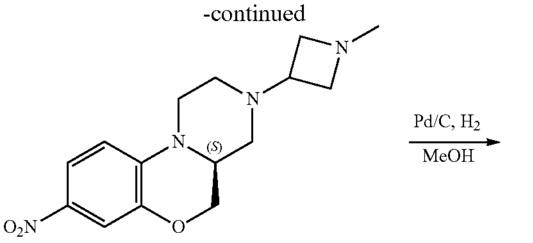

7S-d

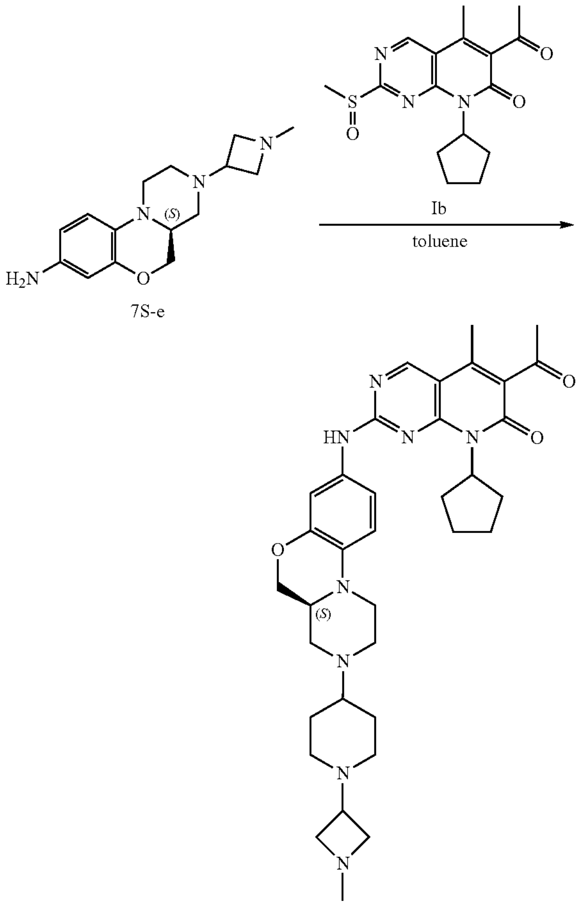

Ib 7S-e

7S

A mixture of compound 6S-a (500 mg, 2.13 mmol), 1-Boc-3-azyclobutanone (7S-a, 1.09 g, 6.38 mmol) and AcOH (4 drops) in methanol (10 mL) was stirred at room temperature for 1 hour. Sodium cyanoborohydride (400 mg, 6.38 mmol) was added. The reaction mixture was stirred at room temperature overnight. The reaction was monitored by TLC for completion. It was concentrated under reduced pressure. The residue was purified in $SiO_2$ chromatography ($CH_2Cl_2$:$CH_3OH$=20:1, 2% aqueous ammonium hydroxide solution) to afford compound 7S-b (1.24 g) as a yellow solid which was used in next step. MS m/z 391.4 $[M+H]^+$.

Compound 7S-b (1.24 g, 3.18 mmol) was dissolved in methanol (15 mL) at room temperature followed by the addition of a solution of HCl in methanol (4.0 M, 4 mL). The reaction mixture was stirred at 60° C. for 1 hour. The reaction was monitored by TLC for completion. It was concentrated under reduced pressure, neutralized with saturated $NaHCO_3$ aq. to pH=7-8, and concentrated under reduced pressure. The residue was purified in $SiO_2$ chromatography ($CH_2Cl_2$:$CH_3OH$=10:1, 2% aqueous ammonium hydroxide solution) to afford compound 7S-c (410 mg, yield of two steps 66%) as a yellow solid. MS m/z 291.3 $[M+H]^+$.

A mixture of compound 7S-c (410 mg, 1.41 mmol), paraformaldehyde (127 mg, 4.24 mmol), and AcOH (3 drops) in methanol (8 mL) was stirred at room temperature for 1 hour. Sodium cyanoborohydride (266 mg, 4.24 mmol) was added. The reaction mixture was stirred at room temperature for 2 hours. The reaction was monitored by TLC for completion. It was filtered, and the filtrate was concentrated under reduced pressure. The residue was purified in $SiO_2$ chromatography (dichloromethane:methanol=20:1, 2% aqueous ammonium hydroxide solution) to afford compound 7S-d (254 mg, purity 80%, yield 47%) as a yellow solid, which was used in next step. MS m/z 305.3 $[M+H]^+$.

To methanol (3 mL) was added compound 7S-d (100 mg, 0.28 mmol) and Pd on carbon (10%, 80 mg) at room temperature. The reaction mixture was stirred at room temperature under 1 atmospheric pressure of $H_2$ for 1 hour. The reaction was monitored by TLC for completion. It was filtered through celite and the filtrate was concentrated under reduced pressure. The residue was purified in $SiO_2$ chromatography (dichloromethane:methanol=20:1, 2% aqueous ammonium hydroxide solution) to afford compound 7S-e (47 mg, yield 51%) as a yellow solid. MS m/z 275.4 $[M+H]^+$.

A mixture of compound 7S-e (47 mg, 0.17 mmol) and compound Ib (57 mg, 0.17 mmol) in toluene (1.5 mL) in a sealed tube was heated to 100° C. overnight. The reaction was monitored by TLC for completion. It was cooled to room temperature, and concentrated under reduced pressure. The residue was purified by prep-TLC ($CH_2Cl_2$:$CH_3OH$=20:1, 2% aqueous ammonium hydroxide solution) to afford compound 7S (5 mg, yield 5%) as a yellow solid. MS m/z 544.7 $[M+1-1]^+$.

EXAMPLE 9: PREPARATION OF COMPOUND 8S

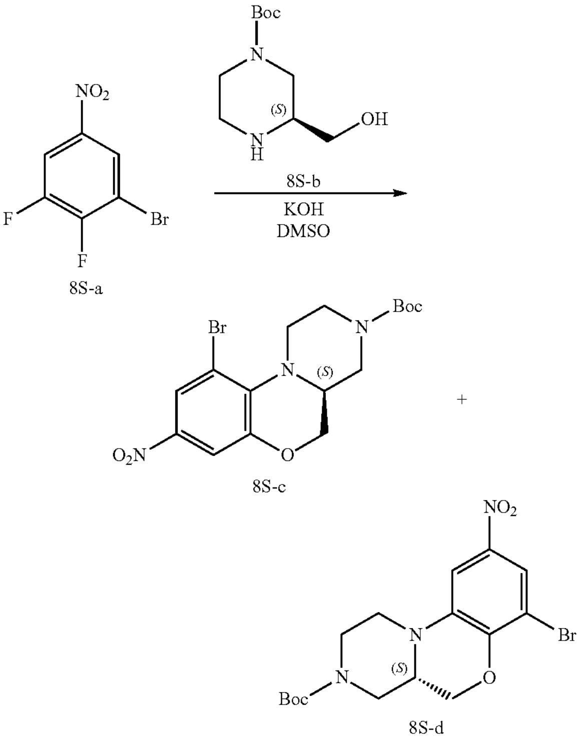

8S-a 8S-c 8S-d

-continued

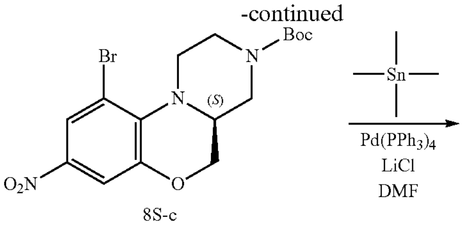

8S-c

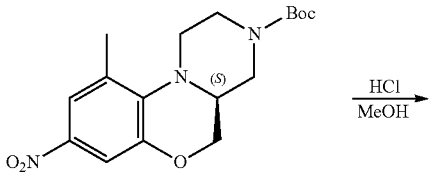

8S-e

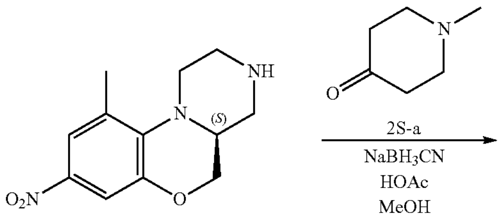

8S-f

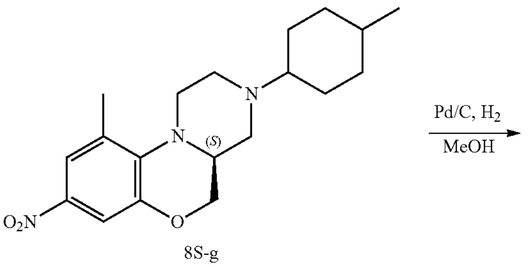

8S-g

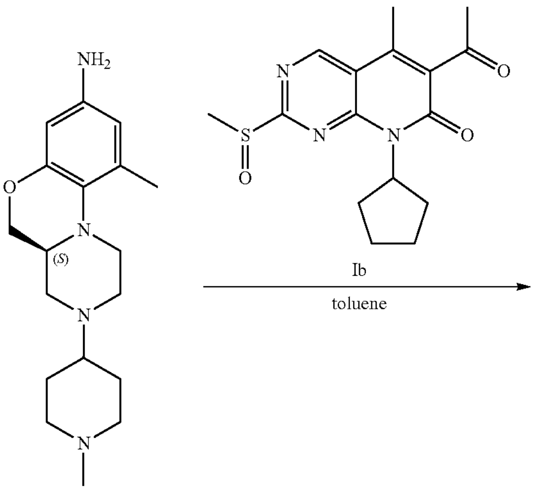

8S-h

-continued

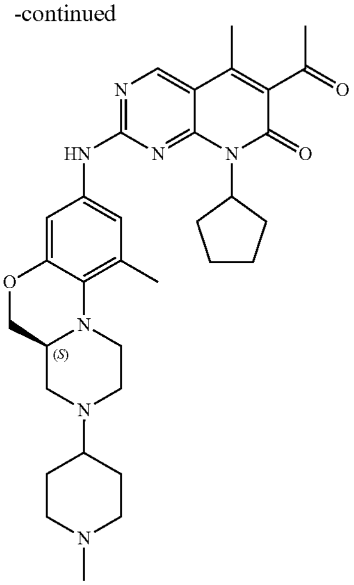

8S

Compound 8S-a (100 mg, 0.42 mmol), compound 8S-b (91 mg, 0.42 mmol), and KOH (71 mg, 1.26 mmol) were dissolved in dimethylsulfoxide (5 mL). The reaction mixture was stirred at room temperature for 3 hours, and stirred at 60° C. for 3 hours. It was cooled to room temperature, and poured into ice water. The resulted mixture was stirred at room temperature for 1 hour. It was extracted with dichloromethane (3×25 mL). The combined organic layers were washed with brine, dried over anhydrous sodium sulfate, filtered, and concentrated under reduced pressure. The residue was purified in $SiO_2$ chromatography (petroleum ether: EtOAc=10:1) to afford compound 8S-c (64 mg, yield 37%) as a yellow solid and compound 8S-d (64 mg, yield 37%) as a yellow solid. 8S-c: $^1$H NMR (500 MHz, $CDCl_3$) δ 8.03 (d, J=2.5 Hz, 1H), 7.71 (d, J=2.6 Hz, 1H), 4.26-4.15 (m, 2H), 3.86-3.78 (m, 2H), 3.60 (dd, J=13.8, 4.1 Hz, 1H), 3.52-3.36 (m, 2H), 3.29-3.15 (m, 2H), 1.48 (s, 9H); 8S-d: $^1$H NMR (500 MHz, $CDCl_3$) δ 7.94 (d, J=2.5 Hz, 1H), 7.63 (d, J=2.5 Hz, 1H), 4.49-4.44 (m, 1H), 4.28-4.04 (m, 3H), 3.71 (d, J=11.3 Hz, 1H), 3.22-3.15 (m, 1H), 3.10-3.01 (m, 1H), 2.88-2.79 (m, 1H), 2.66-2.57 (m, 1H), 1.49 (s, 9H) ppm.

A mixture of compound 8S-c (64 mg, 0.16 mmol), tetramethyltin (56 mg, 0.31 mmol), tetrakis(triphenylphosphine) palladium (9 mg, 0.01 mmol), and LiCl (13 mg, 0.31 mmol) in DMF (2 mL) was heated to 90° C., and stirred overnight. It was filtered and the filtrated was concentrated under reduced pressure. The residue was purified in $SiO_2$ chromatography (Petroleum ether:EtOAc=10:1) to afford compound 8S-e (33 mg, yield 60%) as a yellow solid. $^1$H NMR (500 MHz, $CDCl_3$) δ 7.65 (d, J=2.5 Hz, 1H), 7.59 (d, J=2.6 Hz, 1H), 4.24-4.14 (m, 2H), 3.89-3.78 (m, 2H), 3.60-3.49 (m, 1H), 3.39-3.30 (m, 1H), 3.28-3.18 (m, 1H), 3.10-2.98 (m, 2H), 2.37 (s, 3H), 1.48 (s, 9H).

Compound 8S-e (200 mg, 0.57 mmol) was dissolved in methanol (2 mL). A solution of HCl in methanol (1 mL, 4 M) was added under ice bath. The reaction mixture was stirred at room temperature for 1 hour. The reaction was monitored by TLC for completion. It was concentrated under reduced pressure, neutralized with saturated $NaHCO_{3[g3]}$ aq. (10 mL), and extracted with EtOAc (3×10 mL). The combined organic layers were washed with brine, dried over anhydrous sodium sulfate, filtered, and concentrated under reduced pressure to afford compound 8S-f (100 mg, yield 70%) as a yellow solid. MS m/z 250.3 $[M+H]^+$.

A mixture of compound 8S-f (100 mg, 0.40 mmol), N-methylpiperidone (2S-a, 227 mg, 2.00 mmol), and AcOH (2 drops) in methanol (5 mL) was stirred at room temperature for 1 hour. Sodium cyanoborohydride (75 mg, 1.21 mmol) was added. The reaction mixture was stirred at room temperature overnight. It was concentrated under reduced pressure, extracted with dichloromethane (3×15 mL). The combined organic layers were washed with brine, dried over anhydrous sodium sulfate, filtered, and concentrated under reduced pressure. The residue was purified in $SiO_2$ chromatography (dichloromethane:methanol=30:1) to afford compound 8S-g (140 mg) as a yellow solid, which was used in next step. MS m/z 347.4 $[M+H]^+$.

To methanol (5 mL) was added compound 8S-g (101 mg, 0.29 mmol) and Pd on carbon (10%, 20 mg) at room temperature. The reaction mixture was stirred at room temperature under 1 atmospheric pressure of $H_2$ for 3 hours. The reaction was monitored by TLC for completion. It was filtered through celite and the filtrate was concentrated under reduced pressure. The residue was purified in $SiO_2$ chromatography (dichloromethane:methanol=50:1) to afford compound 8S-h (63 mg, yield 68%) as a brown solid. MS m/z 317.4 $[M+H]^+$.

Compound 8S-h (53 mg, 0.17 mmol) and compound Ib (56 mg, 0.17 mmol) were dissolved in toluene (1 mL). The reaction mixture was stirred at 100° C. overnight. The reaction was monitored by TLC for completion. It was cooled to room temperature, and concentrated under reduced pressure. The residue was purified by prep-TLC ($CH_2Cl_2$:$CH_3OH$=20:1) to afford compound 8S (12 mg, yield 12%) as a yellow solid. $^1H$ NMR (500 MHz, $CDCl_3$) δ 8.72 (s, 1H), 7.15 (bs, 1H), 7.03 (s, 1H), 6.96 (s, 1H), 5.93-5.84 (m, 1H), 4.60 (t, J=10.7 Hz, 1H), 4.00 (dd, J=10.6, 2.8 Hz, 1H), 3.19 (d, J=10.5 Hz, 1H), 3.13-3.01 (m, 3H), 2.92-2.85 (m, 2H), 2.82 (d, J=11.5 Hz, 2H), 2.62-2.55 (m, 1H), 2.54 (s, 3H), 2.46-2.39 (m, 3H), 2.35 (s, 3H), 2.34-2.30 (m, 3H), 2.29 (s, 3H), 2.04-1.73 (m, 9H), 1.69-1.55 (m, 3H) ppm. MS m/z 586.8 $[M+H]^+$.

EXAMPLE 10: PREPARATION OF COMPOUND 9S

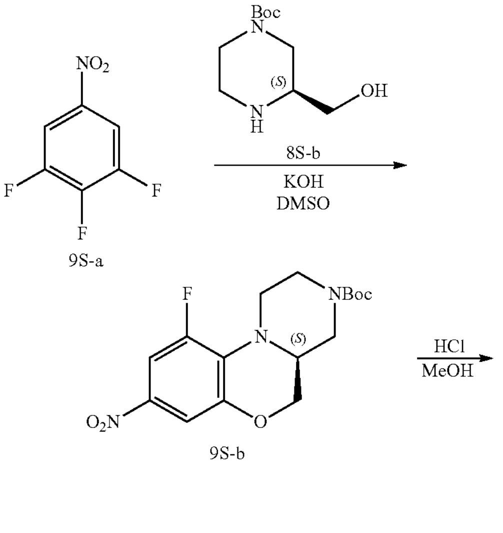

9S-a 9S-b

-continued

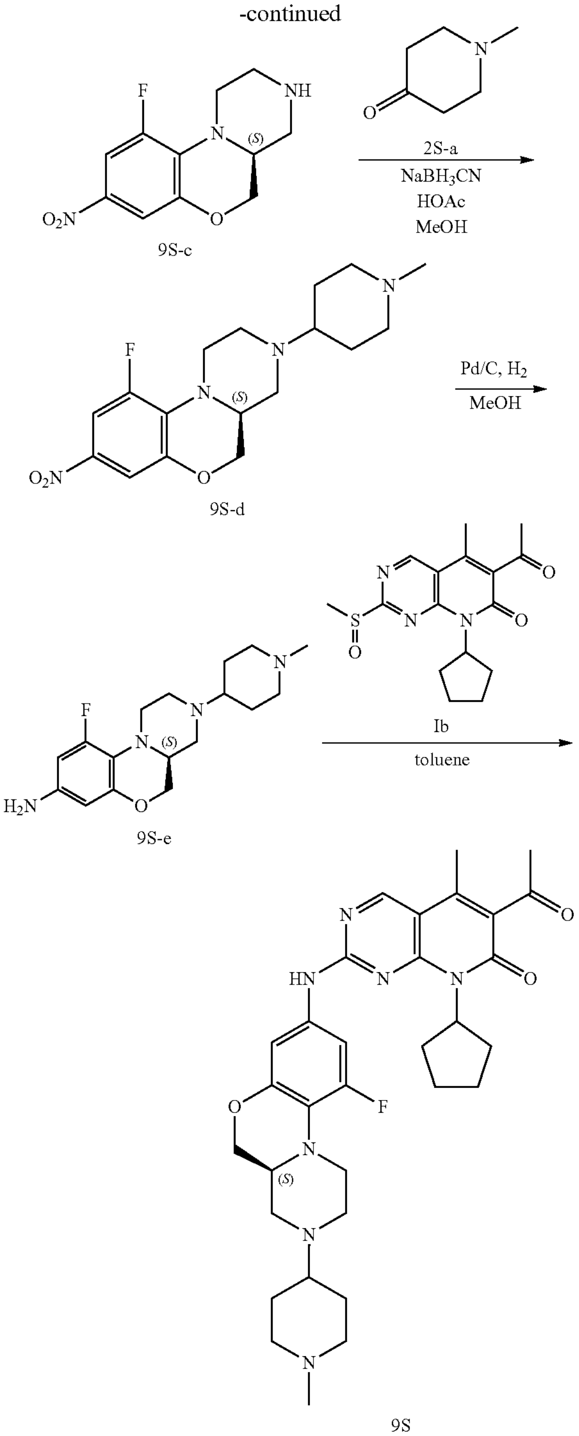

9S-c 9S-d 9S-e

9S

Compound 9S-a (1.0 g, 5.65 mmol), compound 8S-b (1.22 g, 5.65 mmol), and KOH (950 mg, 16.94 mmol) were dissolved in DMSO (15 mL). The reaction mixture was stirred at room temperature for 3 hours, and stirred at 60° C. for 3 hours. The reaction was monitored by TLC for completion. It was cooled to room temperature, and poured into ice water. The reaction mixture was stirred at room temperature for 1 hour, extracted with dichloromethane (3×30 mL). The combined organic layers were washed with brine, dried over anhydrous sodium sulfate, filtered, and concentrated under reduced pressure. The residue was purified in $SiO_2$ chromatography (petroleum ether:EtOAc:$CH_2Cl_2$=5:1:1) to afford compound 9S-b (1.45 g, yield 73%) as a yellow solid. MS m/z 354.4 $[M+H]^+$.

Compound 9S-b (1.45 g, 4.10 mmol) was dissolved in methanol (15 mL). A solution of HCl in methanol (4.0 M, 4 mL) was added. The resulted mixture was stirred at 60° C. for 1 hour. The reaction was monitored by TLC for completion. It was concentrated under reduced pressure. The residue was purified in $SiO_2$ chromatography (dichloromethane: methanol=10:1, 2% aqueous ammonium hydroxide solution) to afford compound 9S-c (1.25 g, yield 100%) as a yellow solid. MS m/z 254.3 $[M+H]^+$.

A mixture of compound 9S-c (500 mg, 1.73 mmol), N-methyl-4-piperidone (2S-a, 587 mg, 5.18 mmol), and AcOH (4 drops) in methanol (8 mL) was stirred at room temperature for 1 hour. Sodium cyanoborohydride (326 mg, 5.18 mmol) was added. The reaction mixture was stirred at room temperature overnight. It was concentrated under reduced pressure. The residue was purified in $SiO_2$ chromatography ($CH_2Cl_2$:$CH_3OH$=20:1, 2% aqueous ammonium hydroxide solution) to afford compound 9S-d (704 mg) as a yellow solid which was used in next step. MS m/z 351.4 $[M+H]^+$.

To methanol (3 mL) was added compound 9S-d (80 mg, 0.23 mmol) and Pd on carbon (10%, 80 mg) at room temperature. The reaction mixture was stirred at room temperature under 1 atmospheric pressure of $H_2$ for 1 hour. The reaction was monitored by TLC for completion. It was filtered through celite and the filtrate was concentrated under reduced pressure. The residue was purified in $SiO_2$ chromatography ($CH_2Cl_2$:$CH_3OH$=20:1, 2% aqueous ammonium hydroxide solution) to afford compound 9S-e (50 mg, yield 68%) as a yellow oil. MS m/z 321.5 $[M+H]^+$.

A mixture of compound 9S-e (50 mg, 0.16 mmol) and compound Ib (52 mg, 0.16 mmol) in toluene (1.5 mL) in a sealed tube was stirred at 100° C. overnight. The reaction was monitored by TLC for completion. It was cooled to room temperature and concentrated under reduced pressure. The residue was purified in $SiO_2$ chromatography ($CH_2Cl_2$: $CH_3OH$=20:1, 2% aqueous ammonium hydroxide solution) to afford compound 9S (13 mg, yield 14%) as a yellow solid. $^1H$ NMR (500 MHz, $CDCl_3$) δ 8.72 (s, 1H), 7.13 (s, 1H), 7.07 (dd, J=14.6, 2.5 Hz, 1H), 6.83 (s, 1H), 5.91-5.79 (m, 1H), 4.17-4.08 (m, 2H), 3.79-3.68 (m, 1H), 3.27-3.19 (m, 1H), 3.13-3.03 (m, 3H), 2.89-2.77 (m, 2H), 2.66-2.58 (m, 1H), 2.54 (s, 3H), 2.49-2.27 (m, 7H), 2.36 (s, 3H), 2.04-1.93 (m, 3H), 1.92-1.80 (m, 6H), 1.73-1.59 (m, 3H) ppm. MS m/z 590.8 $[M+H]^+$.

EXAMPLE 11: PREPARATION OF COMPOUND 10S

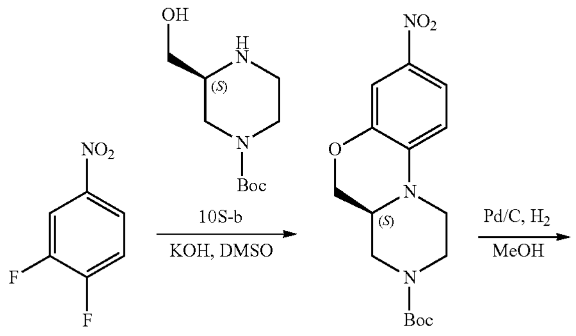

10S-a 10S-c

-continued

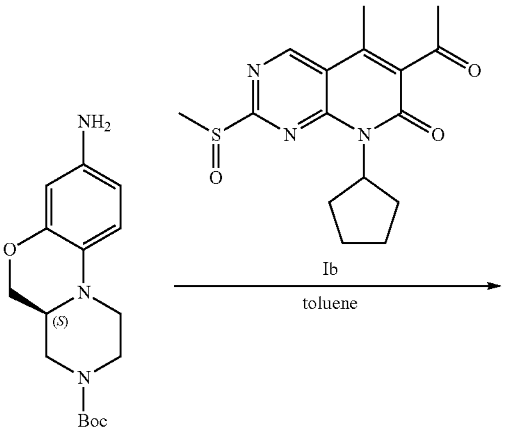

10S-d

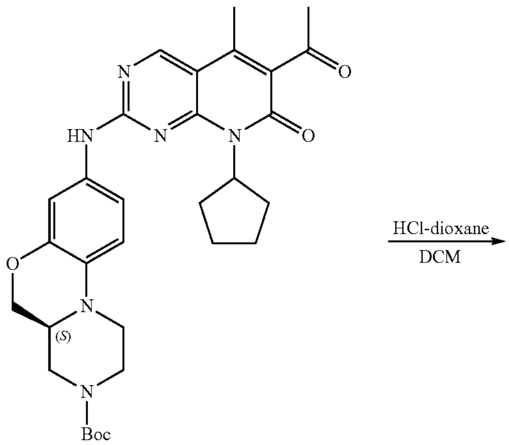

10S-e

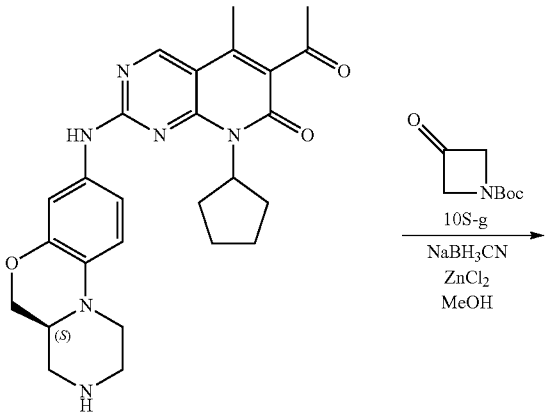

10S-f

-continued

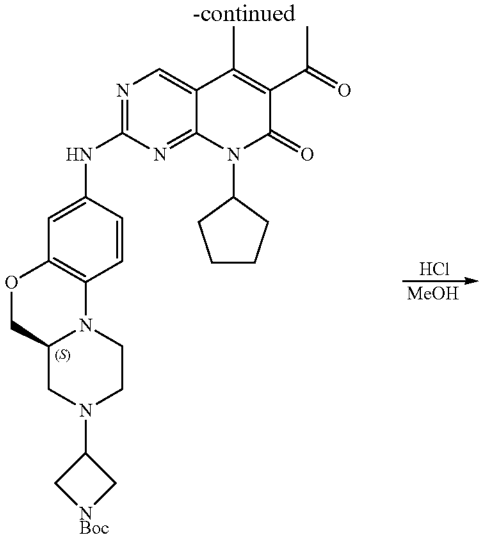

10S-h

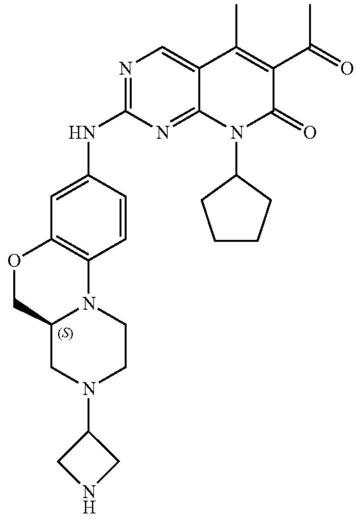

10S

Compound 10S-a (2.95 g, 13.6 mmol) and compound 10S-b (2.17 g, 13.6 mmol) were dissolved in DMSO (30 mL). KOH (2.30 g, 40.9 mmol) was added. The reaction mixture was stirred at room temperature until compound 10S-a disappeared. It was stirred at 60° C. overnight. The reaction was monitored by TLC for completion. The reaction was quenched with water. The resulted mixture was extracted with EtOAc. The combined organic layers were washed with brine, dried over anhydrous sodium sulfate, filtered, and concentrated under reduced pressure. The residue was purified in $SiO_2$ chromatography (petroleum ether: EtOAc=1:1) to afford compound 10S-c (2.30 g, 50%). MS m/z 336.4 $[M+H]^+$, 280.4$[M-55]^+$. $^1H$ NMR (500 MHz, $CDCl_3$) δ 7.83-7.75 (m, 1H), 7.65 (d, J=2.6 Hz, 1H), 6.75 (d, J=9.1 Hz, 1H), 4.29 (dd, J=11.0, 3.0 Hz, 1H), 4.27-4.01 (m, 2H), 3.98 (dd, J=11.0, 8.0 Hz, 1H), 3.78 (d, J=11.4 Hz, 1H), 3.36-3.27 (m, 1H), 3.12-2.99 (m, 1H), 2.98-2.89 (m, 1H), 2.76-2.53 (m, 1H), 1.48 (s, 9H) ppm.

Compound 10S-c (6.10 g, 18.19 mmol) was dissolved in methanol (100 mL). Pd on carton (7%, 500 mg) was added. The reaction mixture was stirred at room temperature under 1 atmospheric pressure of $H_2$ for 1 hour. The reaction was monitored by TLC for completion, It was filtered through celite, and the filtrate was concentrated under reduced pressure. The residue was purified in $SiO_2$ chromatography ($CH_2Cl_2$:$CH_3OH$: aqueous ammonium hydroxide solution=30:1:0.3) to afford compound 10S-d 4.70 g, 85%). MS m/z 306.4 $[M+H]^+$. $^1H$ NMR (500 MHz, $CDCl_3$) δ 6.64 (d, J=8.5 Hz, 1H), 6.32 (dd, J=8.5, 2.6 Hz, 1H), 6.29 (d, J=2.5 Hz, 1H), 4.23-4.01 (m, 3H), 3.96 (dd, J=10.6, 9.0 Hz, 1H), 3.56 (d, J=11.3 Hz, 1H), 3.15-2.90 (m, 2H), 2.71-2.49 (m, 2H), 1.48 (s, 9H) ppm.

Compound 10S-d (4.7 g, 15.39 mmol) and compound Ib (5.64 g, 16.93 mmol) were dissolved in toluene (30 mL). The reaction mixture was stirred at 90~100° C. overnight. The reaction was monitored by TLC for completion. It was cooled to room temperature, and filtered. The filter cake was washed with EtOAc and dried to afford a yellow solid. This solid was purified in $SiO_2$ chromatography ($CH_2Cl_2$: $CH_3OH$: aqueous ammonium hydroxide solution=50:1:0.5) to afford compound 10S-e (5.30 g, 60%) as a yellow solid. MS m/z 575.7 $[M+H]^+$.

Compound 10S-e (5.30 g, 9.22 mmol) was dissolved in methanol (60 mL). A solution of HCl in methanol (4M, 10 mL) was added. The reaction mixture was stirred at 40° C. for 3 hours. The reaction was monitored by TLC for completion. It was concentrated under reduced pressure, neutralized with saturated $NaHCO_3$ aq, and extracted with dichloromethane. The combined organic layers were washed with brine, dried over anhydrous sodium sulfate, filtered, and concentrated under reduced pressure to afford compound 10S-f (4.30 g, 98%). MS m/z 475.6 $[M+H]^+$.

Compound 10S-f (200 mg, 0.42 mmol), 1-Boc-3-azetidinone 10S-g (108 mg, 0.63 mmol), and zinc chloride (172 mg, 1.26 mmol) were dissolved in methanol (7 mL). Sodium cyanoborohydride (80 mg, 1.26 mmol) was added. The reaction mixture was stirred at 75° C. for 1 hour. The reaction was monitored by TLC for completion. It was concentrated under reduced pressure. The residue was purified in $SiO_2$ chromatography ($CH_2Cl_2$:$CH_3OH$=20:1, 2% aqueous ammonium hydroxide solution) to afford compound 10S-h (250 mg, yield 94%) as a yellow solid. MS m/z 630.6 $[M+H]^+$.

Compound 10S-h (250 mg, 0.40 mmol) was dissolved in methanol (8 mL). A solution of HCl in 1,4-dioxane (4.0 M, 1.5 mL) was added. The resulted mixture was stirred at 40° C. for 2 hours. The reaction was monitored by TLC for completion. It was cooled to room temperature, and concentrated under reduced pressure. The residue was dissolved in a small amount of methanol, neutralized with aqueous ammonium hydroxide solution, and concentrated under reduced pressure. The residue was purified in $SiO_2$ chromatography ($CH_2Cl_2$:$CH_3OH$=6:1, 2% aqueous ammonium hydroxide solution) to afford compound 10S (173 mg, yield 82%) as a yellow solid. $^1H$ NMR (500 MHz, $CD_3OD$) δ 8.82 (s, 1H), 7.19 (d, J=2.4 Hz, 1H), 6.98 (dd, J=8.7, 2.0 Hz, 1H), 6.84 (d, J=8.8 Hz, 1H), 5.98-5.89 (m, 1H), 4.25 (dd, J=10.6, 2.6 Hz, 1H), 4.06-3.93 (m, 4H), 3.79 (d, J=11.8 Hz, 1H), 3.44-3.37 (m, 1H), 3.14-3.08 (m, 1H), 2.98-2.94 (m, 1H), 2.90-2.85 (m, 1H), 2.78-2.72 (m, 1H), 2.48 (s, 3H), 2.47-2.44 (m, 1H), 2.35 (s, 3H), 2.34-2.27 (m, 2H), 2.24-2.16 (m, 1H), 1.99-1.90 (m, 2H), 1.88-1.77 (m, 3H), 1.68-1.59 (m, 2H) ppm. MS m/z 530.4 $[M+H]^+$.

EXAMPLE 12: PREPARATION OF COMPOUND 11S

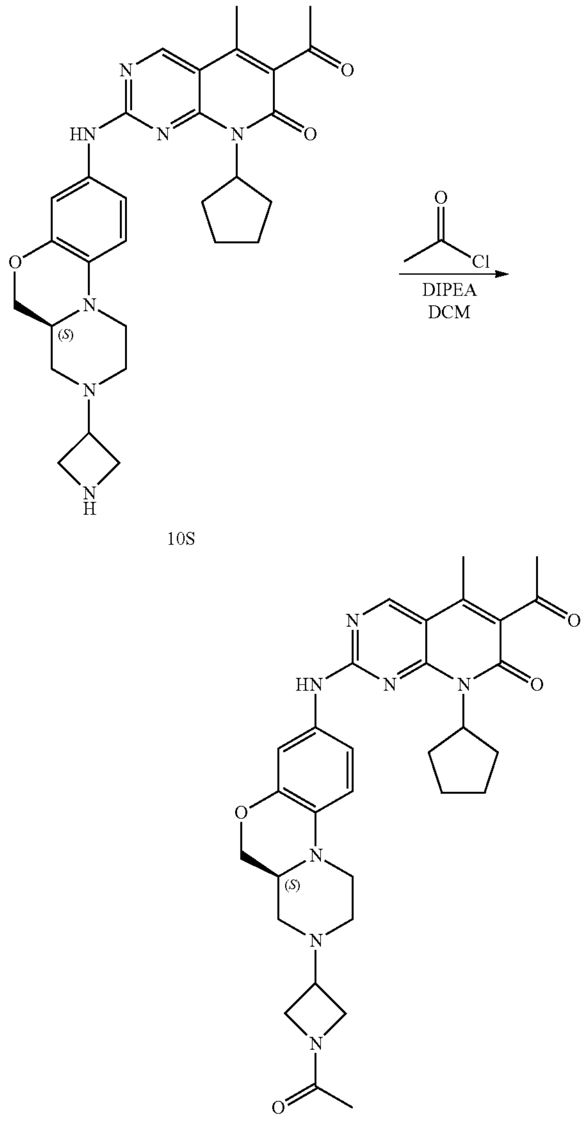

10S

11S

Compound 10S (20 mg, 0.04 mmol) and N,N-diisopropylethylamine (7 mg, 0.06 mmol) were dissolved in dichloromethane (4 mL) followed by the addition of a solution of acetyl chloride (3 mg, 0.04 mmol) in dichloromethane (1 mL) at 0° C. The reaction mixture was stirred at room temperature for 1 hour. It was concentrated under reduced pressure and the residue was purified in $SiO_2$ chromatography ($CH_2Cl_2$:$CH_3OH$=20:1, 2% aqueous ammonium hydroxide solution) to afford compound 11S (20 mg, yield 93%) as yellow solid. $^1H$ NMR (500 MHz, $CD_3OD$) δ 8.82 (s, 1H), 7.19-7.17 (m, 1H), 6.97 (d, J=8.6 Hz, 1H), 6.84 (d, J=8.0 Hz, 1H), 5.99-5.88 (m, 1H), 4.31-4.22 (m, 2H), 4.11 (dd, J=9.1, 5.0 Hz, 1H), 4.08-4.02 (m, 1H), 4.01-3.96 (m, 1H), 3.87 (dd, J=10.3, 5.1 Hz, 1H), 3.78 (d, J=12.1 Hz, 1H), 3.27-3.21 (m, 1H), 3.14-3.08 (m, 1H), 3.03-2.97 (m, 1H), 2.95-2.88 (m, 1H), 2.78-2.71 (m, 1H), 2.48 (s, 3H), 2.35 (s, 3H), 2.34-2.28 (m, 2H), 2.25-2.18 (m, 1H), 1.96-1.92 (m, 2H), 1.90 (s, 3H), 1.88-1.78 (m, 3H), 1.68-1.60 (m, 2H) ppm. MS m/z 572.7 $[M+H]^+$.

EXAMPLE 13: PREPARATION OF COMPOUND 12S

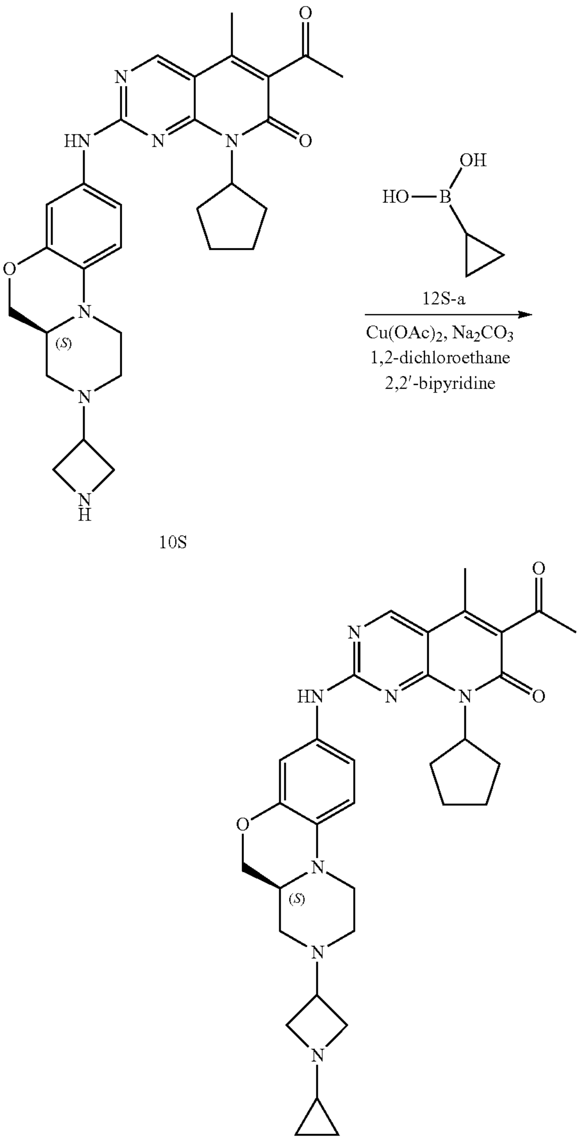

10S

12S

Compound 10S (10 mg, 0.02 mmol), cyclopropylboronic acid 12S-a (3 mg, 0.04 mmol), copper acetate (3 mg, 0.02 mmol), 2,2'-bipyridine (3 mg, 0.081 mmol), and sodium carbonate (3 mg, 0.037 mmol) were dissolved in 1,2-dichloroethane (3 mL). The reaction mixture was heated to 70° C. for 2 hours under air atmosphere. The reaction was monitored by TLC for completion. It was filtered through celite, and filtrate was concentrated under reduced pressure. The residue was purified in $SiO_2$ chromatography ($CH_2Cl_2$: $CH_3OH$=20:1, 2% aqueous ammonium hydroxide solution) to afford compound 12S (1.7 mg, yield 16%) as a yellow solid. MS m/z 570.6 $[M+H]^+$.

EXAMPLE 14: PREPARATION OF COMPOUND 13S

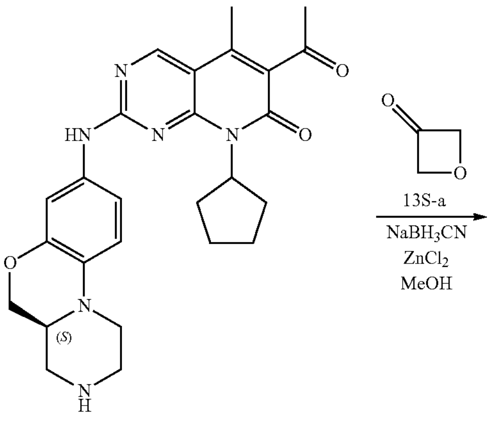

10S-f

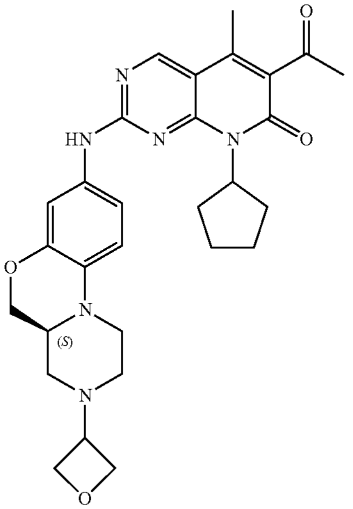

13S

Compound 10S-f (30 mg, 0.06 mmol), 3-oxetanone 13S-a (5 mg, 0.06 mmol), and zinc chloride (17 mg, 0.13 mmol) were dissolved in methanol (5 mL) followed by the addition of sodium cyanoborohydride (12 mg, 0.19 mmol). The reaction mixture was stirred at 75° C. for 1 hour. The reaction was monitored by TLC for completion. It was concentrated under reduced pressure, and the residue was purified in $SiO_2$ chromatography ($CH_2Cl_2$:$CH_3OH$=20:1, 2% aqueous ammonium hydroxide solution) to afford compound 13S (18 mg, yield 54%) as a yellow solid. $^1H$ NMR (500 MHz, DMSO-$d_6$) δ 9.88 (s, 1H), 8.90 (s, 1H), 7.17 (s, 1H), 7.08 (d, J=7.5 Hz, 1H), 6.84 (d, J=8.9 Hz, 1H), 5.88-5.80 (m, 1H), 4.62-4.52 (m, 2H), 4.50-4.40 (m, 2H), 4.24 (dd, J=10.5, 2.6 Hz, 1H), 3.94-3.85 (m, 1H), 3.73 (d, J=11.8 Hz, 1H), 3.50-3.40 (m, 1H), 3.07-2.96 (m, 1H), 2.81 (dd, J=19.5, 10.4 Hz, 2H), 2.67-2.56 (m, 1H), 2.39 (s, 3H), 2.28 (s, 3H), 2.26-2.17 (m, 2H), 2.09-2.00 (m, 1H), 1.88 (s, 2H), 1.76 (s, 2H), 1.64 (t, J=10.6 Hz, 1H), 1.60-1.51 (m, 2H) ppm. MS m/z 531.6 $[M+H]^+$.

EXAMPLE 15: PREPARATION OF COMPOUND 14S

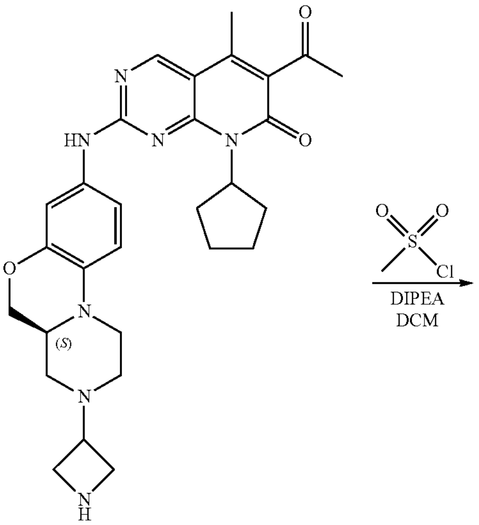

10S

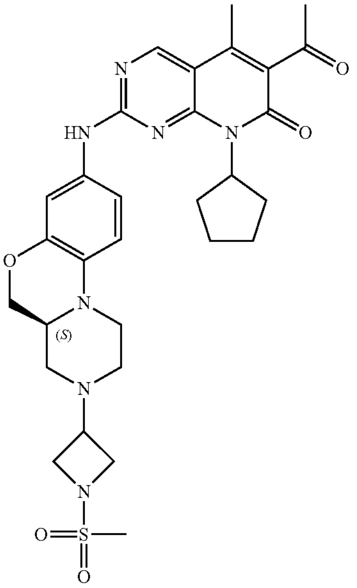

14S

Compound 10S (20 mg, 0.04 mmol) and N,N-diisopropylethylamine (7 mg, 0.06 mmol) were dissolved in dichloromethane (4 mL). A solution of methylsulfonyl chloride (4 mg, 0.04 mmol) in dichloromethane (1 mL) was added at 0° C. The reaction mixture was stirred at room temperature for 1 hour. It was concentrated under reduced pressure, and the residue was purified in $SiO_2$ chromatography ($CH_2Cl_2$: $CH_3OH$=20:1, 2% aqueous ammonium hydroxide solution) to afford compound 14S (21 mg, yield 92%) as a yellow solid. $^1H$ NMR (500 MHz, DMSO-$d_6$) δ 9.88 (s, 1H), 8.90 (s, 1H), 7.18 (d, J=1.9 Hz, 1H), 7.08 (d, J=8.2 Hz, 1H), 6.85 (d, J=8.9 Hz, 1H), 5.89-5.79 (m, 1H), 4.24 (dd, J=10.6, 2.6 Hz, 1H), 3.94-3.71 (m, 6H), 3.25-3.18 (m, 1H), 3.01 (s, 3H), 2.99-2.97 (m, 1H), 2.87 (dd, J=20.6, 10.5 Hz, 2H), 2.64-2.57 (m, 1H), 2.42 (s, 3H), 2.29 (s, 3H), 2.27-2.19 (m, 2H), 2.14-2.06 (m, 1H), 1.93-1.84 (m, 2H), 1.81-1.68 (m, 3H), 1.62-1.55 (m, 2H) ppm. MS m/z 608.8 [M+H]$^+$.

EXAMPLE 16: PREPARATION OF COMPOUND 15S

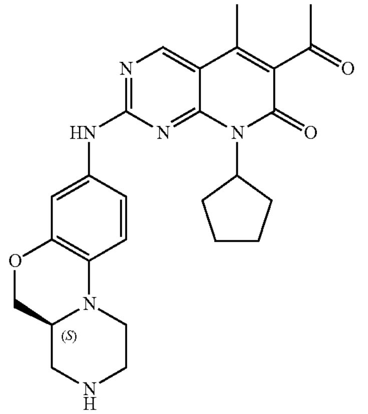

10S-f

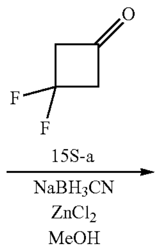

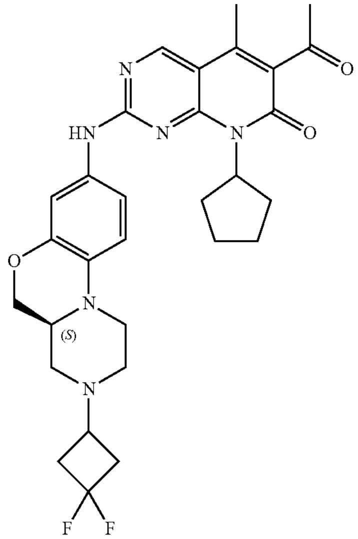

15S

Compound 10S-f (15 mg, 0.03 mmol), 3,3-difluorocyclobutanone 15S-a (5 mg, 0.05 mmol), and zinc chloride (13 mg, 0.09 mmol) were dissolved in methanol (4 mL) followed by the addition of sodium cyanoborohydride (6 mg, 0.09 mmol). The reaction mixture was stirred at 80° C. for 1 hour. The reaction was monitored by TLC for completion. It was concentrated under reduced pressure, and the residue was purified in $SiO_2$ chromatography ($CH_2Cl_2$:$CH_3OH$=30:1) to afford compound 15S (2 mg, yield 11%) as a yellow solid. $^1$H NMR (500 MHz, $CDCl_3$) δ 8.71 (s, 1H), 7.16 (s, 2H), 6.97 (d, J=8.8 Hz, 1H), 6.77 (d, J=8.6 Hz, 1H), 5.89-5.80 (m, 1H), 4.23 (d, J=10.3 Hz, 1H), 4.08-3.97 (m, 1H), 3.78-3.65 (m, 1H), 3.24-3.11 (m, 1H), 3.04-2.92 (m, 1H), 2.87-2.66 (m, 4H), 2.54 (s, 3H), 2.35 (s, 3H), 2.33-2.26 (m, 2H), 2.25-2.13 (m, 1H), 2.00-1.90 (m, 2H), 1.88-1.79 (m, 2H), 1.68-1.51 (m, 6H) ppm. MS m/z 565.6 [M+H]$^+$.

EXAMPLE 17: PREPARATION OF COMPOUND 16S

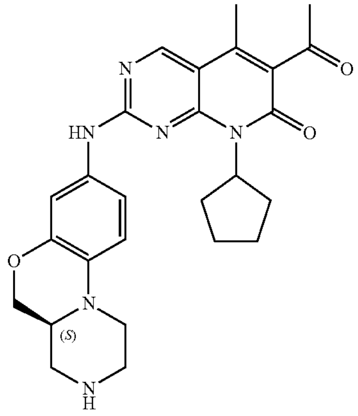

10S-f

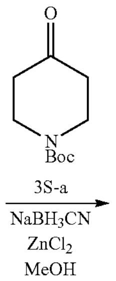

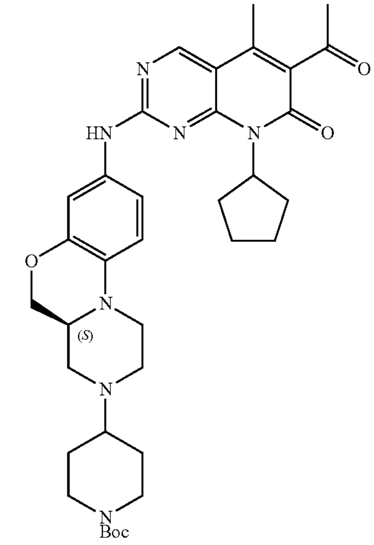

16S-a

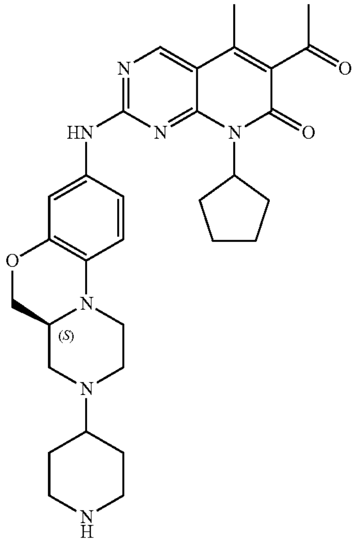

16S-b

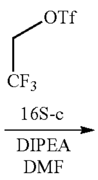

-continued

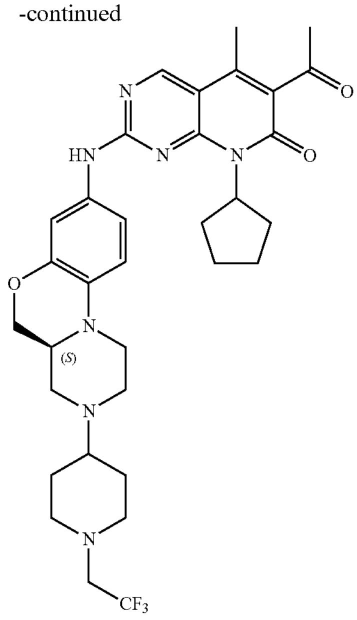

16S

Compound 10S-f (80 mg, 0.17 mmol), N-Boc-4-piperidone 3S-a (50 mg, 0.25 mmol), and zinc chloride (69 mg, 0.51 mmol) were dissolved in methanol (5 mL) followed by the addition of sodium cyanoborohydride (32 mg, 0.51 mmol). The reaction mixture was stirred at 80° C. for 3 hours. The reaction was monitored by TLC for completion. It was concentrated under reduced pressure, and the residue was purified in $SiO_2$ chromatography ($CH_2Cl_2$:$CH_3OH$=15:1) to afford compound 16S-a (91 mg, yield 82%) as a yellow solid. MS m/z 658.7 $[M+H]^+$.

Compound 16S-a (91 mg, 0.14 mmol) was dissolved in methanol (4 mL) followed by the addition of a solution of HCl in 1,4-dioxane (4.0 M, 1 mL). The reaction mixture was stirred at 40° C. for 2 hours. The reaction was monitored by TLC for completion. It was cooled to room temperature, and concentrated under reduced pressure. The residue was dissolved in a small amount of methanol, neutralized with aqueous ammonium hydroxide solution, and concentrated under reduced pressure. The residue was purified in $SiO_2$ chromatography ($CH_2Cl_2$:$CH_3OH$=15:1, 2% aqueous ammonium hydroxide solution) to afford compound 16S-b (58 mg, yield 75%) as a yellow solid. MS m/z 558.6 $[M+H]^+$.

Compound 16S-b (20 mg, 0.04 mmol), compound 16S-c (10 mg, 0.04 mmol), and N,N-diisopropylethylamine (9 mg, 0.07 mmol) were dissolved in N,N-dimethylformamide (2 mL). The reaction mixture was stirred at 80° C. for 3 hours. The reaction was monitored by TLC for completion. It was concentrated under reduced pressure, and the residue was purified in $SiO_2$ chromatography ($CH_2Cl_2$:$CH_3OH$=15:1) to afford compound 16S (16 mg, yield 70%) as a yellow solid. $^1H$ NMR (500 MHz, $CD_3OD$) δ 8.81 (s, 1H), 7.17 (d, J=2.4 Hz, 1H), 6.96 (dd, J=8.7, 2.0 Hz, 1H), 6.82 (d, J=8.9 Hz, 1H), 5.97-5.89 (m, 1H), 4.24 (dd, J=10.5, 2.6 Hz, 1H), 3.97 (dd, J=10.5, 9.0 Hz, 1H), 3.75 (d, J=11.7 Hz, 1H), 3.14-2.98 (m, 7H), 2.75-2.67 (m, 1H), 2.47 (s, 3H), 2.46-2.42 (m, 1H), 2.39 (t, J=11.1 Hz, 2H), 2.35 (s, 3H), 2.33-2.27 (m, 3H), 2.03 (t, J=10.7 Hz, 1H), 1.96-1.78 (m, 6H), 1.68-1.55 (m, 4H) ppm. MS m/z 640.8 $[M+H]^+$.

EXAMPLE 18: PREPARATION OF COMPOUND 17S

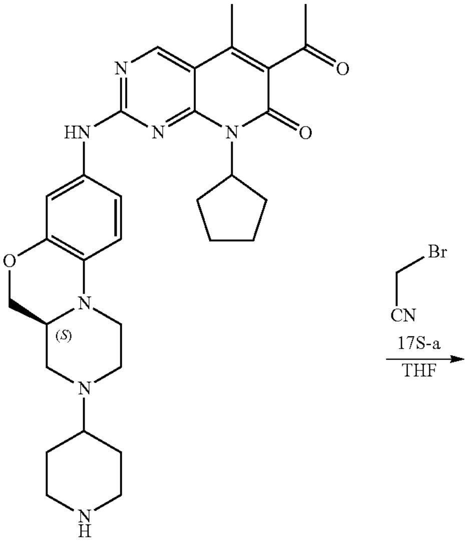

16S-b

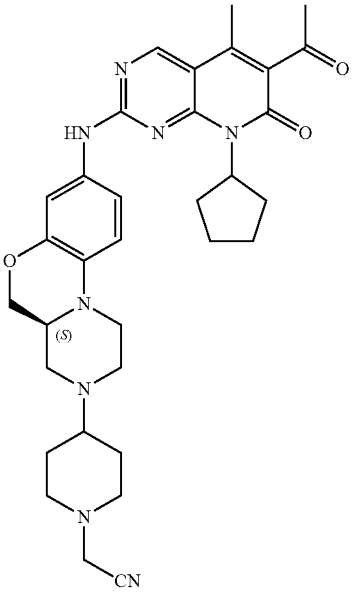

17S

Compound 16S-b (20 mg, 0.04 mmol) and bromoacetonitrile 17S-a (5 mg, 0.04 mmol) were dissolved in THF (2 mL), and the reaction mixture was stirred at room temperature of 3 hours. The reaction was monitored by TLC for completion. It was concentrated under reduced pressure, and the residue was purified in $SiO_2$ chromatography ($CH_2Cl_2$:$CH_3OH$=20:1) to afford compound 17S (12 mg, yield 56%) as a yellow solid. $^1H$ NMR (500 MHz, DMSO-$d_6$) δ 9.87 (s, 1H), 8.90 (s, 1H), 7.16 (d, J=2.0 Hz, 1H), 7.07 (d, J=8.0 Hz, 1H), 6.82 (d, J=8.9 Hz, 1H), 5.90-5.77 (m, 1H), 4.24 (dd, J=10.6, 2.4 Hz, 1H), 3.90 (dd, J=10.5, 9.0 Hz, 1H), 3.72-3.66 (m, 3H), 3.01-2.89 (m, 3H), 2.83 (d, J=11.2 Hz, 2H), 2.58-2.52 (m, 1H), 2.41 (s, 3H), 2.35-2.31 (m, 1H), 2.29 (s, 3H), 2.26-2.20 (m, 3H), 2.16 (t, J=10.8 Hz, 2H), 1.93-1.84

(m, 3H), 1.82-1.73 (m, 4H), 1.62-1.54 (m, 2H), 1.51-1.39 (m, 2H) ppm. MS m/z 597.8 $[M+H]^+$.

EXAMPLE 19: PREPARATION OF COMPOUND 18S

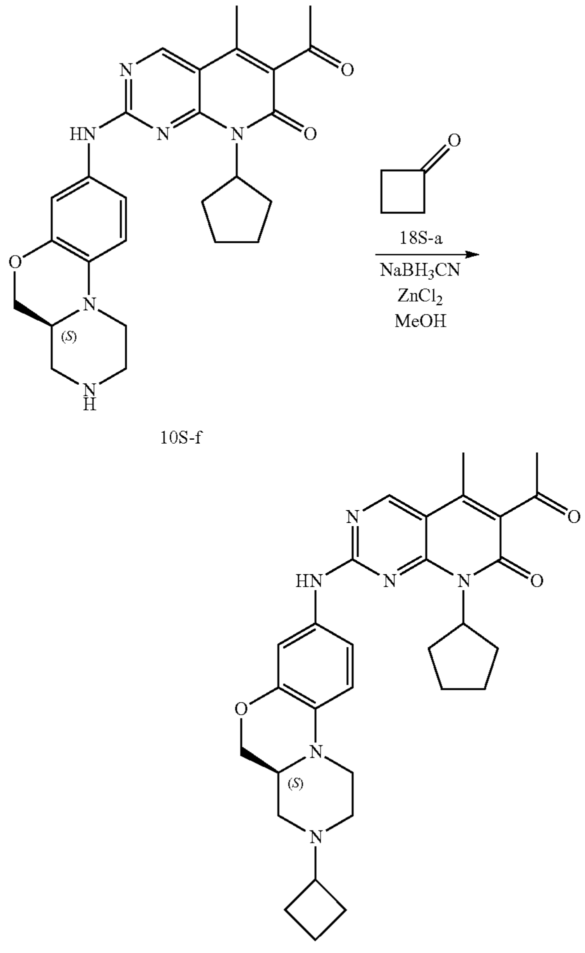

10S-f

18S compound 10S-f (15 mg, 0.03 mmol), cyclobutanone 18S-a (3 mg, 0.05 mmol), and zinc chloride (13 mg, 0.09 mmol) were dissolved in methanol (4 mL) followed by the addition of sodium cyanoborohydride (6 mg, 0.09 mmol). The reaction mixture was stirred at 80° C. for 1 hour. The reaction was monitored by TLC for completion. It was concentrated under reduced pressure, and the residue was purified in $SiO_2$ chromatography ($CH_2Cl_2$:$CH_3OH$=15:1) to afford compound 18S (11 mg, yield 66%) as a yellow solid. $^1$H NMR (500 MHz, DMSO-$d_6$) δ 9.87 (s, 1H), 8.90 (s, 1H), 7.16 (d, J=2.0 Hz, 1H), 7.07 (d, J=7.8 Hz, 1H), 6.82 (d, J=8.9 Hz, 1H), 5.87-5.78 (m, 1H), 4.25 (dd, J=10.6, 2.6 Hz, 1H), 3.89 (dd, J=10.5, 9.1 Hz, 1H), 3.70 (d, J=11.6 Hz, 1H), 2.99-2.92 (m, 1H), 2.86 (d, J=11.7 Hz, 1H), 2.81 (d, J=10.2 Hz, 1H), 2.77-2.69 (m, 1H), 2.59-2.52 (m, 1H), 2.41 (s, 3H), 2.29 (s, 3H), 2.26-2.19 (m, 2H), 2.02-1.73 (m, 8H), 1.69-1.50 (m, 5H), 1.27-1.22 (m, 1H) ppm. MS m/z 529.7 $[M+H]^+$.

EXAMPLE 20: PREPARATION OF COMPOUND 19S

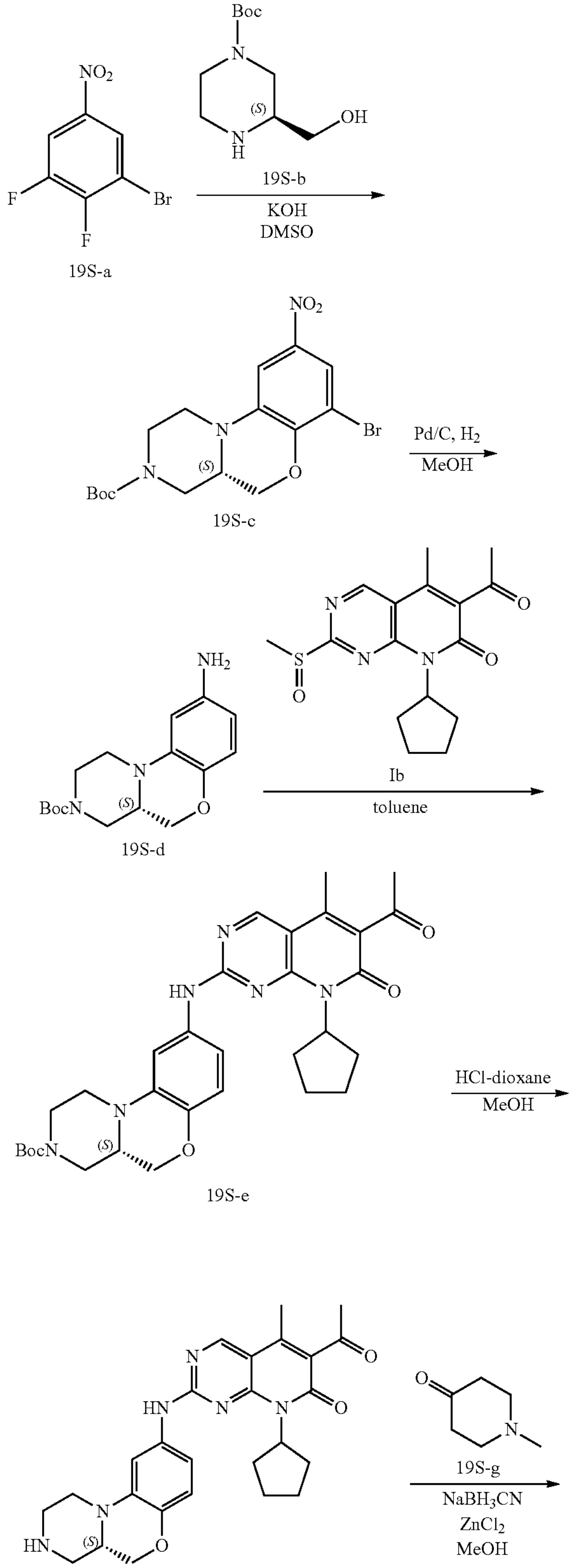

19S-a 19S-c 19S-d 19S-e 19S-f

-continued

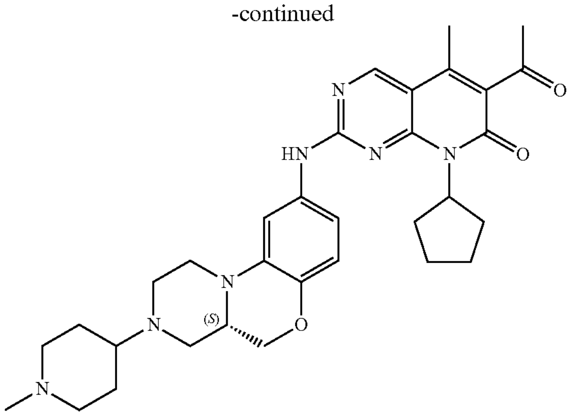

19S

Compound 19S-a (3.0 g, 12.61 mmol), compound 19S-b (2.73 g, 12.61 mmol), and KOH (2.12 g, 37.82 mmol) were dissolved in dimethyl sulfone (40 mL). The reaction mixture was stirred at room temperature for 3 hours, and stirred at 60° C. for 3 hours. It was cooled to room temperature, poured into ice water, and stirred for 1 hour. The mixture was extracted with dichloromethane (3×40 mL), washed with brine, dried over anhydrous sodium sulfate, filtered, and concentrated under reduced pressure. The residue was purified in $SiO_2$ chromatography (petroleum ether:EtOAc: $CH_2Cl_2$=15:1:1) to afford compound 19S-c (1.07 g, yield 20%) as a yellow solid.

To methanol (6 mL) was added compound 19S-c (500 mg, 1.21 mmol) and Pd on carbon (10%, 150 mg). The reaction mixture was stirred under 1 atmospheric pressure of $H_2$ at room temperature for 1 hour. The reaction was monitored by TLC for completion. It was filtered through celite, and the filtrate was concentrated under reduced pressure. The residue was purified in $SiO_2$ chromatography ($CH_2Cl_2$: EtOAc=4:1) to afford compound 19S-d (235 mg, yield 64%) as a gray solid. MS m/z 306.4 $[M+H]^+$.

A mixture of compound 19S-d (235 mg, 0.77 mmol) and compound Ib (257 mg, 0.77 mmol) in toluene (6 mL) in a sealed tube was heated to 100° C. and stirred for 5 hours. The reaction was monitored by TLC for completion. It was cooled to room temperature, and concentrated under reduced pressure. The residue was purified in $SiO_2$ chromatography ($CH_2Cl_2$:EtOAc=2:1) to afford compound 19S-e (200 mg, yield 45%) as a yellow solid. MS m/z 575.8 $[M+H]^+$.

Compound 19S-e (200 mg, 0.35 mmol) was dissolved in methanol (2 mL) followed by the addition of a solution of HCl in 1,4-dioxane (4.0 M, 2 mL). The reaction mixture was stirred at 40° C. for 2 hours. The reaction was monitored by TLC for completion. It was cooled to room temperature, and concentrated under reduced pressure. The residue was dissolved in a small amount of methanol, neutralized with aqueous ammonium hydroxide solution, and concentrated under reduced pressure. The residue was purified in $SiO_2$ chromatography ($CH_2Cl_2$:$CH_3OH$=15:1, 2% aqueous ammonium hydroxide solution) to afford compound 19S-f (140 mg, yield 85%) as a yellow solid.

Compound 19S-f (20 mg, 0.04 mmol), compound 19S-g (5 mg, 0.04 mmol), and zinc chloride (12 mg, 0.08 mmol) were dissolved methanol (5 mL) followed by the addition of sodium cyanoborohydride (8 mg, 0.13 mmol). The reaction mixture was stirred at 75° C. for 1 hour. The reaction was monitored by TLC for completion. It was concentrated under reduced pressure, and the residue was purified in $SiO_2$ chromatography ($CH_2Cl_2$:$CH_3OH$=20:1, 2% aqueous ammonium hydroxide solution) to afford compound 19S (10.44 mg, yield 43%) as a yellow solid. $^1H$ NMR (500 MHz, $CDCl_3$) δ 8.71 (s, 1H), 7.13 (s, 1H), 7.09 (s, 1H), 6.77 (s, 2H), 5.92-5.83 (m, 1H), 4.19 (dd, J=10.5, 2.7 Hz, 1H), 4.03-3.95 (m, 1H), 3.65 (d, J=11.2 Hz, 1H), 3.22-3.15 (m, 2H), 3.11-3.01 (m, 1H), 2.99 (d, J=10.2 Hz, 1H), 2.90-2.78 (m, 2H), 2.54 (s, 3H), 2.50-2.45 (m, 1H), 2.44-2.37 (m, 3H), 2.36 (s, 3H), 2.32-2.22 (m, 4H), 2.11-2.02 (m, 2H), 2.01-1.71 (m, 10H) ppm. MS m/z 572.7 $[M+H]^+$.

EXAMPLE 21: PREPARATION OF COMPOUND 20S

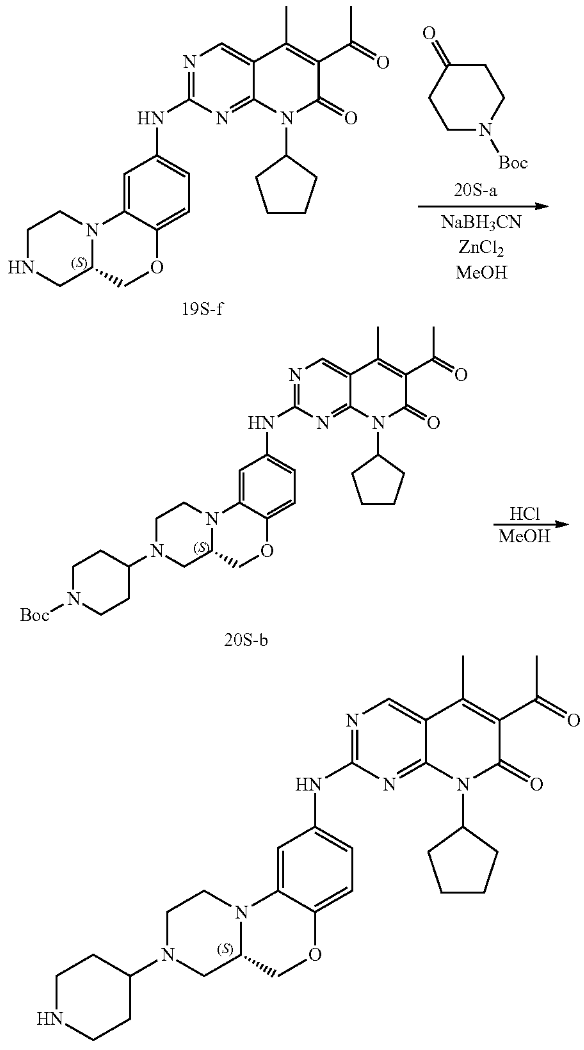

Compound 19S-f (30 mg, 0.06 mmol), N-Boc-4-piperidone (13 mg, 0.06 mmol), and zinc chloride (17 mg, 0.13 mmol) were dissolved in methanol (5 mL) followed by the addition of sodium cyanoborohydride (12 mg, 0.19 mmol). The reaction mixture was stirred at 75° C. for 1 hour. The reaction was monitored by TLC for completion. It was concentrated under reduced pressure, and the residue was purified in $SiO_2$ chromatography ($CH_2Cl_2$:$CH_3OH$=20:1, 2% aqueous ammonium hydroxide solution) to afford compound 20S-b (25 mg, yield 60%) as a yellow solid. MS m/z 658.3 $[M+H]^+$.

Compound 20S-b (25 mg, 0.04 mmol) was dissolved methanol (2 mL) followed by the addition of a solution of HCl in 1,4-dioxane (4.0 M, 1.5 mL). The reaction mixture was stirred at 40° C. for 2 hours. The reaction was monitored by TLC for completion. It was cooled to room temperature, and concentrated under reduced pressure. The residue was dissolved in amount of methanol, neutralized with aqueous ammonium hydroxide solution, and concentrated under reduced pressure. The residue was purified in $SiO_2$ chromatography ($CH_2Cl_2$:$CH_3OH$=15:1, 2% aqueous ammonium hydroxide solution) to afford compound 20S (12.8 mg, yield 60%) as a yellow solid. $^1H$ NMR (500 MHz, $CD_3OD$) δ 8.82 (s, 1H), 7.17 (d, J=2.0 Hz, 1H), 6.88-6.81 (m, 1H), 6.69 (d, J=8.5 Hz, 1H), 6.01-5.90 (m, 1H), 4.23 (dd, J=10.5, 2.6 Hz, 1H), 3.99-3.91 (m, 1H), 3.73 (d, J=11.5 Hz, 1H), 3.41-3.35 (m, 3H), 3.13-3.06 (m, 2H), 3.01 (d, J=10.5 Hz, 1H), 2.95-2.86 (m, 2H), 2.79-2.72 (m, 1H), 2.62-2.55 (m, 1H), 2.47 (s, 3H), 2.35 (s, 3H), 2.33-2.23 (m, 2H), 2.10-2.01 (m, 3H), 2.01-1.88 (m, 2H), 1.81 (d, J=4.8 Hz, 2H), 1.75-1.65 (m, 2H), 1.63-1.55 (m, 2H) ppm. MS m/z 558.6 $[M+H]^+$.

EXAMPLE 22: PREPARATION OF COMPOUND 21S

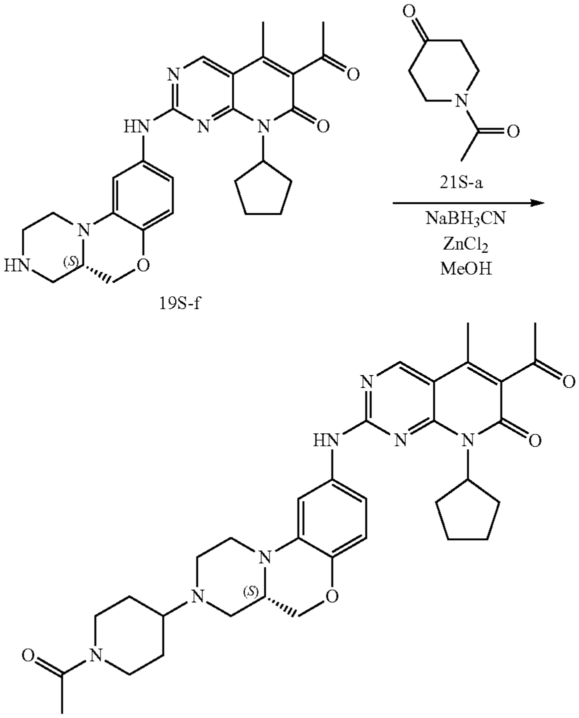

19S-f

21S

Compound 19S-f (20 mg, 0.04 mmol), compound 21S-a (6 mg, 0.04 mmol), and zinc chloride (12 mg, 0.08 mmol) were dissolved methanol (5 mL) followed by the addition of sodium cyanoborohydride (8 mg, 0.13 mmol). The reaction mixture was stirred at 75° C. for 1 hour. The reaction was monitored by TLC for completion. It was concentrated under reduced pressure, and the residue was purified in $SiO_2$ chromatography ($CH_2Cl_2$:$CH_3OH$=20:1, 2% aqueous ammonium hydroxide solution) to afford compound 21S (15.30 mg, yield 60%) as a yellow solid. $^1H$ NMR (500 MHz, $CDCl_3$) δ 8.71 (s, 1H), 7.15 (s, 1H), 7.11 (s, 1H), 6.86-6.72 (m, 2H), 5.93-5.71 (m, 1H), 4.74-4.65 (m, 1H), 4.21 (d, J=9.6 Hz, 1H), 4.06-3.96 (m, 1H), 3.90 (d, J=12.8 Hz, 1H), 3.76-3.68 (m, 1H), 3.28-2.80 (m, 5H), 2.69-2.55 (m, 2H), 2.54 (s, 3H), 2.35 (s, 3H), 2.34-2.25 (m, 2H), 2.10 (s, 3H), 2.04-1.77 (m, 7H), 1.78-1.54 (m, 5H) ppm. MS m/z 600.8 $[M+H]^+$.

EXAMPLE 23: PREPARATION OF COMPOUND 1R

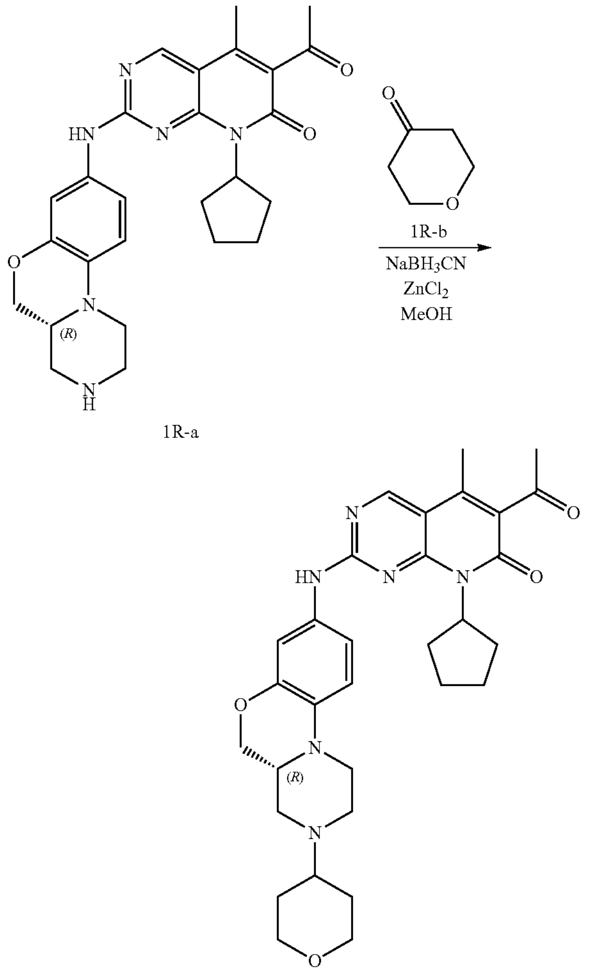

1R-a

1R

Compound 1R-a was prepared by following the method in patent WO2017101763.

Compound 1R-a (30 mg, 0.06 mmol), tetrahydro-4H-pyran-4-one 1R-b (9 mg, 0.06 mmol), and zinc chloride (17 mg, 0.13 mmol) were dissolved in methanol (5 mL) followed by the addition of sodium cyanoborohydride (12 mg, 0.19 mmol). The reaction mixture was stirred at 75° C. for 1 hour. The reaction was monitored by TLC for completion. It was concentrated under reduced pressure, and the residue was purified in $SiO_2$ chromatography ($CH_2Cl_2$:$CH_3OH$=20:1, 2% aqueous ammonium hydroxide solution) to afford compound 1R (15 mg, yield 42%) as a yellow solid. $^1H$ NMR (500 MHz, DMSO-$d_6$) δ 9.88 (s, 1H), 8.90 (s, 1H), 7.16 (d, J=2.0 Hz, 1H), 7.07 (d, J=7.7 Hz, 1H), 6.82 (d, J=8.9 Hz, 1H), 5.88-5.80 (m, 1H), 4.24 (dd, J=10.5, 2.4 Hz, 1H), 4.02-3.85 (m, 3H), 3.71 (d, J=11.7 Hz, 1H), 3.33-3.23 (m, 2H), 3.06-2.86 (m, 3H), 2.63-2.54 (m, 2H), 2.43 (s, 3H), 2.29 (s, 3H), 2.26-2.17 (m, 2H), 2.01-1.85 (m, 4H), 1.82-1.68 (m, 4H), 1.65-1.52 (m, 2H), 1.51-1.34 (m, 2H) ppm. MS m/z 559.8 $[M+H]^+$.

EXAMPLE 24: PREPARATION OF COMPOUND 3R

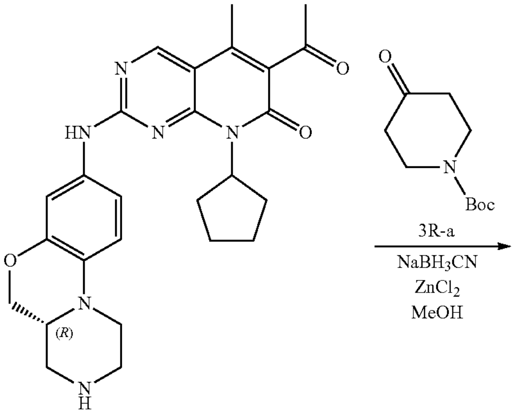

1R-a

-continued

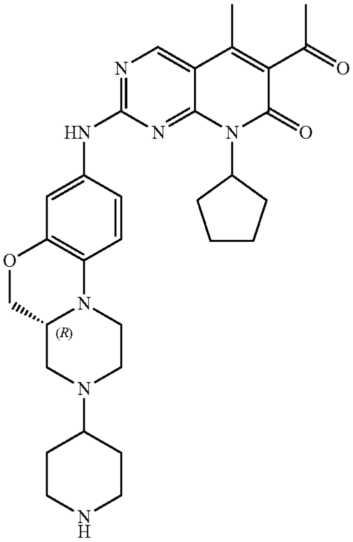

3R

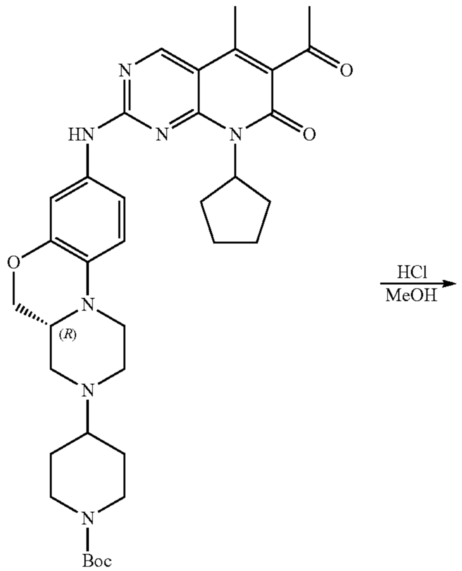

3R-b

Compound 1R-a (30 mg, 0.06 mmol), 1-Boc-4-piperidone 3R-a (12 mg, 0.06 mmol), and zinc chloride (17 mg, 0.13 mmol) were dissolved in methanol (5 mL) followed by the addition of sodium cyanoborohydride (12 mg, 0.19 mmol). The reaction mixture was stirred at 75° C. for 1 hour. The reaction was monitored by TLC for completion. It was concentrated under reduced pressure, and the residue was purified in $SiO_2$ chromatography ($CH_2Cl_2$:$CH_3OH$=20:1, 2% aqueous ammonium hydroxide solution) to afford compound 3R-b (25 mg, yield 60%) as a yellow solid. MS m/z 658.3 $[M+H]^+$.

Compound 3R-b (25 mg, 0.04 mmol) was dissolved in methanol (2 mL) followed by the addition of a solution of HCl in 1,4-dioxane (4.0 M, 1.5 mL). The reaction mixture was stirred at 40° C. for 2 hours. The reaction was monitored by TLC for completion. It was concentrated under reduced pressure. The resulted mixture was dissolved in amount of methanol, neutralized with aqueous ammonium hydroxide solution, and concentrated under reduced pressure. The residue was purified in $SiO_2$ chromatography ($CH_2Cl_2$:$CH_3OH$=15:1, 2% aqueous ammonium hydroxide solution) to afford compound 3R (9 mg, yield 42%) as a yellow solid. $^1H$ NMR (500 MHz, MeOD-$d_4$) δ 8.72 (s, 1H), 7.07 (d, J=2.0 Hz, 1H), 6.86 (dd, J=9.0, 2.0 Hz, 1H), 6.73 (d, J=9.0 Hz, 1H), 5.92-5.75 (m, 1H), 4.14 (dd, J=10.5, 2.6 Hz, 1H), 3.98-3.82 (m, 1H), 3.66 (d, J=11.6 Hz, 1H), 3.16-3.06 (m, 2H), 3.04-2.87 (m, 3H), 2.66-2.55 (m, 3H), 2.40 (s, 3H), 2.36-2.31 (m, 1H), 2.25 (s, 3H), 2.24-2.15 (m, 2H), 1.95 (t, J=21.3, 10.6 Hz, 2H), 1.92-1.78 (m, 4H), 1.77-1.67 (m, 2H), 1.61-1.49 (m, 2H), 1.49-1.37 (m, 2H) ppm. MS m/z 558.6 $[M+H]^+$.

EXAMPLE 25: PREPARATION OF COMPOUND 5R

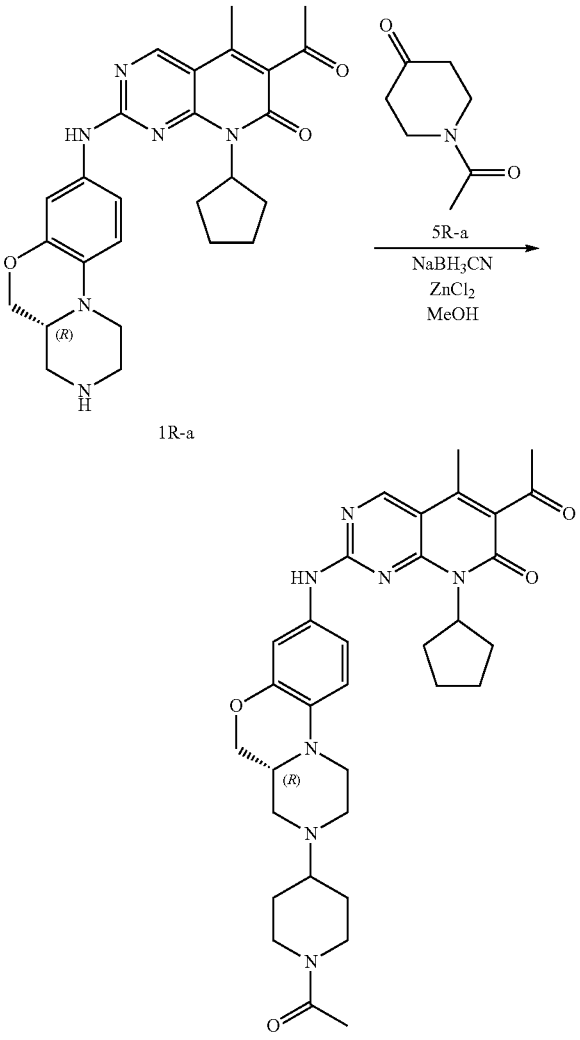

1R-a

5R

Compound 1R-a (30 mg, 0.06 mmol),N-acetyl-4-piperidone 5R-a (9 mg, 0.06 mmol), and zinc chloride (17 mg, 0.13 mmol) were added to methanol (5 mL) followed by the addition of sodium cyanoborohydride (12 mg, 0.19 mmol). The resulted reaction mixture was stirred at 75° C. for 1 hour. The reaction was monitored by TLC for completion. It was concentrated under reduced pressure, and the residue was purified in $SiO_2$ chromatography ($CH_2Cl_2$:$CH_3OH$=20:1, 2% $NH_4OH$ aq.) to afford compound 5R (14 mg, yield 37%) as a yellow solid. $^1H$ NMR (500 MHz, $CD_3OD$) δ 8.81 (s, 1H), 7.17 (d, J=2.4 Hz, 1H), 6.96 (dd, J=8.7, 1.9 Hz, 1H), 6.82 (d, J=8.9 Hz, 1H), 5.99-5.87 (m, 1H), 4.53 (d, J=12.4 Hz, 1H), 4.24 (d, J=9.8 Hz, 1H), 4.05-3.92 (m, 2H), 3.76 (d, J=10.7 Hz, 1H), 3.15-2.95 (m, 4H), 2.76-2.55 (m, 3H), 2.54-2.50 (m, 1H), 2.47 (s, 3H), 2.35-2.26 (m, 5H), 2.11-2.02 (m, 4H), 2.02-1.88 (m, 4H), 1.88-1.77 (m, 2H), 1.70-1.58 (m, 2H), 1.55-1.48 (m, 1H), 1.43-1.36 (m, 1H) ppm. MS m/z 600.8 $[M+H]^+$.

EXAMPLE 26

1) CDK2, CDK4 and CDK6 Kinase Activity Inhibition Assay

In vitro enzymatic activity of the CDK isoforms CDK2/CycA2, CDK4/CycD3 and CDK6/cycD3 were measured using caliper mobility shift assay. Dissolve the compounds in DMSO and dilute them with corresponding kinase buffer (CDK2/CycA2 and CDK6/CycD3 were assayed with buffer conditions of 50 mM HEPES (pH 7.5), 10 mM $MgCl_2$, 0.0015% Brij-35 and 2 mM dithiothreitol; CDK4/CycD3 was assayed with buffer condition of 20 mM HEPES (pH 7.5), 10 mM $MgCl_2$, 0.01% Triton X-100 and 2 mM dithiothreitol). Add 5 μl of compound (10% DMSO) with 5 times the final concentration of the reaction to a 384-well plate. Add 10 μl of 2.5 times enzyme solution and incubate at room temperature for 10 minutes, then add 10 μl of 2.5 times substrate solution (for each isoform, dosage of enzyme and ATP are CDK2/CycA2 12 nM, ATP Km 39 μM; CDK4/CycD3 10 nM, ATP Km 221 μM; CDK6/cycD3 15 nM, ATP Km 800 μM). After incubating for 60 min, 180 min and 60 min of CDK2, CDK4 and CDK6 respectively at 28° C., reactions were terminated with 25 μl stop solution (100 mM HEPES (pH 7.5), 0.015% Brij-35, 0.2% Coating Reagent #3, 50 mM EDTA). Collect conversion data on Caliper EZ Reader II (Caliper Life Sciences). Convert the conversion rate into inhibition rate data (% inhibition rate=(max−conversion rate)/(max−min)*100). Max refers to the conversion rate of DMSO control, and min refers to the conversion rate of inactive control. Draw a curve with the concentration and inhibition rate of the compound as abscissa and ordinate, and use XLFit excel add-in version 4.3.1 software to fit the curve and calculate $IC_{50}$. The activities of some representative compounds are shown in Table 1.

2) TRKA Kinase Activity Inhibition Assay

TRKA protein kinase activity was measured by caliper mobility shift assay. Compounds were dissolved in DMSO to make up 10 mM stock solutions. Prepare 1× kinase reaction buffer to serially dilute compounds. 250 nL 100× final concentration of the test compounds were transferred to destination plate 3573 by dispenser Echo 550. Prepare a 2.5× final concentration of kinase solution with 1× kinase buffer. Add 10 μL of 2.5× final kinase solution to compound wells and positive control wells; add 10 μL of 1× kinase buffer to negative control wells. Centrifuge at 1000 rpm for 30 s, shake and mix the reaction plate and incubate at room temperature for 10 min. Prepare a mixture of ATP and kinase substrate solution at 5/3× final concentration with 1× kinase buffer. The reaction was initiated by adding 15 μL of the mixed solution. Centrifuge the 384-well plate at 1000 rpm for 30 s, shake and mix well, and incubate at room temperature for the corresponding time. Add 30 μL of stop solution to stop the kinase reaction, centrifuge at 1000 rpm for 30 s, mix by shaking, and read the conversion rate data with Caliper EZ Reader. Convert conversion to inhibition data (% inhibition=(max DMSO well conversion−sample well conversion)/(max DMSO well conversion−min negative control conversion)*100). Wherein max refers to the conversion rate of the DMSO control, and min refers to the conversion rate of the non-enzymatic control. Draw a curve with the concentration and inhibition rate of the compound as abscissa and ordinate, and use XLFit excel add-in version 4.3.1 software to fit the curve and calculate $IC_{50}$. The activities of some representative compounds are shown in Table 1.

3) CDK5, CDK9 and CDK16 Kinase Activity Inhibition Assay

CDK5/p35NCK, CDK9/CycT1 and CDK16/CycY protein kinase activities were determined using the ADP-Glo Kinase Assay. Dilute the positive compound and the test compound (10 mM stock solution) 25-fold with 100% DMSO, make a 4-fold serial dilution in a 96-well dilution plate, and add 1 μL of the compound to 49 μL of kinase reaction buffer (1 mM Tris, 20 mM $MgCl_2$, 0.10% BSA and 0.5 mM DTT) on a microplate shaker for 20 min. Transfer 2 μL of 2× kinase to the 384-well reaction plate, add 1 μL of the test compound to the 384-well reaction plate, centrifuge at 1000 rpm/min for 1 min, and incubate at 25° C. for 10 min. Transfer 1 μL of the 4× substrate mix to the 384-well reaction plate, centrifuge at 1000 rpm/min for 1 min, and incubate at 25° C. for 60 min. Transfer 4 μL of ADP-Glo to the 384-well reaction plate to centrifuge at 1000 rpm/min for 1 min, and incubate at 25° C. for 40 min. Transfer 8 μL of detection solution to the 384-well reaction plate to centrifuge at 1000 rpm/min for 1 min, and incubate at 25° C. for 40 min. The RLU (Relative luminescence unit) signal was read using a Biotek multifunctional plate reader. Signal intensity is used to characterize the degree of kinase activity. Compound inhibition rate data: % inhibition rate=[1−(compound mean RLU−positive control mean RLU)/(negative control mean RLU−positive control mean RLU)]*100. Taking the log value of the concentration as the X axis and the percentage inhibition rate as the Y axis, the log(inhibitor) vs. response-Variable slope of the analysis software GraphPad Prism 5 was used to fit the dose-response curve to obtain the $IC_{50}$ value of each compound on the enzyme activity. The activities of some representative compounds are shown in Table 1.

TABLE 1

CDK2, CDK4, CDK6, CDK5, CDK9, CDK16 and TRKA kinase inhibitory activity ($IC_{50}$, nM)

| Compound | CDK2 | CDK4 | CDK6 | CDK5 | CDK9 | CDK16 | TRKA |
|---|---|---|---|---|---|---|---|
| Ref-A[a] | ≥2000 | <10 | <20 | <50 | ≥300 | ≥2000 | ≥400 |
| 1S[a] | <100 | <10 | <20 | | | | |
| 1R | <100 | <10 | <20 | <100 | <50 | <100 | <10 |
| 2S[a] | <100 | <10 | <10 | <50 | <20 | <100 | <10 |
| 2R | <100 | <10 | <10 | | | | <10 |
| 3S | <100 | <10 | <10 | <100 | <20 | <50 | <10 |
| 3R | <100 | <10 | <10 | | | | |
| 4S | <100 | <10 | <10 | <100 | <20 | <100 | <10 |
| 5S | <100 | <10 | <10 | | | | |
| 5R | <100 | <10 | <20 | <200 | <50 | <200 | <10 |
| 6S | <100 | <10 | <10 | | | | |
| 7S | <100 | <10 | <10 | <100 | <50 | <100 | <10 |
| 8S | <500 | <20 | <100 | | | | |
| 9S | <500 | <10 | <50 | | | | |
| 10S | <100 | <10 | <10 | | | | |
| 11S | <100 | <10 | <20 | | | | <10 |
| 12S | <100 | <10 | <10 | | | | |
| 13S | <100 | <10 | <20 | | | | |
| 14S | <100 | <10 | <20 | | | | |
| 15S | <1000 | <50 | | | | | <100 |
| 16S | <500 | <10 | | | | | |
| 17S | <100 | <10 | | | | | |
| 18S | <500 | <10 | | | | | |
| 19S | <500 | <100 | | | | | |
| 20S | <500 | | | | | | |
| 21S | <500 | | | | | | |

[a]Compound is hydrochloride salt.

The results show that the compound of the invention has the same CDK4 and CDK6 inhibitory activity as the CDK4/6 selective inhibitor Palbociclib (Ref-A) in the prior art, and also has strong inhibitory activity on CDK2, CDK5, CDK9, CDK16 and TRKA kinases, and is a multi-target kinase inhibitor.

EXAMPLE 27 PHARMACOKINETIC STUDY IN RATS

Instruments: XEVO TQ-S LC/MS instrument produced by Waters. All measurement data is collected and processed by Masslynx V4.1 software, and the data is calculated and processed by Microsoft Excel. Using WinNonLin 8.0 software, the statistical moment method was used to calculate the pharmacokinetic parameters. Mainly include kinetic parameters $T_{max}$, $T_{1/2}$, $C_{max}$, $AUC_{last}$ etc. Column: ACQUITY UPLC BEH C18 (2.1 mm×50 mm, 1.7 μm); column temperature 40° C.; mobile phase A is water (0.1% formic acid), mobile phase B is acetonitrile, flow rate is 0.350 ml/min, gradient elution is adopted, the elution gradient is 0.50 min: 10% B; 1.50 min: 10% B; 2.30 min: 95% B; 2.31 min: 10% B; 3.00 min: stop. Injection volume: 5 μL.

Animals: 3 male SD rats with a weight range of 200-220 g. After purchase, they will be kept in the laboratory of the Experimental Animal Center for 2 days and then used. They will be fasted for 12 hours predose and 4 hours after dosing. Drinking water is free during the test. After the rats were gavage, blood samples were taken according to the established time point.

Solvent: 0.5% Methylcellulose (aqueous solution containing 0.4% Tween 80 and 1% ethanol). Preparation of the solution for intragastrical administration: accurately weigh the compound, add it to the solvent, and use ultrasound at room temperature for 5 minutes to completely dissolve the drug, and prepare a 0.3 mg/ml medicinal solution.

Pharmaceutical samples: representative compounds of the structure shown in the patented formula (I) of the present invention, generally, multiple samples with similar structures (with a molecular weight difference of more than 2 units) are taken, accurately weighed, and administered together (cassette PK). In this way, multiple compounds can be screened at the same time and their oral absorption rates can be compared. A single administration was also used to study the pharmacokinetics of the drug sample in rats.

After intragastrical administration, blood was taken from the orbit at 0.25, 0.5, 1, 2, 4, 9, 12 and 24 hours, and placed in a plastic centrifuge tube pretreated with sodium heparin. After centrifugation, the supernatant plasma was used for LC-MS/MS analysis.

Accurately weigh the compounds to prepare different concentrations, perform quantitative analysis on mass spectrometry to establish a standard curve, and then test the concentration of the above-mentioned compound in the plasma to obtain the compound concentration at different time points. All measurement data are collected and processed by relevant software, and the statistical moment method is used to calculate the pharmacokinetic parameters (mainly including kinetic parameters $T_{max}$, $T_{1/2}$, $C_{max}$, $AUC_{last}$ etc). The kinetic parameters of some representative compounds are shown in Table 2.

TABLE 2

Pharmacokinetic parameters of the compounds in SD rats

| Compound s | Oral dosage | $T_{max}$ (h) | $T_{1/2}$ (h) | $C_{max}$ (ng/mL) | $AUC_{(0-24)}$ (ng/mL*h) |
|---|---|---|---|---|---|
| Ref-B[a] | 3 mg/kg | 3.33 | 6.71 | 13.92 | 108.22 |
| 1R | 3 mg/kg | 2.00 | 2.96 | 43.35 | 273.69 |
| 1S[a] | 3 mg/kg | 3.00 | 6.41 | 37.27 | 191.95 |
| 2S[a] | 3 mg/kg | 13.33 | >12 | 114.03 | 1910.48 |
| 3S | 3 mg/kg | 5.33 | 5.68 | 85.70 | 1225.68 |
| 4S | 3 mg/kg | 12.00 | 10.74 | 250.01 | 3772.01 |
| 5R | 3 mg/kg | 6.67 | 2.91 | 438.45 | 4350.29 |
| 5S | 3 mg/kg | 6.00 | 2.18 | 266.46 | 2478.44 |
| 6S | 3 mg/kg | 6.67 | 4.31 | 54.90 | 661.99 |
| 7S | 3 mg/kg | 9.33 | 3.19 | 133.08 | 1938.26 |
| 9S | 3 mg/kg | 12.00 | 15.6 | 42.54 | 697.09 |
| 11S | 3 mg/kg | 2.00 | 2.61 | 424.29 | 2996.59 |
| 13S | 3 mg/kg | 1.83 | 1.95 | 169.07 | 860.14 |
| 14S | 3 mg/kg | 1.33 | 1.84 | 441.8 | 2032.14 |

[a]Compound is hydrochloride salt.

The results show that the oral absorption ability of the compounds in this invention in rats is significantly better than that of the compound 7S (Ref-B) in the prior patent (WO2017101763).

The structures of Ref-A and Ref-B are as follows:

Ref-A

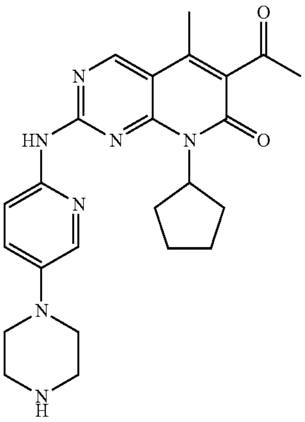

(Palbociclib)

Ref-B

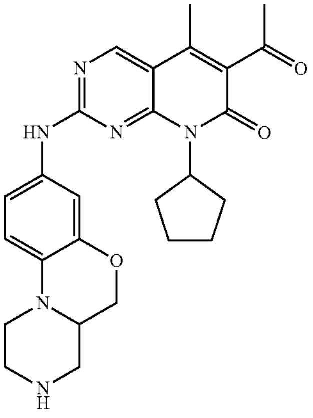

(WO2017101763 Compound 7S)

The compounds of the present invention not only have inhibitory activity against CDK4/CDK6, but also have good inhibitory activity against other CDK subtypes (including CDK2, CDK5, CDK9 and CDK16), so it is a type of pan-CDK inhibitor and also has good inhibitory activity against TRK kinase. There is no other report in the prior art that these compounds have inhibitory activity against the above CDK subtypes and TRK kinases.

In addition, compared with the existing compounds as CDK inhibitors in the field, the compounds of the invention also have significantly improved pharmacokinetic properties. After administration, the peak plasma concentration and exposure of the compounds of the invention in rats were significantly increased, suggesting that the compounds of the invention can be administered at a lower dose.

All literatures mentioned in the present application are incorporated herein by reference, as though each one is individually incorporated by reference. Additionally, it should be understood that after reading the above contents, those skilled in the art can make various changes and modifications to the present invention. These equivalents also fall within the scope defined by the appended claims.

The invention claimed is:

1. A compound of formula (I), or optical isomers, pharmaceutically acceptable salts, prodrugs, deuterated forms, hydrates, or solvates thereof:

(I)

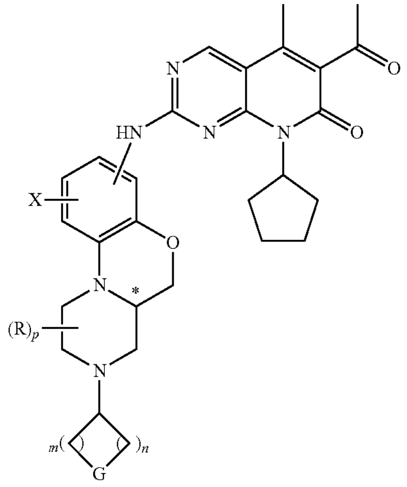

wherein:

"*" indicates a chiral center;

X is hydrogen, deuterium, halogen, $C_{1-4}$ alkyl, $OR^1$, $NR^1R^2$, or $N(R^1)C(O)R^3$;

each R is independently hydrogen or $C_{1-4}$ alkyl; or when two R are simultaneously attached to one carbon atom, the two R and the carbon atom to which they are attached optionally form a carbonyl group (C═O);

G is $NR^f$, O, S, S(O), $S(O)_2$ or $CR^gR^g$;

p is 0, 1, 2 or 3;

m and n are each independently 0, 1, 2 or 3; with the proviso that m and n cannot simultaneously be 0;

$R^1$ and $R^2$ are each independently hydrogen or $C_{1-4}$ alkyl;

$R^3$ is $C_{1-4}$ alkyl, $C_{2-4}$ alkenyl or $C_{2-4}$ alkynyl;

$R^f$ is hydrogen, $C_{1-4}$ alkyl, $C_{1-4}$ haloalkyl, cyano substituted $C_{1-4}$ alkyl, $C_{2-4}$ alkenyl, $C_{2-4}$ alkynyl, $C_{3-8}$ cycloalkyl, 4- to 8-membered heterocyclyl, aryl, heteroaryl, $C(O)R^4$, $C(O)OR^1$, $C(O)NR^1R^2$, $S(O)_2R^4$, or $S(O)_2NR^1R^2$;

each $R^g$ is each independently selected from the group consisting of hydrogen, halogen, and $C_{1-4}$ alkyl; or two $R^g$ together with the carbon atom to which they are attached form a carbonyl group (C═O); or two $R^g$ together with the carbon atom to which they attached form a 3- to 8-membered cyclic structure which optionally comprises 0, 1 or 2 heteroatoms selected from N, O or S;

$R^4$ is $C_{1-4}$ alkyl, $C_{2-4}$ alkenyl, $C_{2-4}$ alkynyl, $C_{3-8}$ cycloalkyl, 4- to 8-membered heterocyclic group, aryl, or heteroaryl;

wherein each of the above alkyl, alkenyl, alkynyl, cycloalkyl, heterocyclyl, aryl and heteroaryl is optionally and independently substituted by 1 to 3 substituents which are each independently selected from the group consisting of halogen, $C_{1-4}$ alkyl, $C_{1-4}$ haloalkyl, $C_{2-4}$ alkenyl, $C_{2-4}$ alkynyl, $C_{3-8}$ cycloalkyl, 3- to 8-membered heterocyclic group, aryl, heteroaryl, CN, $NO_2$, $OR^1$, $SR^1$, $NR^1R^2$, $C(O)R^4$, $C(O)OR^1$, $C(O)NR^1R^2$, $NR^1C(O)R^4$, and $S(O)_2R^4$; the $R^1$, $R^2$ and $R^4$ are defined as above;

unless otherwise specified, the aryl is aromatic groups having 6 to 12 carbon atoms; the heteroaryl is 5- to 15-membered heteroaromatic groups; and the cyclic structure is saturated or unsaturated cyclic groups with or without heteroatoms.

2. The compound of claim 1, or the optical isomers, pharmaceutically acceptable salts, prodrugs, deuterated forms, hydrates or solvates thereof, wherein the "*" is chiral center;

X is hydrogen, deuterium, halogen, $C_{1-4}$ alkyl, $OR^1$, $NR^1R^2$, or $NR^1C(O)R^3$;

each of the R is independently hydrogen or $C_{1-4}$ alkyl; or when two R are simultaneously attached to one carbon atom, the two R and the carbon atom to which they are attached optionally form a carbonyl group (C═O);

G is $NR^f$, O, S, S(O), $S(O)_2$ or $CR^gR^g$;

p is 0, 1, 2 or 3;

m and n are each independently 1, 2 or 3;

$R^1$ and $R^2$ are each independently hydrogen or $C_{1-4}$ alkyl;

$R^3$ is $C_{1-4}$ alkyl, $C_{2-4}$ alkenyl or $C_{2-4}$ alkynyl;

$R^f$ is hydrogen, $C_{1-4}$ alkyl, $C_{1-4}$ haloalkyl, $C_{2-4}$ alkenyl, $C_{2-4}$ alkynyl, $C_{3-8}$ cycloalkyl, 4-to 8-heterocyclyl, aryl, heteroaryl, $C(O)R^4$, $C(O)OR^1$, $C(O)NR^1R^2$, or $S(O)_2R^4$;

each $R^g$ is independently selected from the group consisting of hydrogen, halogen, and $C_{1-4}$ alkyl; or two $R^g$ together with the carbon atom to which they are attached form a carbonyl group (C═O); or two $R^g$ together with the carbon atom to which they attached form a 3- to 8-membered cyclic structure which optionally comprises 0, 1 or 2 heteroatoms selected from N, O or S;

$R^4$ is $C_{1-4}$ alkyl, $C_{2-4}$ alkenyl, $C_{2-4}$ alkynyl, $C_{3-8}$ cycloalkyl, 4- to 8-membered heterocyclic group, aryl, or heteroaryl;

wherein each of the above alkyl, alkenyl, alkynyl, cycloalkyl, heterocyclyl, aryl and heteroaryl is optionally and independently substituted by 1 to 3 substituents which are each independently selected from the group consisting of halogen, $C_{1-4}$ alkyl, $C_{1-4}$ haloalkyl, $C_{2-4}$ alkenyl, $C_{2-4}$ alkynyl, $C_{3-8}$ cycloalkyl, 3- to 8-membered heterocyclic group, aryl, heteroaryl, CN, $NO_2$, $OR^1$, $SR^1$, $NR^1R^2$, $C(O)R^4$, $C(O)OR^1$, $C(O)NR^1R^2$, $NR^1C(O)R^4$, and $S(O)_2R^4$; the $R^1$, $R^2$, and $R^4$ are defined as above;

unless otherwise specified, the aryl is aromatic groups having 6 to 12 carbon atoms; the heteroaryl is 5- to 15-membered heteroaromatic groups; and the cyclic structure is saturated or unsaturated cyclic groups with or without heteroatoms.

3. The compound of claim 1, or the optical isomers, pharmaceutically acceptable salts, prodrugs, deuterated forms, hydrates or solvates thereof, wherein the formula (I) is:

(II)

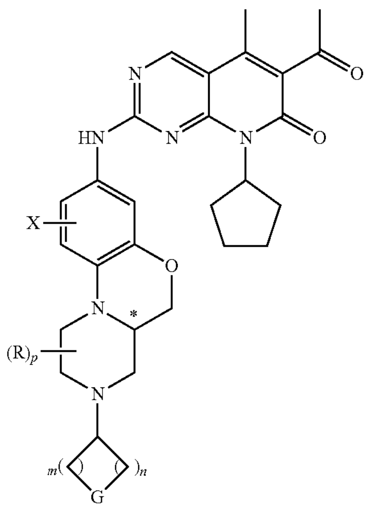

or (III)

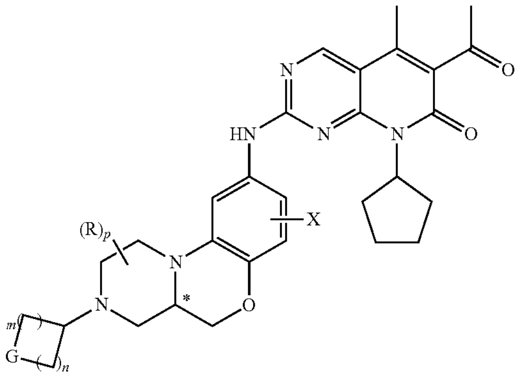

"*" indicates a chiral center;

wherein X, R, G, p, m and n are as defined in claim 1.

4. The compound of claim 1, or the optical isomers, pharmaceutically acceptable salts, prodrugs, deuterated forms, hydrates or solvates thereof, wherein X is hydrogen, halogen, or $C_{1-4}$ alkyl; R is hydrogen, or two R together with the carbon atom to which they connected form a carbonyl (C═O).

5. The compound of claim 1, or the optical isomers, pharmaceutically acceptable salts, prodrugs, deuterated forms, hydrates or solvates thereof, wherein, G is $NR^f$, O or $CR^gR^g$; m and n are each independently 1 or 2; wherein $R^f$ is hydrogen, $C_{1-4}$ alkyl, $C_{1-4}$ haloalkyl, $C_{3-8}$ cycloalkyl, 4- to 8-membered heterocyclic group, aryl, heteroaryl, $C(O)R^4$, or $S(O)_2R^4$; wherein $R^4$ is $C_{1-4}$ alkyl, $C_{2-4}$ alkenyl, $C_{2-4}$ alkynyl, $C_{3-8}$ cycloalkyl, or 4- to 8-membered heterocyclic group.

6. The compound of claim 1, or the optical isomers, pharmaceutically acceptable salts, prodrugs, deuterated derivatives, hydrates or solvates thereof, wherein the formula (I) is:

(IV)

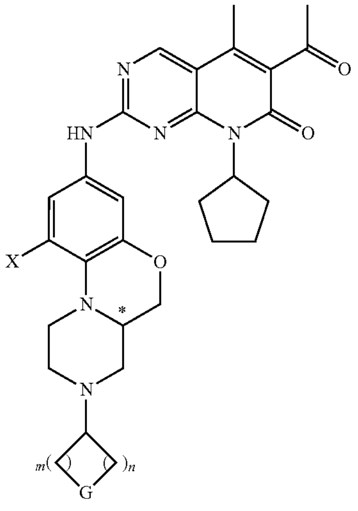

"*" indicates a chiral center;

X is hydrogen, halogen, or $C_{1-4}$ alkyl;

G is $NR^f$, O or $CR^gR^g$; m and n are each independently 1 or 2; wherein $R^f$ is hydrogen, $C_{1-4}$ alkyl, $C_{1-4}$ haloalkyl, $C_{3-8}$ cycloalkyl, 4- to 8-membered heterocyclic group, aryl, heteroaryl, $C(O)R^4$, or $S(O)_2R^4$; wherein $R^4$ is $C_{1-4}$ alkyl, $C_{2-4}$ alkenyl, $C_{2-4}$ alkynyl, $C_{3-8}$ cycloalkyl, or 4- to 8-membered heterocyclic group.

7. The compound of claim 1, or the optical isomers, pharmaceutically acceptable salts, prodrugs, deuterated derivatives, hydrates or solvates thereof, wherein the formula (I) is:

(V)

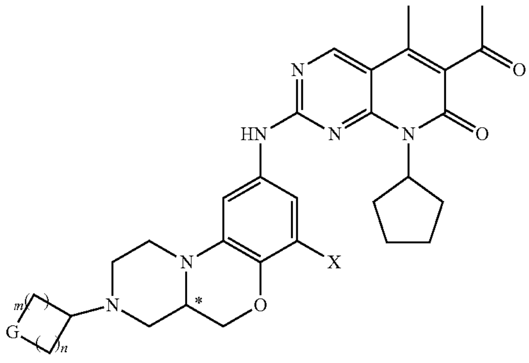

"*" indicates a chiral center;

X is hydrogen, halogen, or $C_{1-4}$ alkyl;

G is $NR^f$, O or $CR^gR^g$; m and n are each independently 1 or 2; wherein $R^f$ is hydrogen, $C_{1-4}$ alkyl, $C_{1-4}$ haloalkyl, $C_{3-8}$ cycloalkyl, 4- to 8-membered heterocyclic group, aryl, heteroaryl, $C(O)R^4$, or $S(O)_2R^4$; wherein $R^4$ is $C_{1-4}$ alkyl, $C_{2-4}$ alkenyl, $C_{2-4}$ alkynyl, $C_{3-8}$ cycloalkyl, or 4- to 8-membered heterocyclic group.

8. The compound of claim 6, or the optical isomers, pharmaceutically acceptable salts, prodrugs, deuterated forms, hydrates or solvates thereof, wherein $R^f$ is hydrogen, $C_{1-4}$ alkyl, $C_{1-4}$ haloalkyl, cyano substituted $C_{1-4}$ alkyl, $C_{3-8}$ cycloalkyl, $C(O)R^4$, or $S(O)_2R^4$; wherein $R^4$ is $C_{1-4}$ alkyl.

9. The compound of claim 5, or the optical isomers, pharmaceutically acceptable salts, prodrugs, deuterated forms, hydrates or solvates thereof, wherein each $R^g$ is independently hydrogen or halogen.

10. The compound of claim 6, or the optical isomers, pharmaceutically acceptable salts, prodrugs, deuterated derivatives, hydrates or solvates thereof, wherein:

"*" indicates a chiral center;

X is hydrogen, fluorine or methyl;

G is $NR^f$, O or $CR^gR^g$; m and n are each independently 1 or 2; wherein $R^f$ is hydrogen, methyl, ethyl, $CH_2CF_3$, $CH_2CN$, cyclopropyl, $C(O)CH_3$, or $S(O)_2CH_3$; each $R^g$ is independently hydrogen or fluorine.

11. The compound of claim 1, or the optical isomers, pharmaceutically acceptable salts, prodrugs, deuterated derivatives, hydrates or solvates thereof, wherein the the formula (I) is a compound selected from the following group, or the mixture with the corresponding enantiomer thereof:

1S

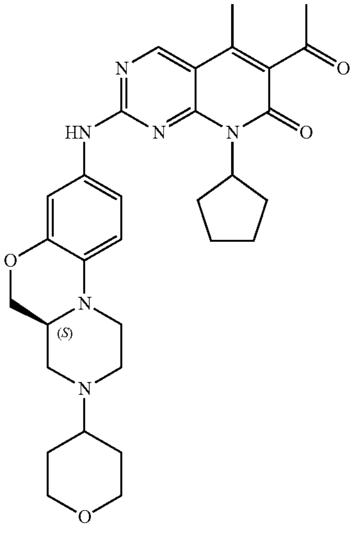

1R
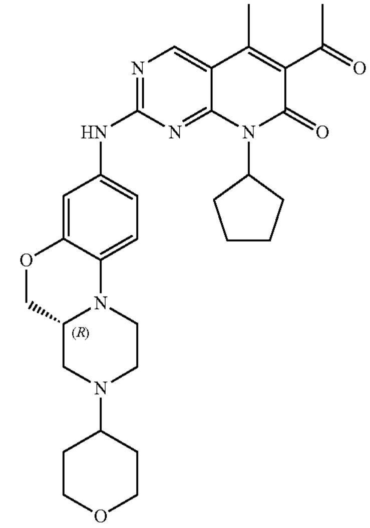
2S
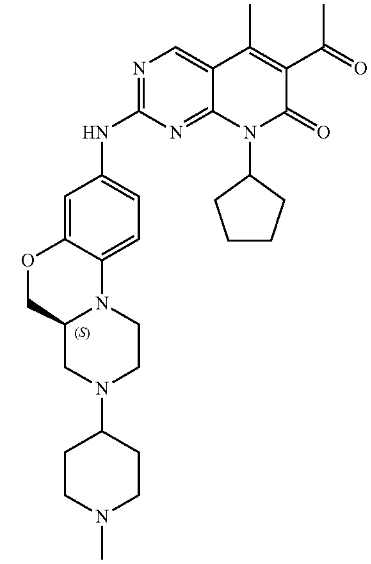
2R
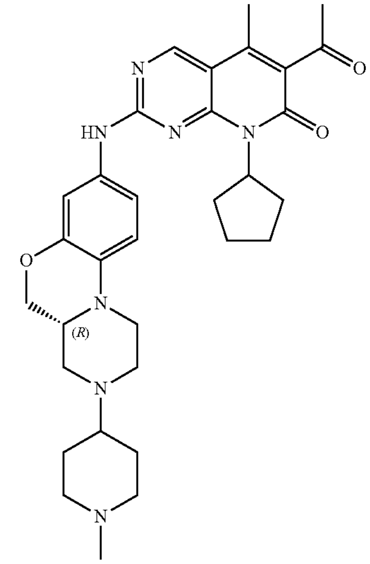
3S
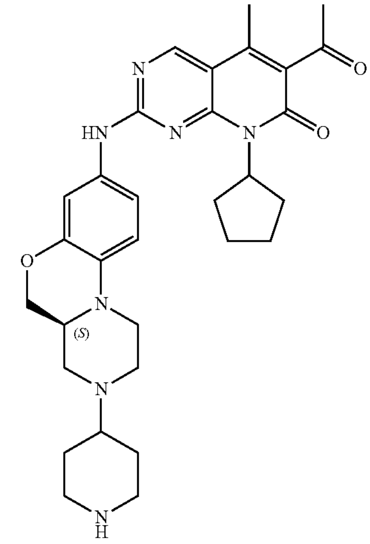
3R
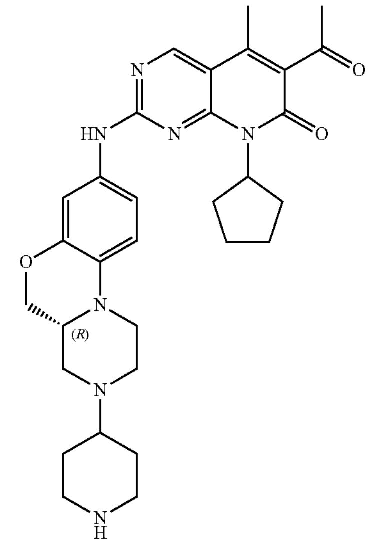

-continued
4S
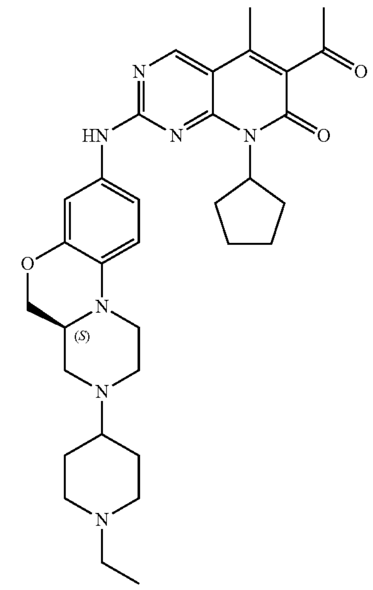
5S
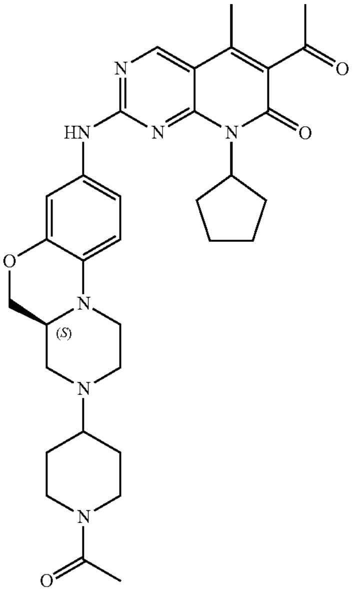
4R
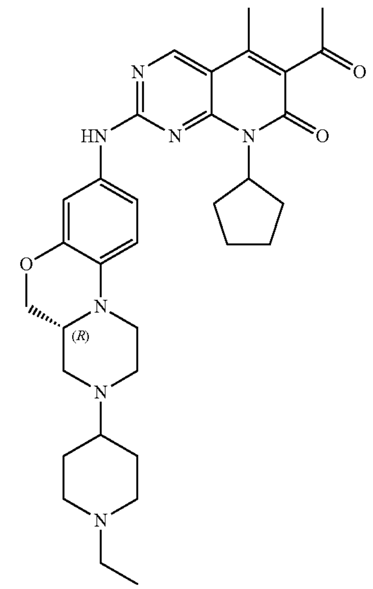
5R
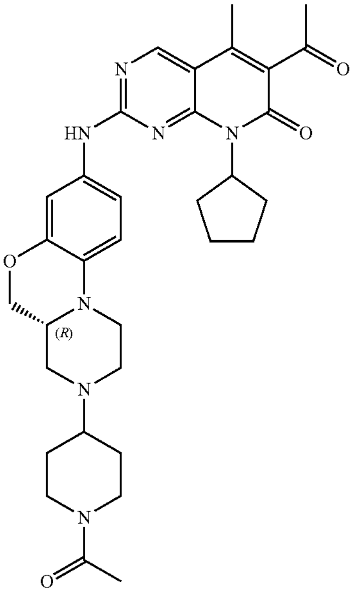

-continued
6S
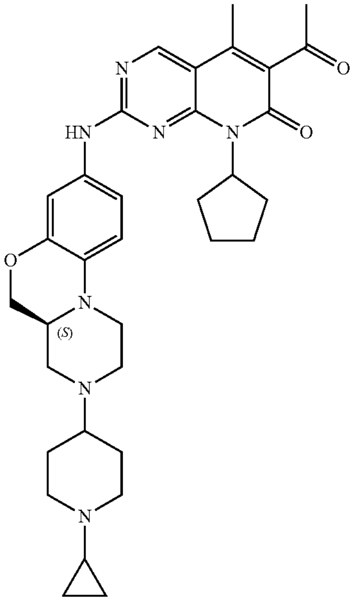
6R
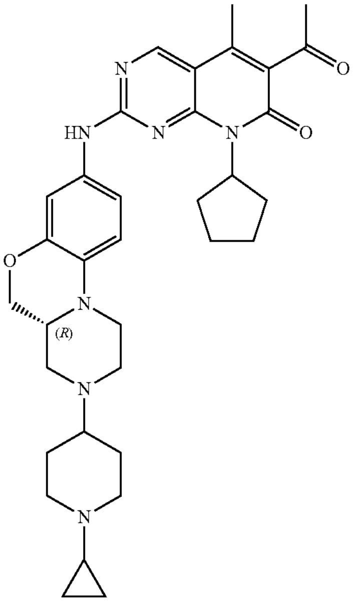
-continued
7S
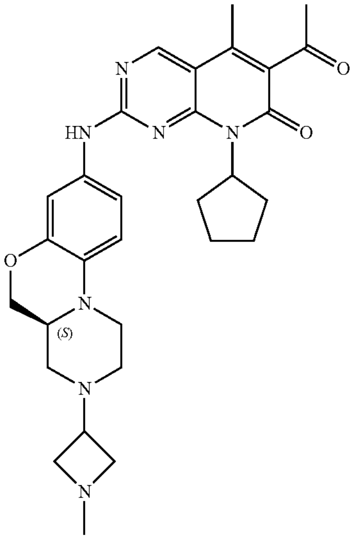
7R
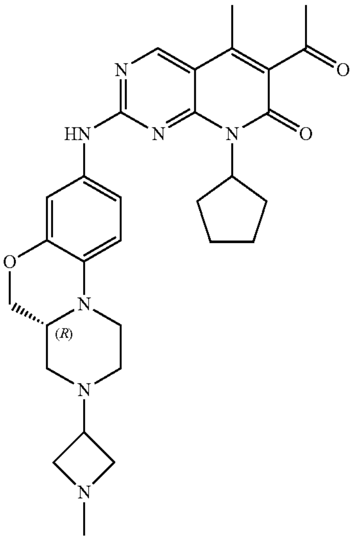
8S
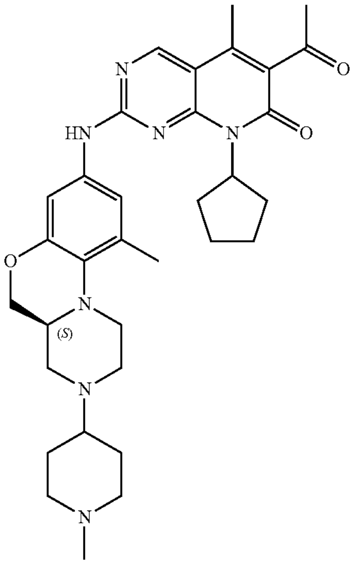

-continued
8R
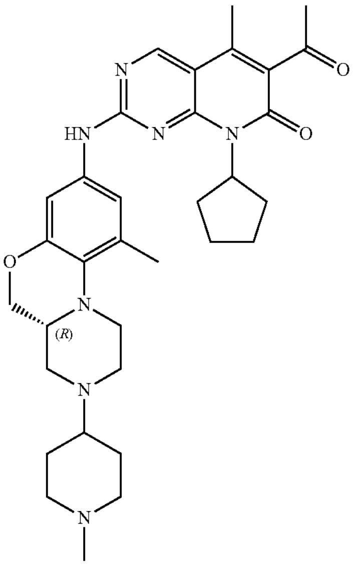
9S
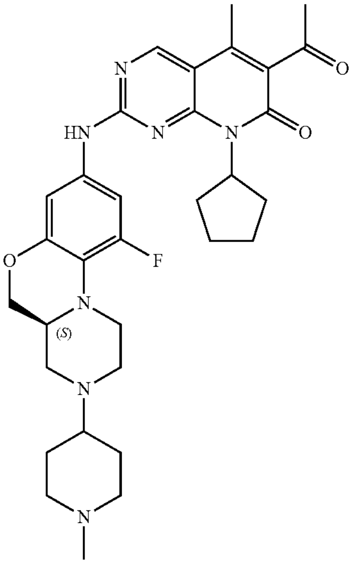
-continued
9R
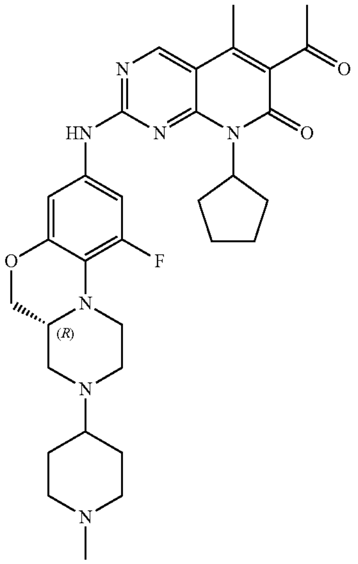
10S
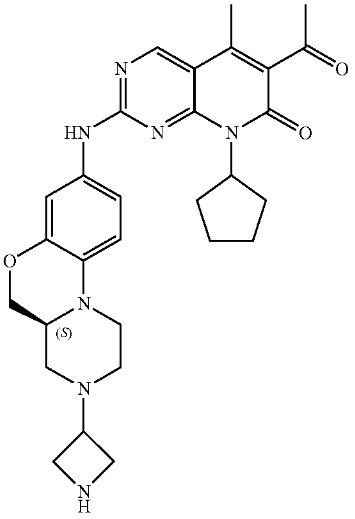
10R
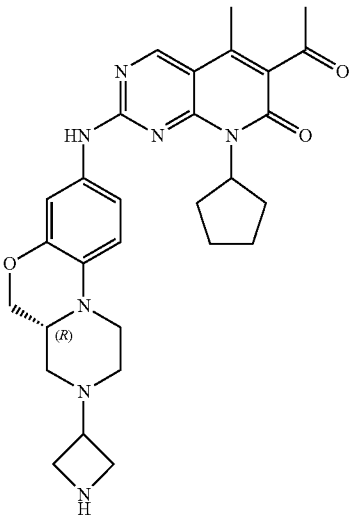

-continued
11S
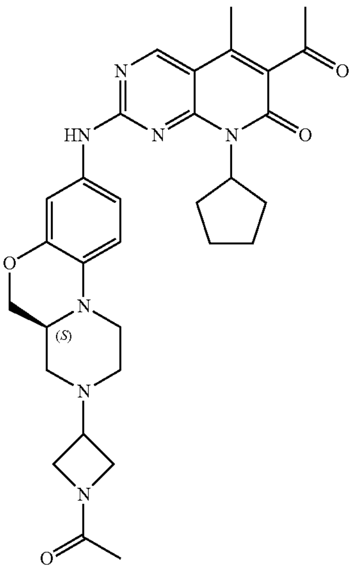
11R
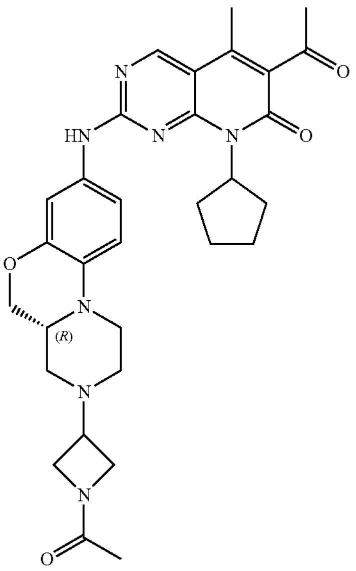
-continued
12S
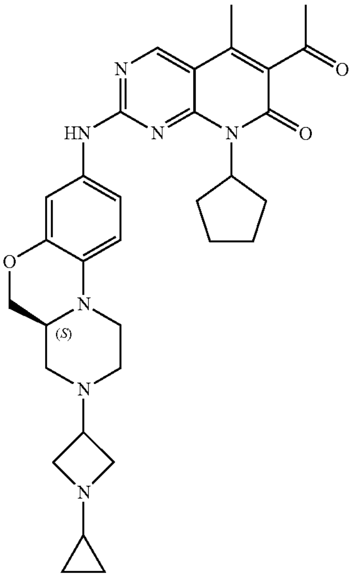
12R
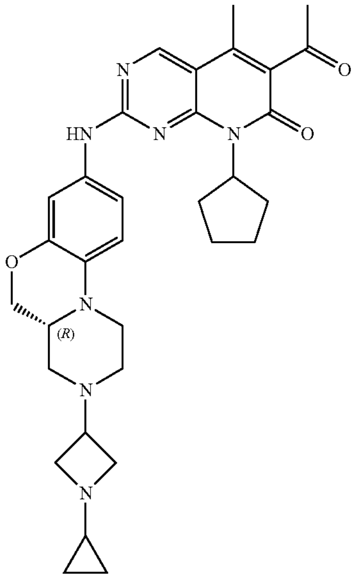
13S
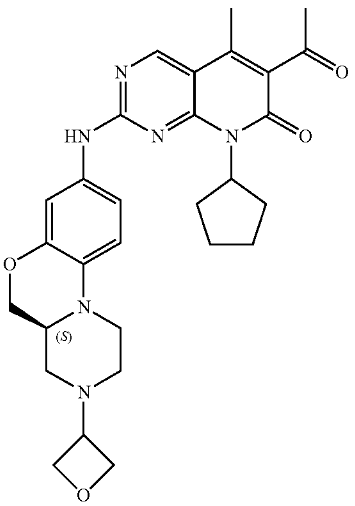

-continued
13R
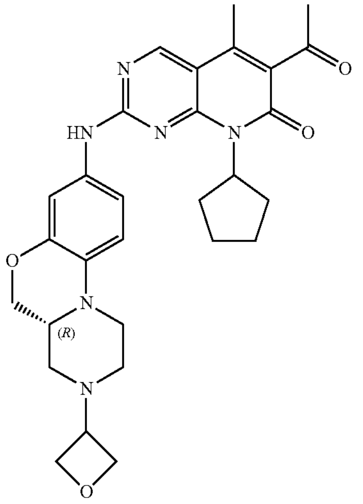
14S
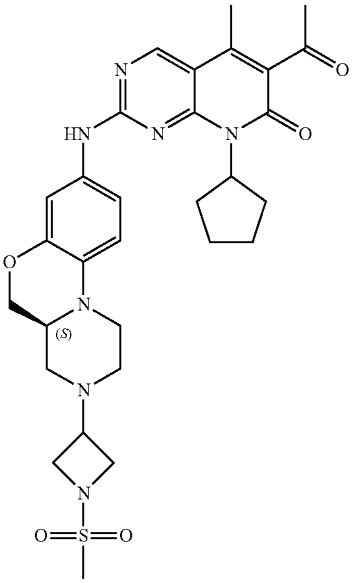
14R
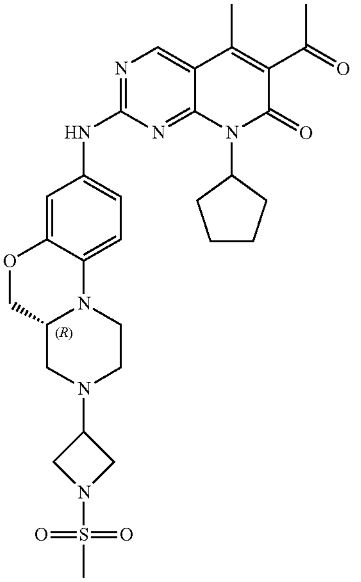
-continued
15S
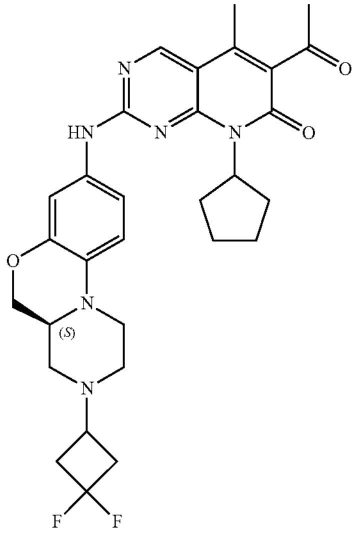
15R
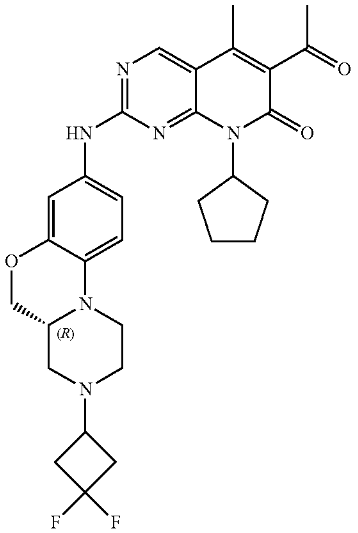
16S
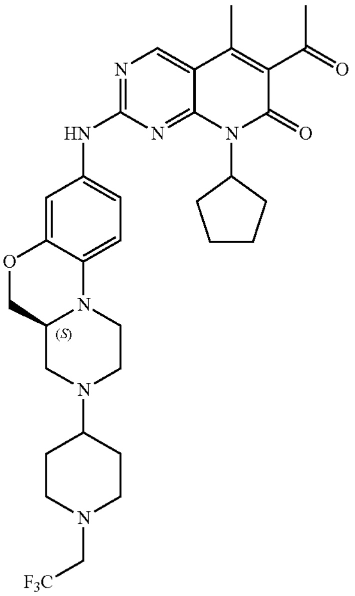

-continued
16R
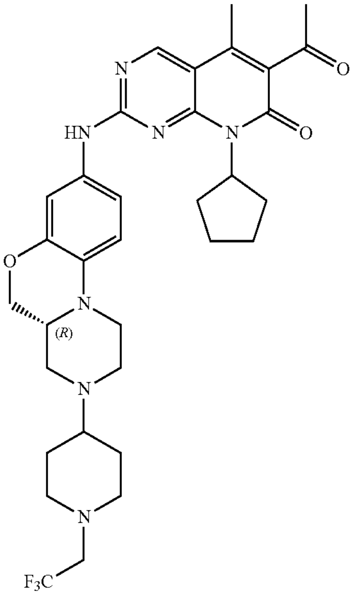
17S
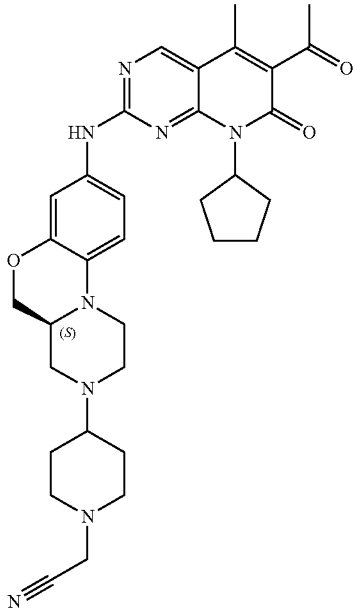
-continued
17R
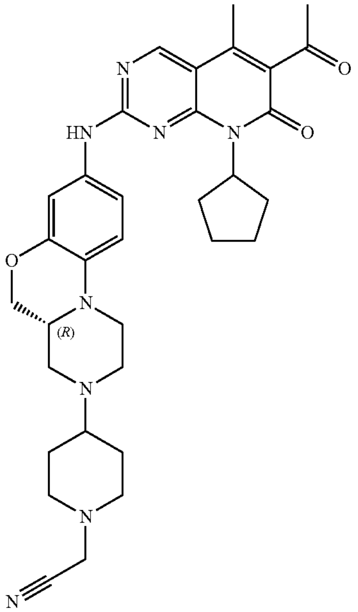
18S
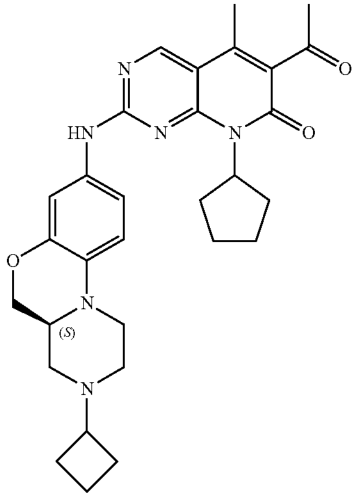
18R
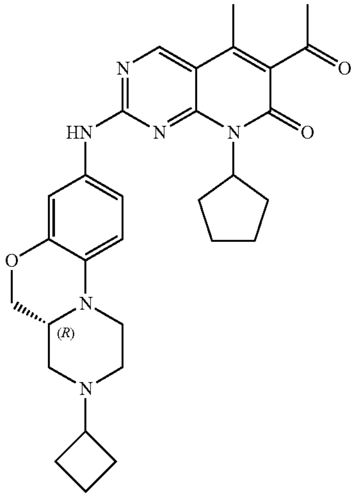

-continued
19S
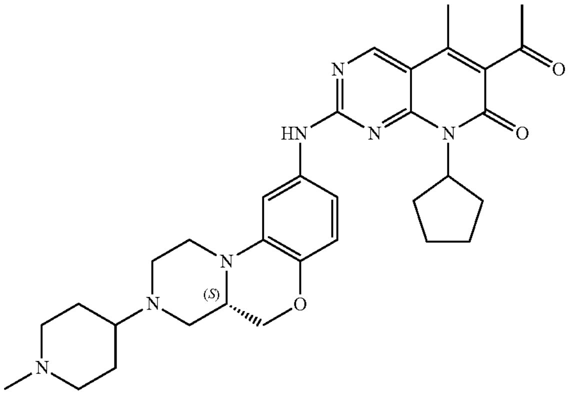
19R
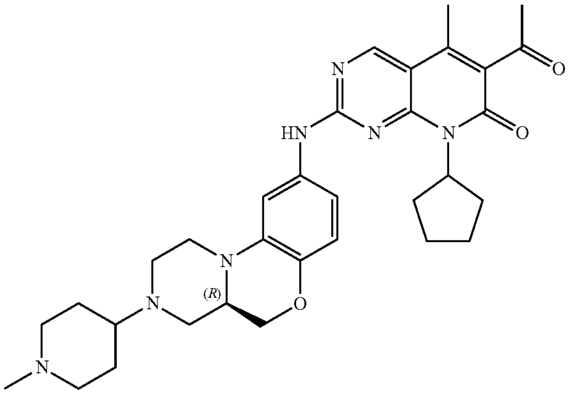
20S
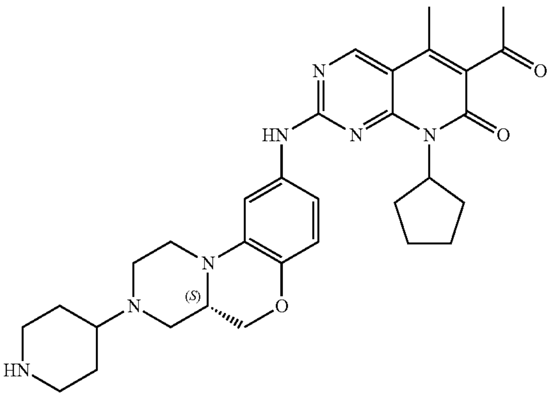
-continued
20R
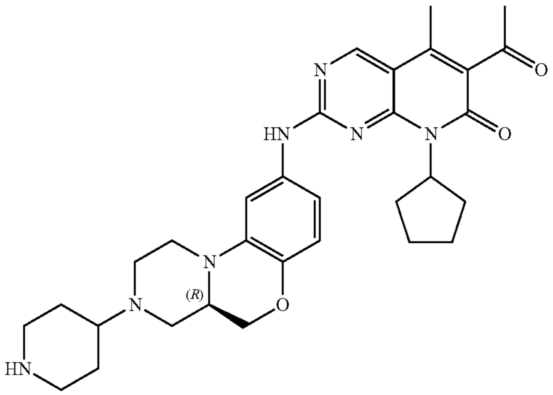
21S
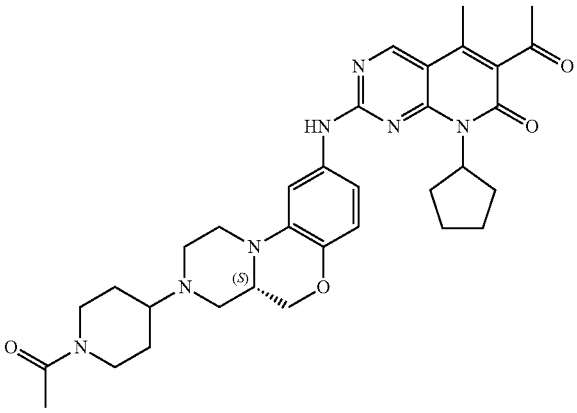
21R
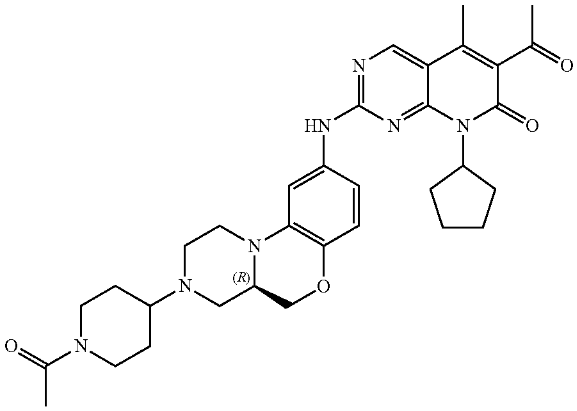

-continued
22S
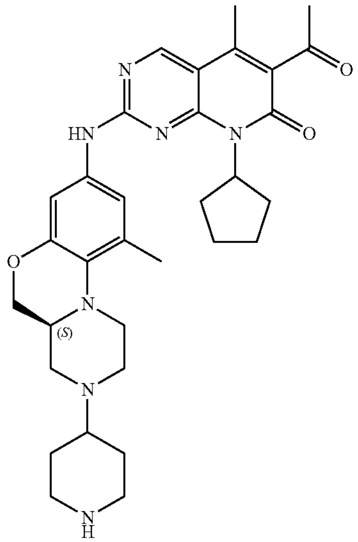
22R
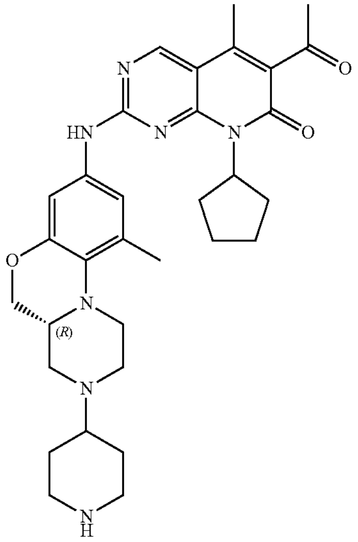
-continued
23S
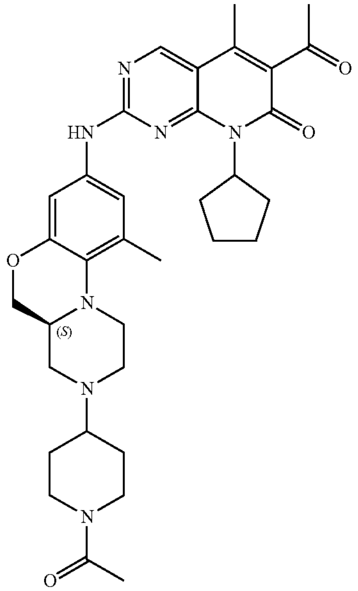
23R
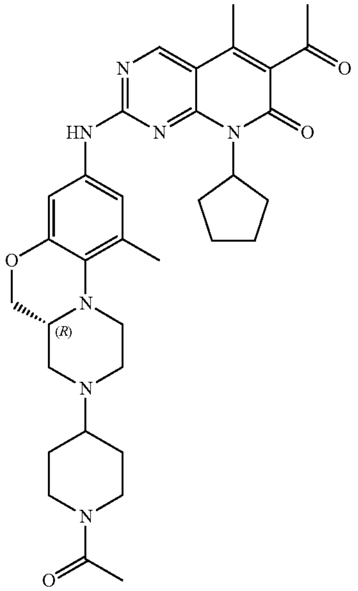

-continued
24S
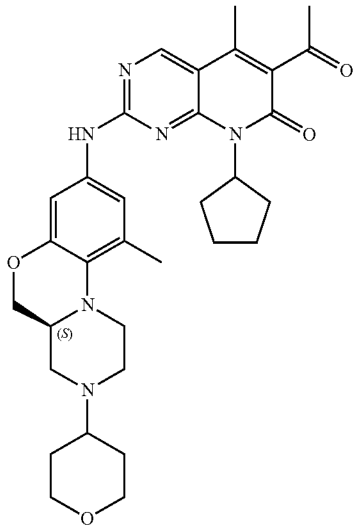
24R
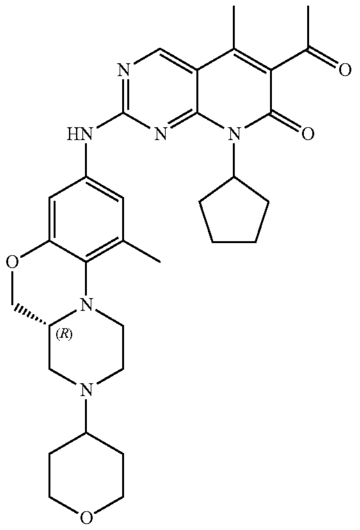
25S
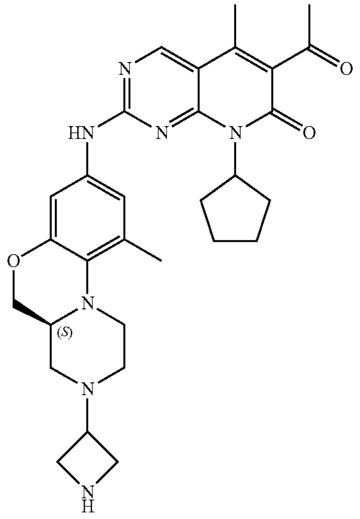
-continued
25R
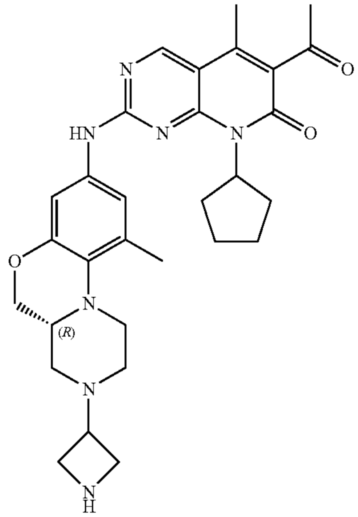
26S
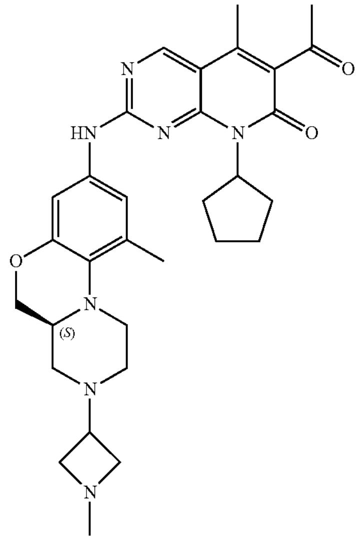
26R
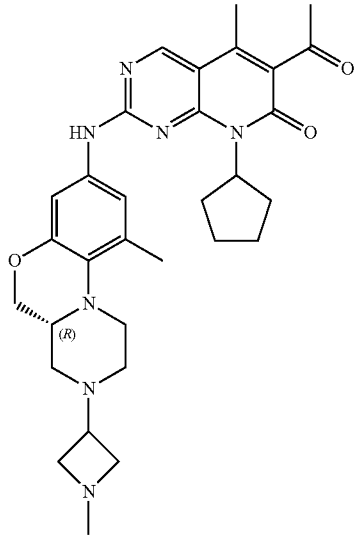

-continued
27S
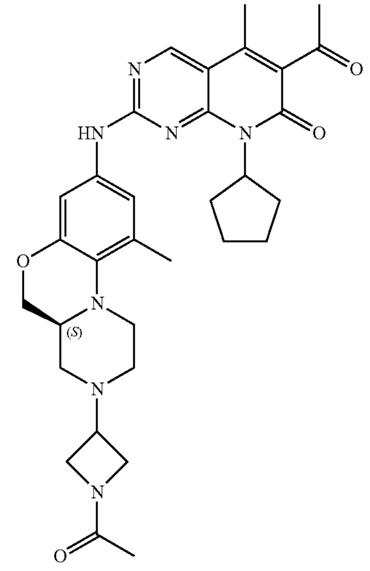
27R
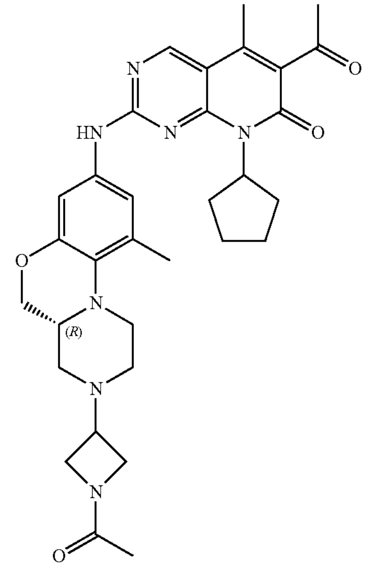
28S
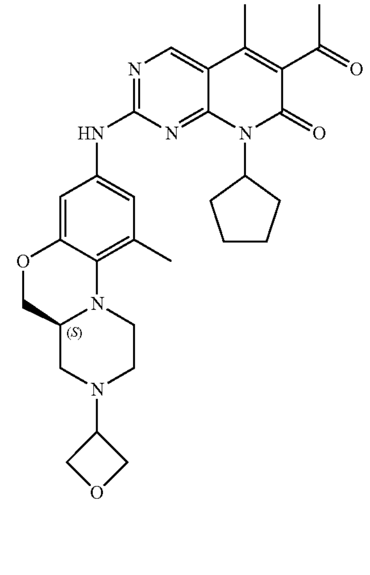
-continued
28R
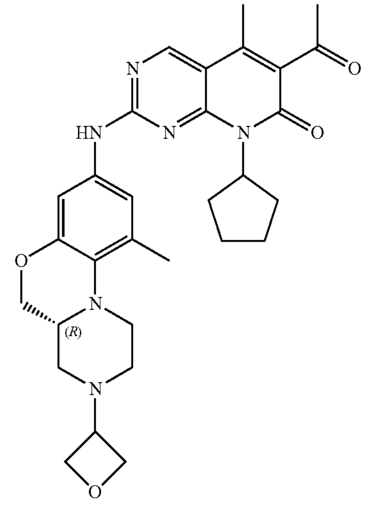
29S
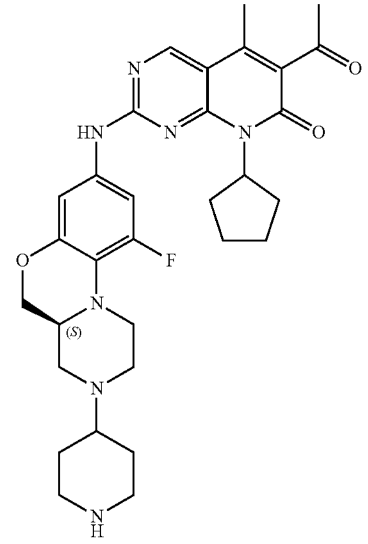
29R
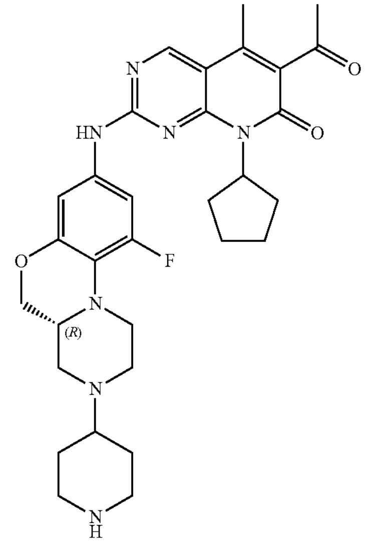

-continued
30S
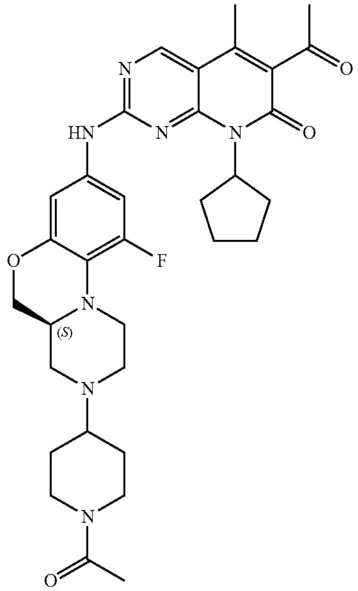
30R
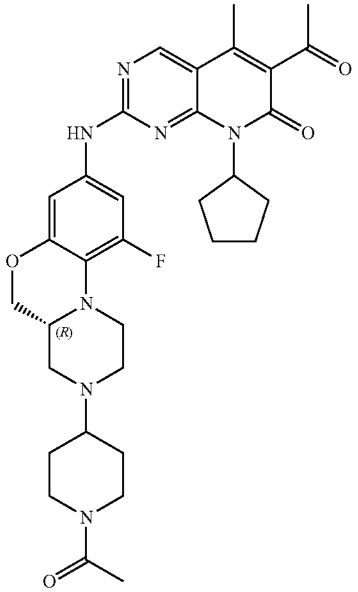
-continued
31S
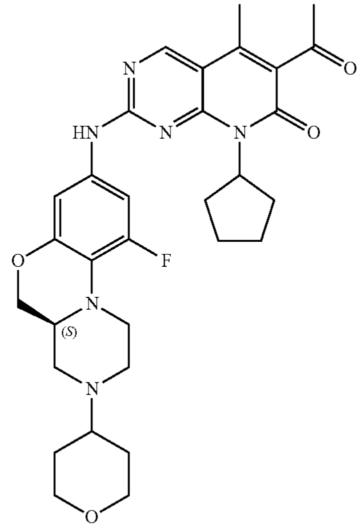
31R
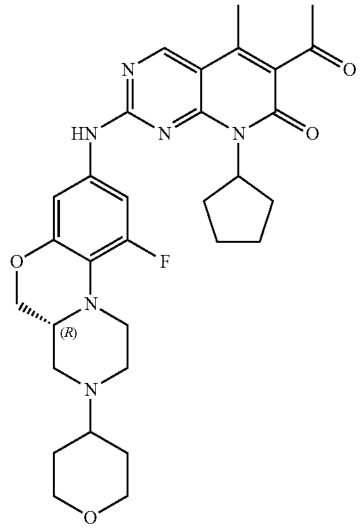
32S
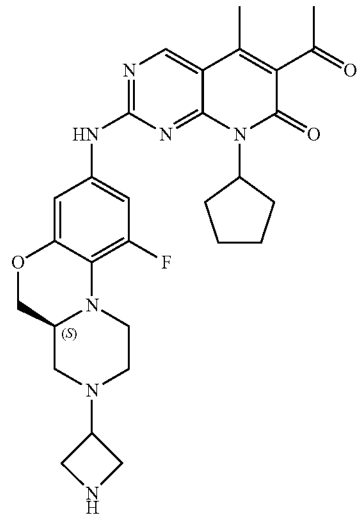

32R
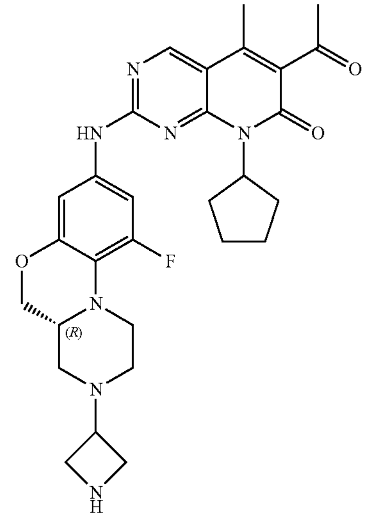
33S
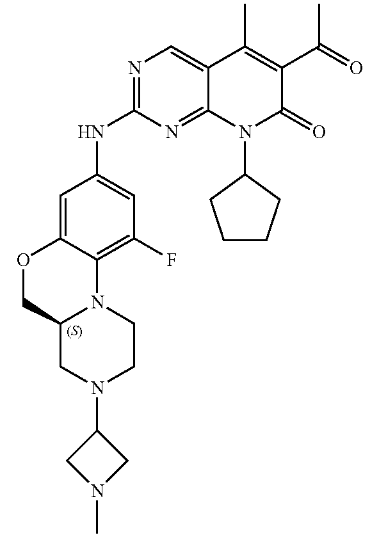
33R
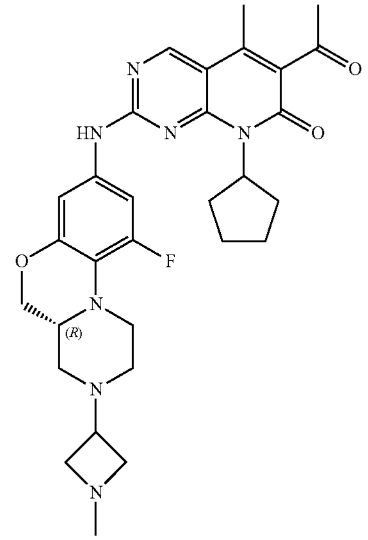
34S
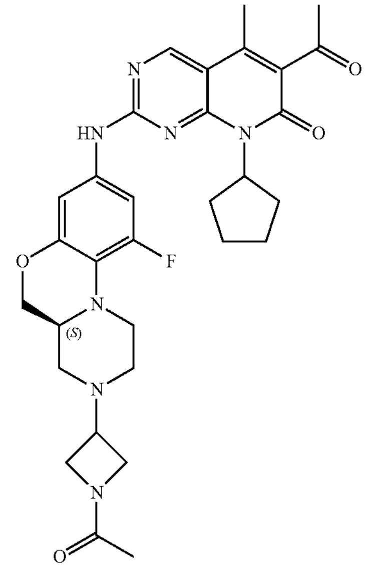
34R
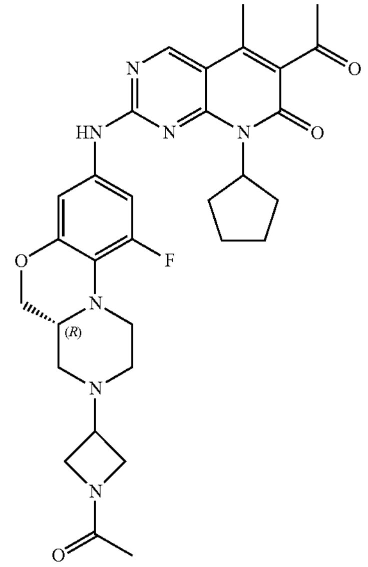
35S
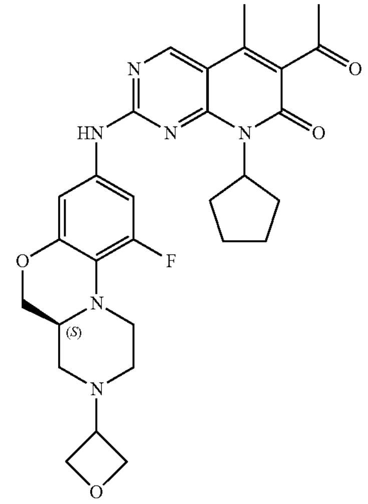

35R
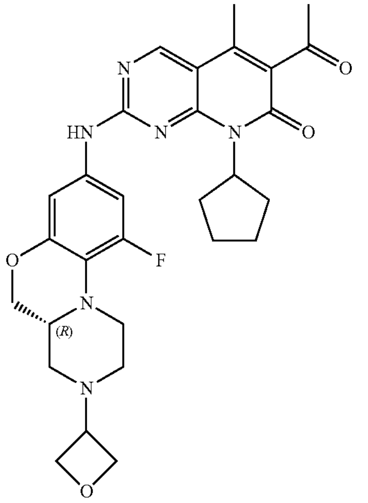
36S
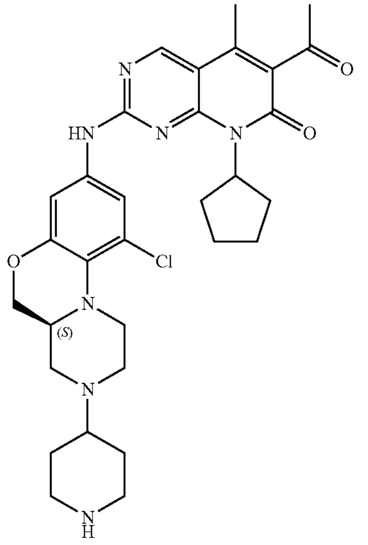
36R
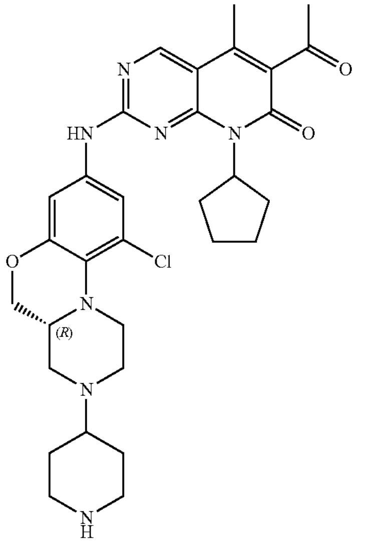
37S
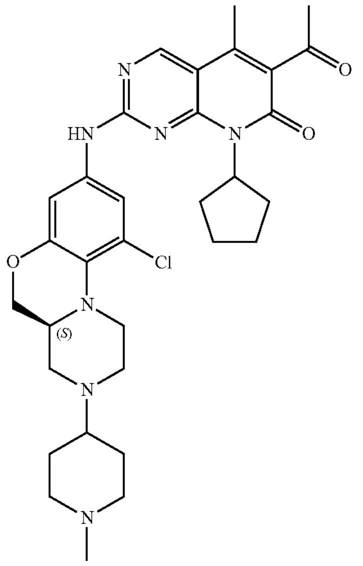
37R
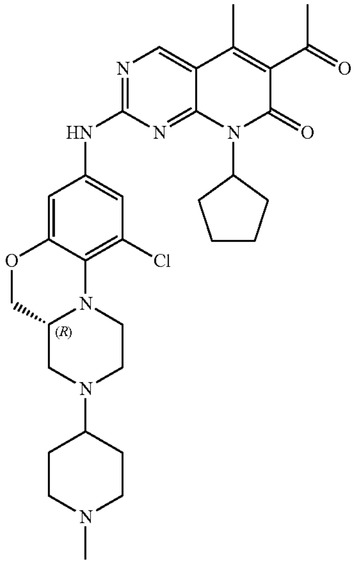

-continued
38S
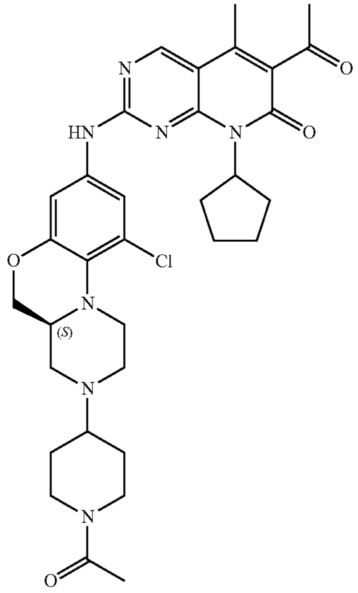
38R
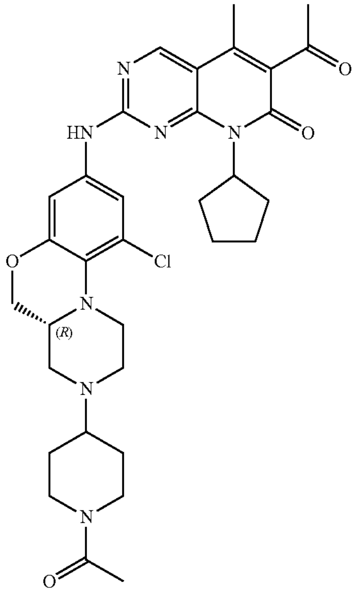
-continued
39S
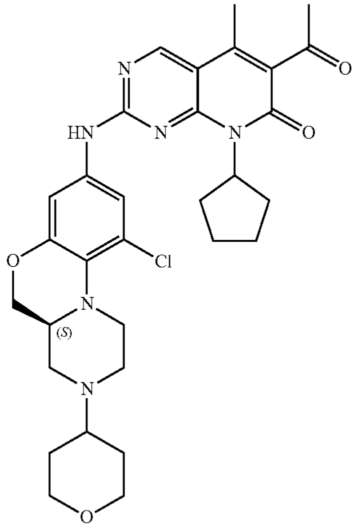
39R
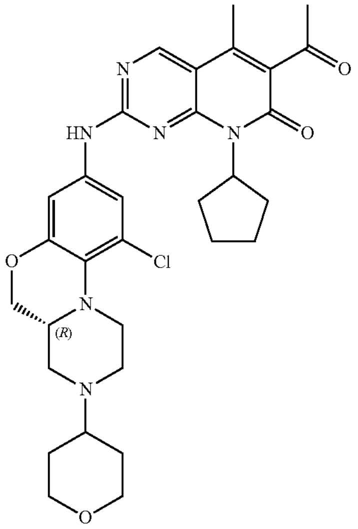
40S
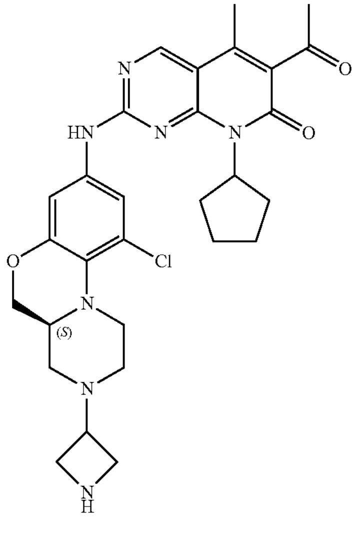

-continued
40R
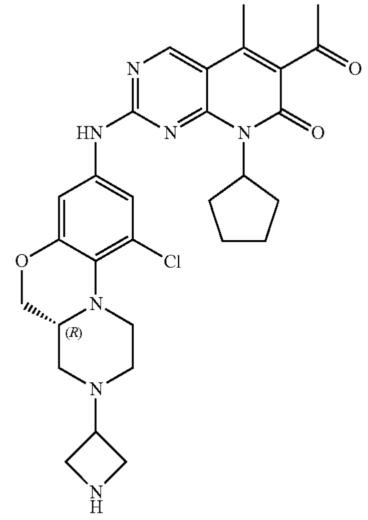
41S
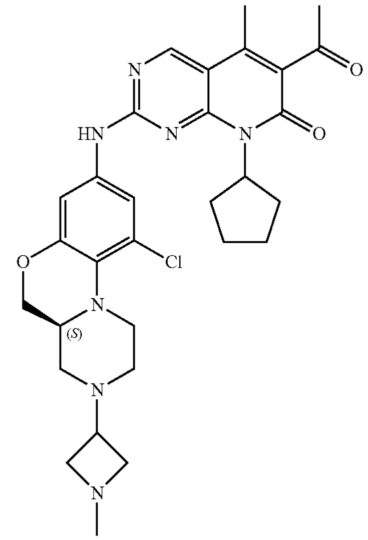
41R
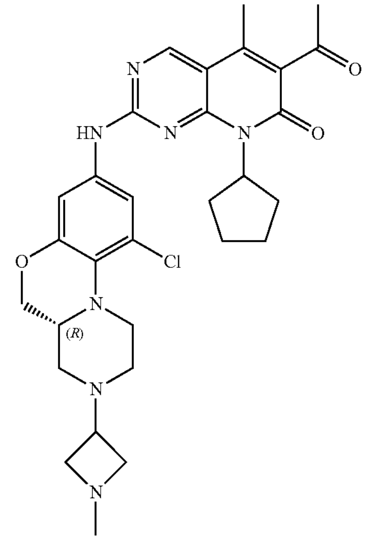
-continued
42S
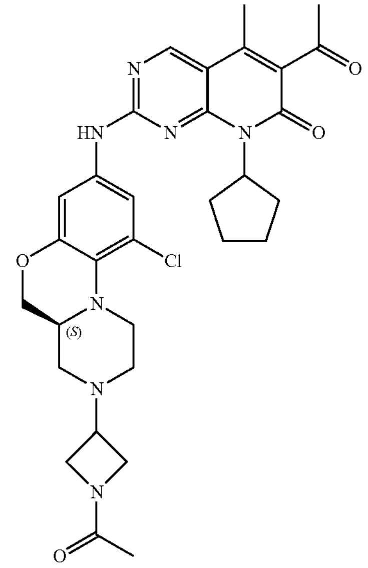
42R
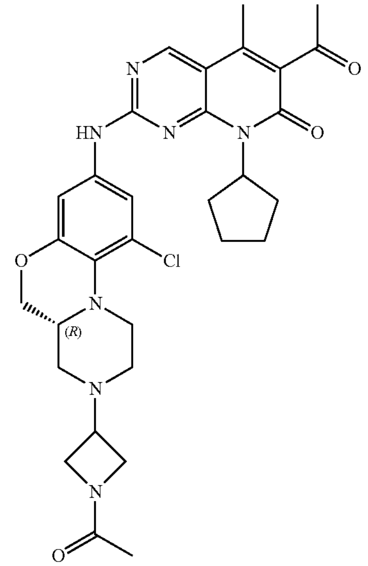
43S
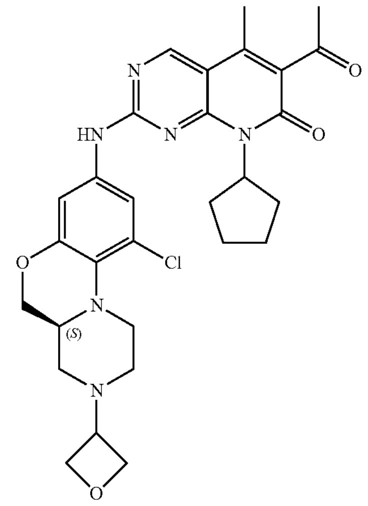

-continued

43R

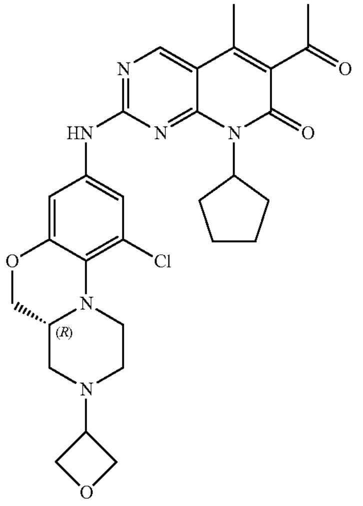

44S

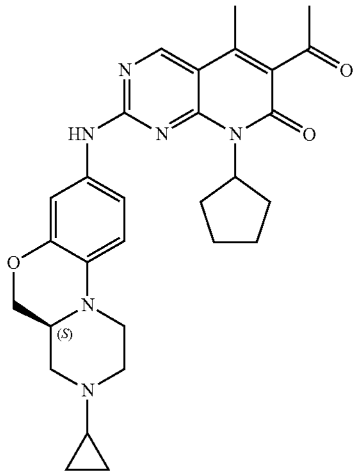

44R

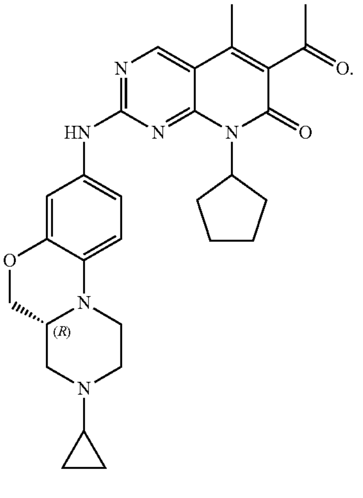

12. The compound of claim 1, or the optical isomers, pharmaceutically acceptable salts, prodrugs, deuterated forms, hydrates or solvates thereof, wherein the salt is hydrochloride.

13. A pharmaceutical composition, comprising: an effective amount of a compound according to claim 1, or the optical isomers, pharmaceutically acceptable salts, prodrugs, deuterated forms, hydrates or solvates thereof.

14. A method of treating a disease associated with kinase activity or expression amount, inhibiting a kinase, or non-therapeutically inhibiting kinase activity, in a subject in need thereof, the method comprising administering an effective amount of the compound of claim 1, or the optical isomers, pharmaceutically acceptable salts, prodrugs, deuterated forms, hydrates or solvates thereof, wherein the kinase is selected from CDK and/or TRK.

15. A method of treating a disease related to high expression of a kinase in a subject in need thereof, comprising administering to the subject a therapeutically effective amount of the pharmaceutical composition of claim 13 wherein the kinase is selected from the group consisting of CDK and TRK.

16. The method of claim 15, wherein the disease is selected from the group consisting of DNA and RNA viral infections, B-cell lymphoma, monocytic leukemia, polycythemia megalosplenica, eosinophilic leukocytosis syndrome, idiopathic thrombocytopenia purpura, systemic giant cell disease, hematological tumors, solid tumors, and neurodegenerative disease.

17. The method of claim 15, wherein the disease is selected from the group consisting of allergic asthma, myelofibrosis, rheumatoid arthritis, inflammatory pain, cancer pain, AIDS, herpes virus and influenza virus, secretory breast cancer, fibrosarcoma, salivary gland cancer, liver cancer, rectal cancer, bladder cancer, pharyngolaryngeal cancer, non-small cell lung cancer, small cell lung cancer, lung adenocarcinoma, lung squamous cell carcinoma, breast cancer, prostate cancer, neurogliocytoma, ovarian cancer, head and neck squamous cell carcinoma, cervical cancer, esophageal cancer, kidney cancer, pancreas cancer, colon cancer, skin cancer, lymphoma, stomach cancer, multiple myeloma, brain tumor, lung cancer, Alzheimer's disease, and Parkinson's disease.

18. A method for the preparation of compound of claim 1, wherein comprises:

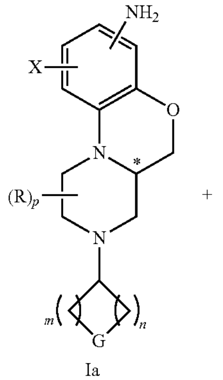

Ia

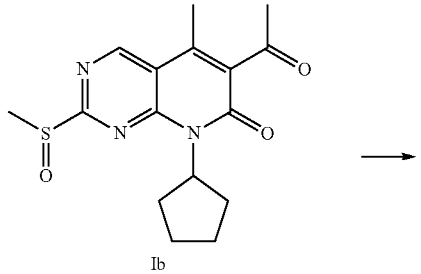

Ib

-continued

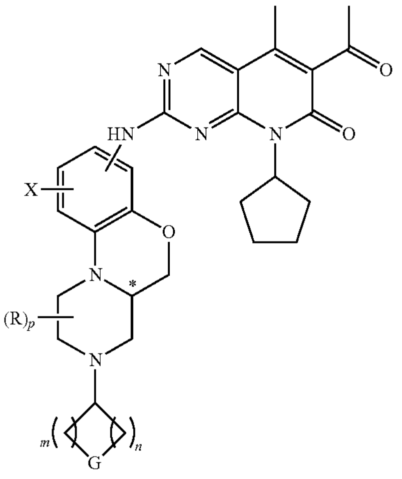

I in an inert solvent, reacting a compound of formula Ia and a compound of formula Ib to obtain the compound of formula I.

19. The method of claim 18, wherein the method further comprises the following steps:

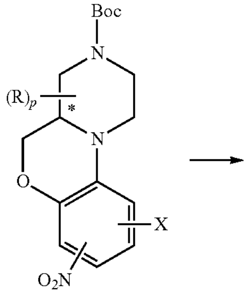

1-A3

-continued

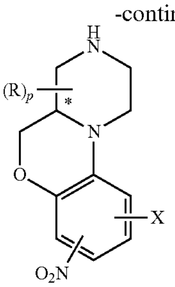

1-A3-a

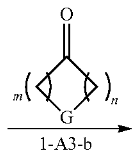

1-A3-b

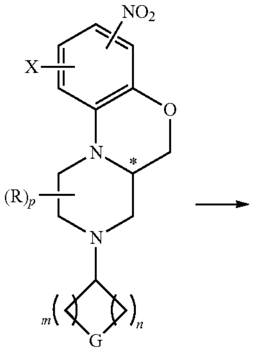

1-A4

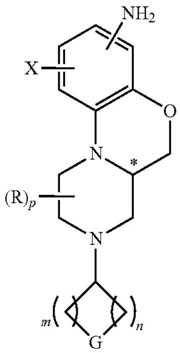

Ia (1) in an inert solvent, deprotecting a compound of formula 1-A3 to give a compound of formula 1-A3-a;

(2) in an inert solvent, subjecting the compound of formula 1-A3-a to reductive amination reaction with a compound of formula 1-A3-b to obtain a compound of formula 1-A4;

(i) in an inert solvent, reducing the compound of formula 1-A4 to provide the compound of formula Ia.

20. The compound of claim 7, or the optical isomers, pharmaceutically acceptable salts, prodrugs, deuterated derivatives, hydrates or solvates thereof, wherein:

"*" indicates a chiral center;

X is hydrogen, fluorine or methyl;

G is $NR^f$, O or $CR^gR^g$; m and n are each independently 1 or 2; wherein $R^f$ is hydrogen, methyl, ethyl, $CH_2CF_3$, $CH_2CN$, cyclopropyl, $C(O)CH_3$, or $S(O)_2CH_3$; each $R^g$ is independently hydrogen or fluorine.

* * * * *